US009580749B2

(12) United States Patent
Mao et al.

(10) Patent No.: US 9,580,749 B2
(45) Date of Patent: Feb. 28, 2017

(54) DYES AND LABELED MOLECULES

(71) Applicants: Biotium, Inc., Hayward, CA (US); AlleLogic Biosciences Corporation, Hayward, CA (US)

(72) Inventors: Fei Mao, Fremont, CA (US); Wai-Yee Leung, San Ramon, CA (US); Xing Xin, Foster City, CA (US)

(73) Assignee: Biotium, Inc., Hayward, CA (US)

( * ) Notice: Subject to any disclaimer, the term of this patent is extended or adjusted under 35 U.S.C. 154(b) by 284 days.

(21) Appl. No.: 13/968,122

(22) Filed: Aug. 15, 2013

(65) Prior Publication Data

US 2014/0106349 A1 Apr. 17, 2014

Related U.S. Application Data

(63) Continuation of application No. 12/820,983, filed on Jun. 22, 2010, now Pat. No. 8,530,195, which is a continuation of application No. 11/377,253, filed on Mar. 16, 2006, now Pat. No. 7,776,567.

(60) Provisional application No. 60/663,613, filed on Mar. 17, 2005.

(51) Int. Cl.
| | | |
|---|---|---|
| *C07H 19/04* | (2006.01) | |
| *C12Q 1/68* | (2006.01) | |
| *C07H 21/00* | (2006.01) | |
| *C07D 209/08* | (2006.01) | |
| *C07D 213/38* | (2006.01) | |
| *C07D 221/10* | (2006.01) | |
| *C07D 417/06* | (2006.01) | |
| *C07D 417/14* | (2006.01) | |
| *C07D 491/147* | (2006.01) | |
| *C09B 15/00* | (2006.01) | |

(52) U.S. Cl.
CPC ......... *C12Q 1/6876* (2013.01); *C07D 209/08* (2013.01); *C07D 213/38* (2013.01); *C07D 221/10* (2013.01); *C07D 417/06* (2013.01); *C07D 417/14* (2013.01); *C07D 491/147* (2013.01); *C07H 21/00* (2013.01); *C09B 15/00* (2013.01); *C12Q 1/686* (2013.01); *C12Q 1/6851* (2013.01)

(58) Field of Classification Search
CPC ........ C07H 21/00; C12Q 1/6876; C09B 15/00
USPC .................. 536/26.6; 435/6.1, 91.1
See application file for complete search history.

(56) References Cited

U.S. PATENT DOCUMENTS

| | | |
|---|---|---|
| 4,883,867 A | 11/1989 | Lee et al. |
| 5,118,801 A | 6/1992 | Lizardi et al. |
| 5,210,015 A | 5/1993 | Gelfand et al. |
| 5,312,728 A | 5/1994 | Lizardi et al. |
| 5,321,130 A | 6/1994 | Yue et al. |
| 5,401,847 A | 3/1995 | Glazer et al. |
| 5,403,928 A | 4/1995 | Arrhenuis |
| 5,410,030 A | 4/1995 | Yue et al. |
| 5,436,134 A | 7/1995 | Haugland et al. |
| 5,445,946 A | 8/1995 | Roth et al. |
| 5,534,416 A | 7/1996 | Millard et al. |
| 5,538,848 A | 7/1996 | Livak et al. |
| 5,545,535 A | 8/1996 | Roth et al. |
| 5,582,977 A | 12/1996 | Yue et al. |
| 5,646,264 A | 7/1997 | Glazer et al. |
| 5,656,449 A | 8/1997 | Yue |
| 5,658,751 A | 8/1997 | Yue et al. |
| 5,691,146 A | 11/1997 | Mayrand |
| 5,763,162 A | 6/1998 | Glazer et al. |
| 5,846,726 A | 12/1998 | Nadeau et al. |
| 5,863,753 A | 1/1999 | Haugland et al. |
| 5,925,517 A | 7/1999 | Tyagi et al. |
| 5,977,344 A | 11/1999 | Glazer et al. |
| 6,037,137 A | 3/2000 | Komoriya et al. |
| 6,150,097 A | 11/2000 | Tyagi et al. |
| 6,258,569 B1 | 7/2001 | Livak et al. |
| 6,277,570 B1 | 8/2001 | Wood et al. |
| 6,569,627 B2 | 5/2003 | Wittwer et al. |
| 6,635,427 B2 | 10/2003 | Wittwer et al. |
| 6,664,047 B1 | 12/2003 | Haugland et al. |
| 7,166,478 B2 | 1/2007 | Stavrianopoulos et al. |
| 7,387,887 B2 | 6/2008 | Wittwer et al. |
| 7,601,498 B2 | 10/2009 | Mao et al. |
| 7,776,567 B2 | 8/2010 | Mao et al. |
| 7,803,943 B2 | 9/2010 | Mao et al. |
| 8,232,050 B2 | 7/2012 | Mao et al. |
| 8,530,195 B2 | 9/2013 | Mao et al. |

(Continued)

FOREIGN PATENT DOCUMENTS

| | | |
|---|---|---|
| CN | 1114359 A | 1/1996 |
| EP | 1344835 A2 | 9/2003 |
| EP | 1348713 A2 | 10/2003 |
| EP | 1373250 B1 | 8/2006 |
| JP | 2002327130 | 11/2002 |
| WO | WO 2004/038038 A2 | 5/2004 |
| WO | WO 2006/020947 A2 | 2/2006 |
| WO | WO 2006/020947 A3 | 8/2008 |

OTHER PUBLICATIONS

Notice of allowance dated Feb. 5, 2014 for U.S. Appl. No. 13/541,313.
Notice of allowance dated Mar. 3, 2015 for U.S. Appl. No. 13/962,668.
Notice of allowance dated Mar. 9, 2009 for U.S. Appl. No. 11/377,254.

(Continued)

Primary Examiner — Jezia Riley
(74) Attorney, Agent, or Firm — Wilson Sonsini Goodrich & Rosati

(57) ABSTRACT

Dimeric and trimeric nucleic acid dyes, and associated systems and methods are provided. Such a dye may form a hairpin-like structure that enables it to stain nucleic acids via a release-on-demand mechanism, for example. Such a dye may have low background fluorescence in the absence of nucleic acids and high fluorescence in the presence of nucleic acids, upon binding therewith, for example. A dye provided herein may be useful in a variety of applications, such as in DNA quantitation in real-time PCR, for example.

6 Claims, 16 Drawing Sheets

(56) References Cited

U.S. PATENT DOCUMENTS

| | | | |
|---|---|---|---|
| 8,753,814 B2 | 6/2014 | Mao et al. | |
| 8,877,437 B1 | 11/2014 | Mao et al. | |
| 9,102,835 B2 | 8/2015 | Mao et al. | |
| 2003/0008316 A1 | 1/2003 | Smith et al. | |
| 2003/0092062 A1 | 5/2003 | Reddy et al. | |
| 2004/0132046 A1 | 7/2004 | Westman et al. | |
| 2005/0239096 A1 | 10/2005 | Beaudet et al. | |
| 2006/0211028 A1 | 9/2006 | Mao et al. | |
| 2006/0211029 A1 | 9/2006 | Mao et al. | |
| 2010/0009454 A1 | 1/2010 | Mao et al. | |
| 2010/0317016 A1 | 12/2010 | Mao et al. | |
| 2010/0323453 A1 | 12/2010 | Mao et al. | |
| 2013/0167309 A1 | 7/2013 | Mao et al. | |
| 2014/0073058 A1 | 3/2014 | Mao et al. | |

OTHER PUBLICATIONS

Notice of allowance dated Mar. 29, 2012 for U.S. Appl. No. 12/854,436.
Notice of allowance dated Apr. 28, 2010 for U.S. Appl. No. 11/377,253.
Notice of allowance dated May 13, 2013 for U.S. Appl. No. 12/820,983.
Notice of allowance dated Jun. 24, 2014 for U.S. Appl. No. 12/976,917.
Notice of allowance dated Jun. 30, 2010 for U.S. Appl. No. 12/484,968.
Office action dated Aug. 28, 2014 for U.S. Appl. No. 13/962,668.
U.S. Appl. No. 12/976,917, filed Dec. 22, 2010, Mao et al.
U.S. Appl. No. 13/962,668, filed Aug. 8, 2013, Mao et al.
"Lab Ref: A Handbook of Recipes, Reagents, and Other Reference Tools for Use at the Bench," Electrophoresis of DNA, RNA, and Protein, Section 3A, 2002, pp. 62-80.
"Nucleic Acid Stains and Products for Genomics Studies," www.biotium.com—Fluorescent Probes and Related Biochemical Reagents for Life Science, Section 9, 2005-2006, pp. 161-173.
Adkins, et al. Visualization of DNA in Agarose Gels as Migrating Colored Bands: Applications for Preparative Gels and Educational Demonstrations. Analytical Biochemistry, vol. 240, Article No. 0325, 1996, pp. 17-23.
Albert, A. The Acridines. Their Preparation, Physical, Chemical, and Biological Properties, and Uses. Angew. Chem. internat. Edi, vol. 6, No. 10, 1967, 1 page.
Atwell, et al. Potential antitumor agents. 45. Synthesis, DNA-binding interaction, and biological activity of triacrdine derivatives. J Med Chem. Jan. 1986;29(1):69-74.
Barak, et al. Fluorescent Low Density Lipoprotein for Observation of Dynamics of Individual Receptor Complexes on Cultured Human Fibroblasts, The Journal of Cell Biology, vol. 90, 1981, pp. 595-604.
Bengtsson, et al.,A New Minor Groove Binding Asymmetric Cyanine Reporter Dye for Real-Time PCR. Nucleic Acid Research, vol. 31, No. 8, 2003, pp. 1-5.
Benson, et al. Heterodimeric DNA-Binding Dyes Designed for Energy Transfer: Synthesis and Spectroscopic Properties. Nucleic Acids Research, vol. 21, No. 24, 1993, pp. 5727-5735.
Capelle, et al. Deoxyribonucleic Acid Bifunctional Intercalators: Kinetic Investigation of the Binding of Several Acridine Dimers to Deoxyribonucleic Acid. Biochemistry, vol. 18, No. 15, 1979, pp. 3354-3362.
Carreon, et al. Thiazole Orange-Peptide Conjugates: Sensitivity of DNA Binding to Chemical Structure. Organic Letters, vol. 6, No. 4, 2004, pp. 517-519.
Chakraborty, et al. Synthesis and DNA Binding Properties of Pyrrole Amino Acid-Containing Peptides. Tetrahedron Letters, vol. 46, 2005, pp. 647-651.
Dervan. Molecular Recognition of DNA by Small Molecules. Bioorganic & Medicinal Chemistry, vol. 9, 2001, pp. 2215-2235.
Eldho, et al. One Pot Synthesis of a Acridinylalkanoic Acids and Novel Bisacridines. Synthetic Communications, 29(22), 1999, pp. 4007-4014.
European search report and search opinion dated Feb. 14, 2012 for Application No. 11175090.7.
Fukunaga, et al. Production of Frameshift Mutations in Salmonella by Phenanthridinium Derivatives: Enzymatic Activation and Photoaffinity Labeling. Mutation Research, vol. 127, 1984, pp. 31-37.
Gaugain, et al. DNA Bifunctional Intercalators. 1. Synthesis and Conformational Properties of an Ethidium Homodimer and of an Acridine Ethidium Heterodimer. Biochemistry, vol. 17, No. 24, Nov. 28, 1978, pp. 5071-5078.
Gaugain, et al. DNA Bifunctional Intercalators. 2. Fluorescence Properties and DNA Binding Interaction of an Ethidium Homodimer and an Acridine Ethidium Heterodimer. Biochemistry, vol. 17, No. 24, 1978, pp. 5078-5088.
Gerlach, et al. Annalen Dr Physik, G Folge, Band 2, 1948, pp. 55-75.
Gong, et al., New DNA Minor-Groove Binding Molecules with High Sequence-Selectivities and Binding Affinities, Biochemical and Biophysical Communications, vol. 240, No. 3, 1997, pp. 557-560.
Guo, et al. DNA-Dye Fluorescence Enhancement Based on Shifting the Dimer-Monomer Equilibrium of Fluorescent Dye, Applied Spectroscopy, vol. 51, No. 7, 1997, pp. 1002-1007.
Hartwig, et al. Room-Temperature Palladium-Catalyzed Amination of Aryl Bromides and Chlorides and Extended Scope of Aromatic C—N. Bond Formation with a Commercial Ligand. J. Org. Chem., vol. 64, 1999, pp. 5575-5580.
Haugland. Handbook of Fluorescent Probes and Research Products—Ninth Edition: Nucleic Acid Detection and Genomics Technology. Molecular Probes, Chapter 8, 2002, pp. 265-352.
Higuchi, et al. Simultaneous Amplification and Detection of Specific DNA Sequences. Bio/Technology, vol. 10, Apr. 1992, pp. 413-417.
Holland, et al. Detection of Specific Polymerase Chain Reaction Product by Utilizing the 5' → 3' Exonuclease Activity of Thermus Aquaticus DNA Polymerase. Proc. Natl. Acad. Sci. USA, vol. 88, Aug. 1991, pp. 7276-7280.
Ishiguro, et al. Fluorescence Detection of Specific Sequence of Nucleic Acids by Oxazole Yellow-Linked Oligonucleotides. Homogeneous Quantitative Monitoring of in vitro Transcription. Nucleic Acids Research, vol. 24, No. 24, 1996, pp. 4992-4997.
Jackobsen, et al. Site selective bis-intercalation of a homodimeric thiazole orange dye in DNA oligonucleotides. Nucleic Acids Res. 1995; 23(5):753-60.
Joseph, et al. Tuning of Intercalation and Electron-Transfer Processes Between DNA and Acridinium Derivatives through Steric Effects. Bioconjugate Chem., vol. 15, 2004, pp. 1230-1235.
Kapuscinski, et al. Fluorescent Complexes of DNA with DAPI 4',6-diamidine-2- phenyl indole.2HCI or DCI 4',6-dicarboxyamide-2-phenyl indole. Nucleic Acid Research, vol. 5, No. 10, Oct. 1978, pp. 3775-3799.
Karsai, et al. Evaluation of a Homemade SYBR Green I Reaction Mixture for Real-Time PCR Quantification of Gene Expression. Biotechniques, Apr. 2002; 32(4): 790-2, 794-6.
Khairutdinov, et al. Photophysics of Cyanine Dyes: Subnanosecond Relaxation Dynamics in Monomers, Dimers, and H- and J-Aggregates in Solution. J. Phys. Chem. B, vol. 101, No. 14, 1997, pp. 2602-2610.
Latt, et al. Spectral Studies on 33258 HOECHST and Related Bisbenzimidazole Dyes Useful for Fluorescent Detection of Deoxyribonucleic Acid Synthesis. The Journal of Histochemistry and Cytochemistry, vol. 24, No. 1, 1976, pp. 24-33.
Lee, et al. Allelic Discrimination by Nick-Translation PCR with Fluorogenic Probes. Nucleic Acids Research, vol. 21, No. 16, 1993, pp. 3761-3766.
Lown, et al. Efficient Total Syntheses of the Oligopeptide Antibiotics Netropsin and Distamycin. J. Org. Chem., vol. 50, No. 20, 1985, pp. 3774-3779.

(56) References Cited

OTHER PUBLICATIONS

McCann, et al. Detection of Carcinogens as Mutagens in the *Salmonella*/Microsome Test: Assay of 300 Chemicals. Proc. Nat. Acad. Sci. USA, No. 12, Dec. 1975, pp. 5135-5139.
Nath, et al., "Effects of Ethidium Bromide and SYBR Green I on Different Polymerase Chain Reaction Systems," Journal of Biochemical and Biophysical Methods, vol. 42, 2000, pp. 15-29.
Notification of transmittal of the international search report and the written opinion of the international searching authority, International Application No. PCT/US06/09910, mailed Mar. 29, 2007, 6 pages.
Office action dated Feb. 23, 2012 for U.S. Appl. No. 12/820,983.
Office action dated Jun. 20, 2013 for U.S. Appl. No. 13/541,313.
Office action dated Jul. 11, 2008 for U.S. Appl. No. 11/377,254.
Office action dated Aug. 9, 2011 for U.S. Appl. No. 12/854,436.
Office action dated Sep. 14, 2012 for U.S. Appl. No. 12/820,983.
Office action dated Sep. 29, 2009 for U.S. Appl. No. 11/377,253.
Office action dated Oct. 9, 2013 for U.S. Appl. No. 12/976,917.
Otto, et al. A Comparative Study of DAPI, DIPI, and HOECHST 33258 and 33342 As Chromosomal DNA Stains, Stain Technology, vol. 60, No. 1, 1985, pp. 7-11.
Parks, et al. Optimization of the Hairpin Polyamide Design for Recognition of the Minor Groove of DNA. J. Am. Chem. Soc., vol. 118, No. 26, 1996, pp. 6147-6152.
Perera. PCR Based Detection of Mycobacterium Tuberculosis: Effect of Sample Preparation. Southeast Asian J. Trop. Med Public Health, vol. 25, No. 4, Dec. 1994, pp. 693-697.
Rohatgi, et al. Thermodynamics of Dye Dimerization. Chemical Physics Letters, vol. 12, No. 2, Dec. 15, 1971, pp. 259-260.
Rohatgi, et al. Nature of Bonding in Dye Aggregates. The Journal of Physical Chemistry, vol. 70, No. 6, Jun. 1966, pp. 1695-1701.
Rye, et al. Stable fluorescent complexes of double-stranded DNA with bis-intercalating asymmetric cyanine dyes: properties and applications. Nucleic Acids Res. 1992; 20(11):2803-12.
Saiki, et al. Enzymatic Amplification of β-Globin Genomic Sequences and Restriction Site Analysis for Diagnosis of Sickle Cell Anemia. Science, vol. 230, Dec. 20, 1985, pp. 1350-1354.
Septinus, et al. Hydrophobic Acridine Dyes for Fluorescence Staining of Mitochondria in Living Cells: 1. Thermodynamic and Spectroscopic Properties of 10-n-Alkyl-Acridinium-Orange-Chlorides, Histochemistry, vol. 79, 1983, pp. 443-456.
Stryer, et al. Energy Transfer: A Spectroscopic Ruler. Proceedings of the National Academy of Sciences of the United States of America, vol. 58, No. 2, Aug. 15, 1967, pp. 719-726.
Sumner. Chromosome Banding and Identification. Methods in Molecular Biology: Chromosome Analysis Protocols, vol. 29, 1994, pp. 83-96.
Traganos, et al. Simultaneous Staining of Ribonucleic and Deoxyribonucleic Acids in Unfixed Cells Using Acridine Orange in a Flow Cytofluorometric System. www.jhc.org/cgi/content/abstract/25/1/46, 1 page. Accessed Mar. 2, 2005.
Tse, et al. A Fluorescent Intercalator Displacement Assay for Establishing DNA Binding Selectivity and Affinity. Accounts of Chemical Research, vol. 37, No. 1, 2004, pp. 61-69.
Ueda, et al. Single-Molecule Analysis of Chemotactic Signaling in Dictyostelium Cells. Science, vol. 294, Oct. 26, 2001, pp. 864-867.
Waring. Complex Formation Between Ethidium Bromide and Nucleic Acids. J. Mol. Biol., vol. 13, 1965, pp. 269-282.
West, et al. The Dimeric State of Cyanine Dyes. The Journal of Physical Chemistry, vol. 69, No. 6, Jun. 1965, pp. 1894-1903.
Wirth, et al. Interactions between DNA and mono-, bis-, tris-, tetrakis-, and hexakis(aminoacridines). A linear and circular dichroism, electric orientation relaxation, viscometry, and equilibrium study. J. Am. Chem. Soc. 1988; 110 (3):932-939.
Wittwer, et al. Continuous Fluorescence Monitoring of Rapid Cycle DNA Amplification. BioTechniques, vol. 22, No. 1, Jan. 1997, pp. 130-138.
Wolfe, et al. Simple, Efficient Catalyst System for the Palladium-Catalyzed Amination of Aryl Chlorides, Bromides, and Triflates, J. Org. Chem., vol. 65, 2000, pp. 1158-1174.
Yamagishi et al. Selective Activation of Reactant Molecules by Reversed Micelles. J. Phys. Chem., vol. 85, No. 3, 1981, pp. 281-285.
Yang, et al. Palladium-Catalyzed Amination of Aryl Halides and Sulfonates, Journal of Organometallic Chemistry, vol. 576, 1999, pp. 125-146.
Yarmoluk, et al. Interaction of cyanine dyes with nucleic acids— XXVII: synthesis and spectral properties of novel homodi- and homotrimeric monomethine cyanine dyes . Dyes and Pigments. 2001; 50:21-28.
Yunjing, et al. Study on Acridine Orange Dimer as a New Fluorescent Probe for the Determination of Protein. Anal. Commun., vol. 36, 1999, pp. 135-137.
Zimmerman, et al. Topologically constrained bifunctional intercalators: DNA intercalation by a macrocyclic bisacridine. J. Am. Chem. Soc. 1989; 111 (17):6805-6809.
Zipper, et al. Investigations on DNA Intercalation and Surface Binding by SYBR Green 1, Its Structure Determination and Methodological Implications. Nucleic Acid Research, vol. 32, No. 12, 2004, pp. 1-10.

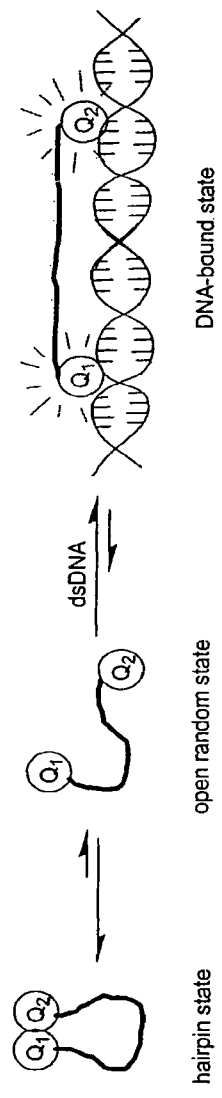
FIG. 1 DNA binding via a release-on-demand mechanism

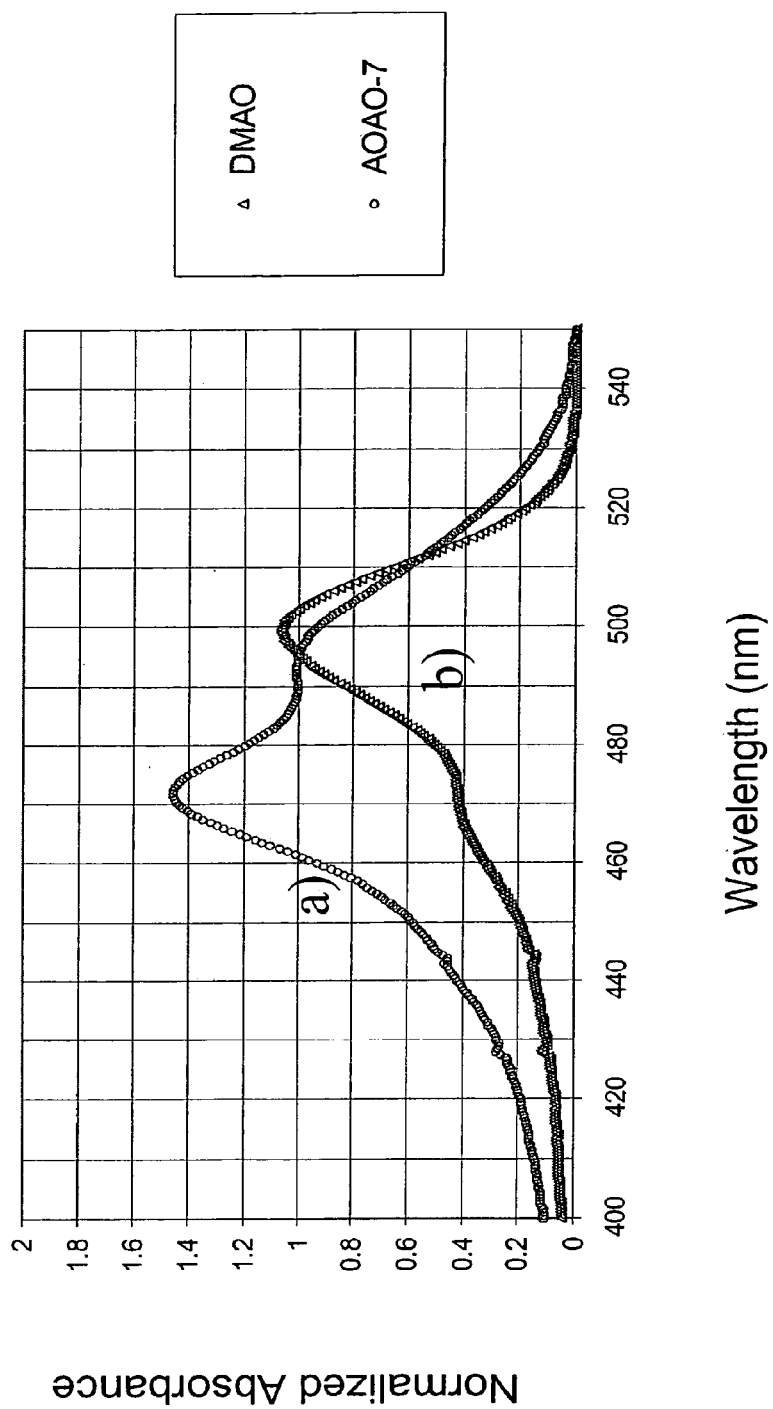
FIG. 2 Normalized absorbance spectra of DMAO and AOAO-7

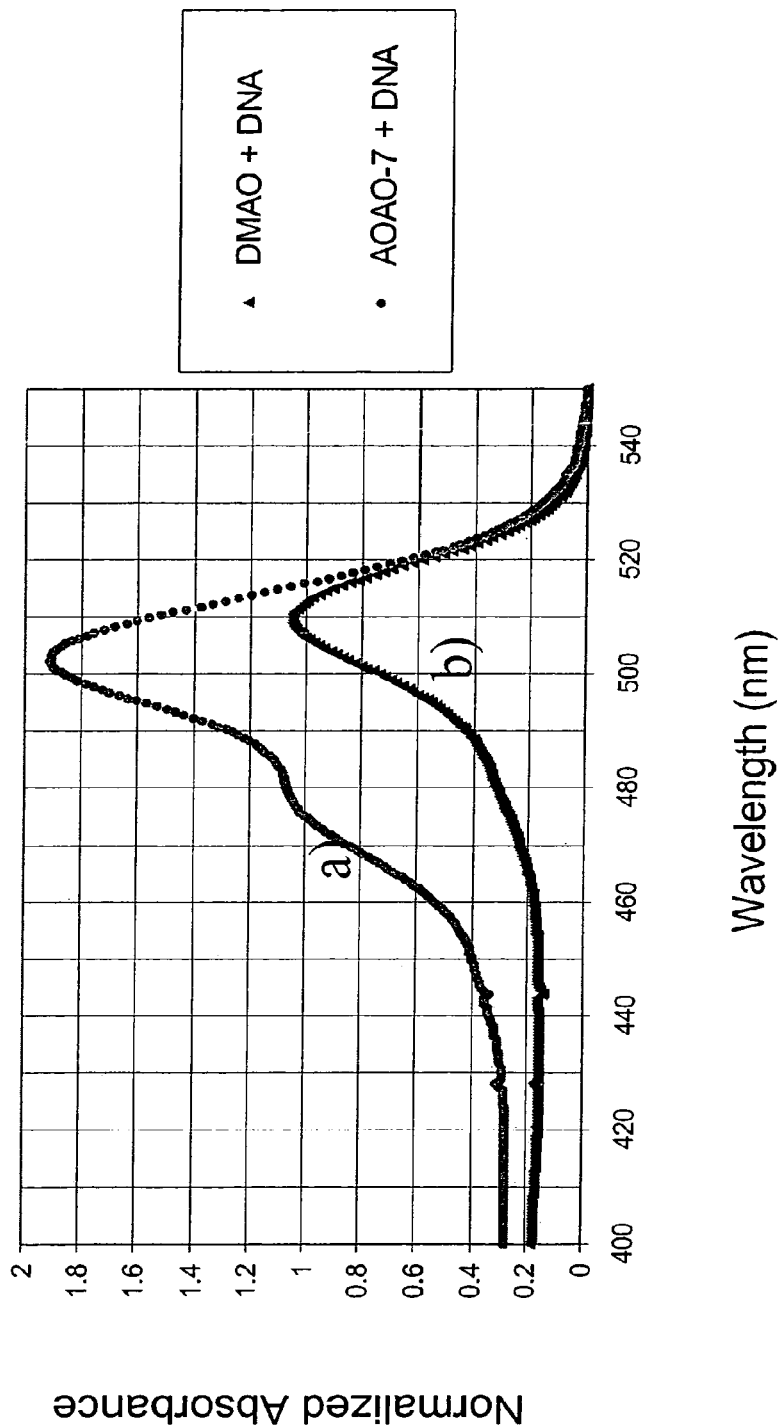
FIG. 3 Normalized absorbance spectra of DMAO and AOAO-7 in the presence of DNA

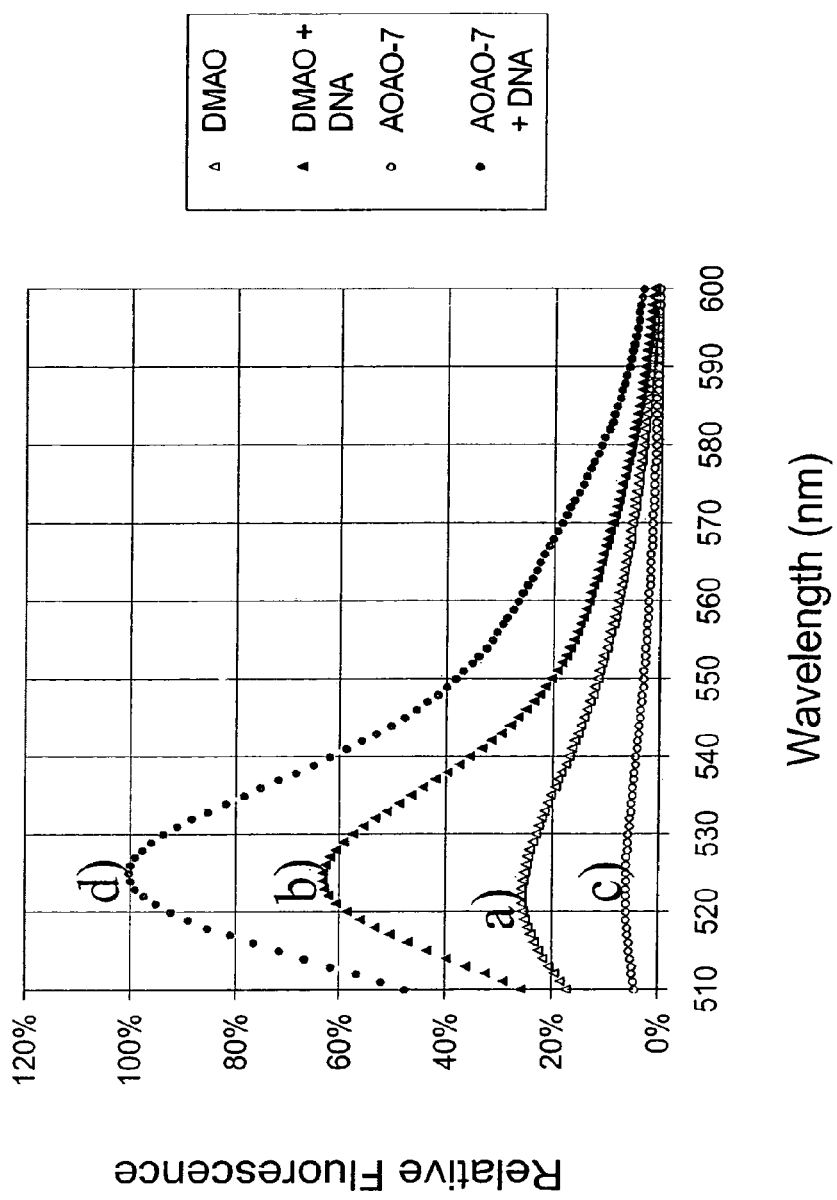
FIG. 4 Relative fluorescence spectra of DMAO and AOAO-7

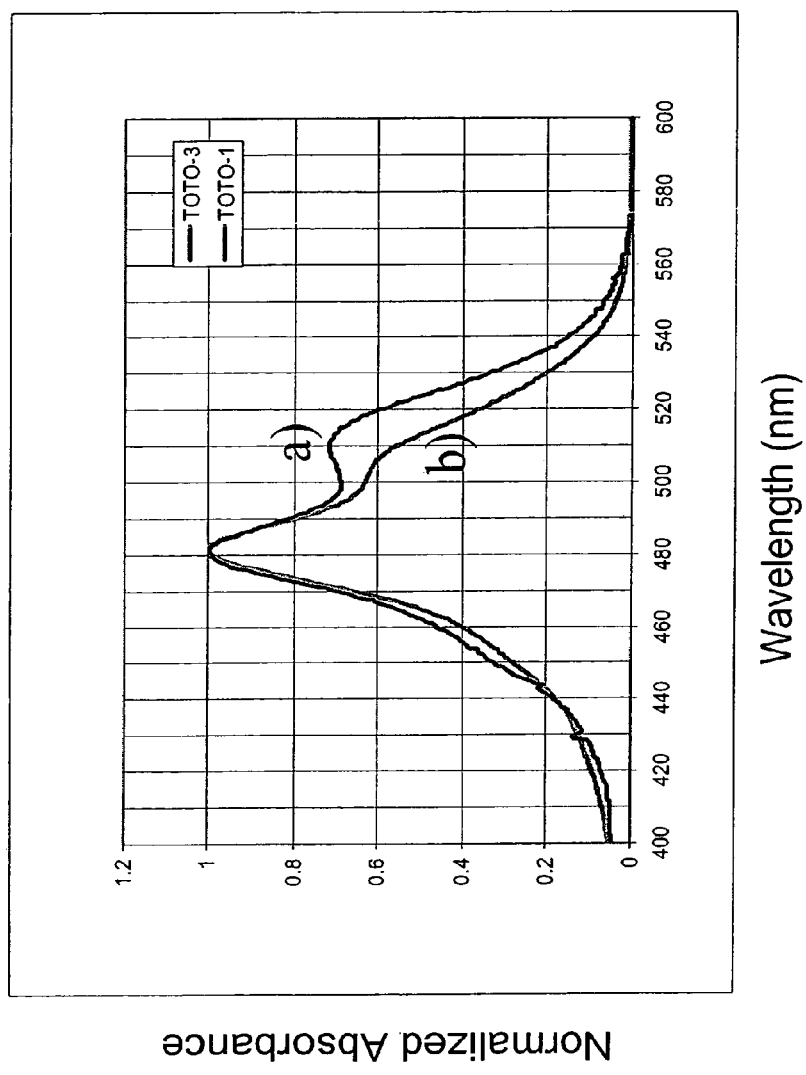
FIG. 5 Normalized absorbance spectra of TOTO-1 and TOTO-3

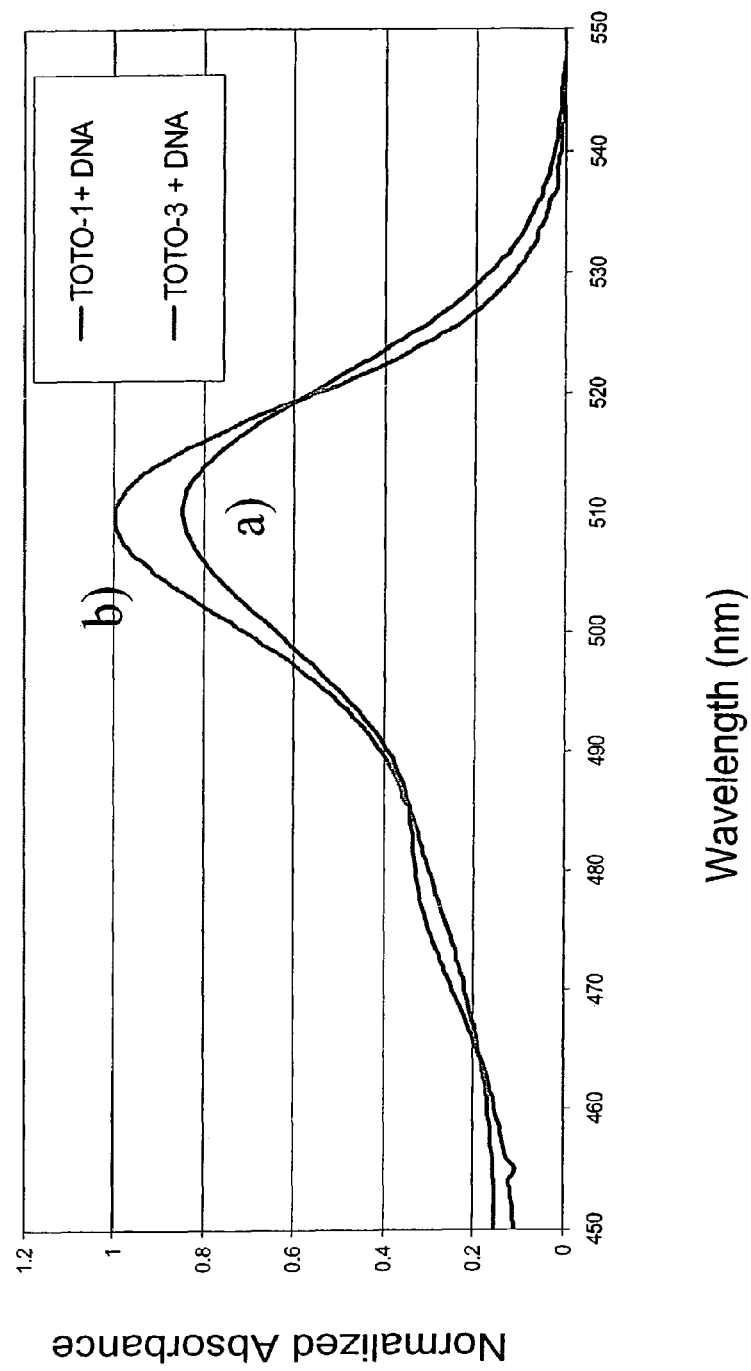
FIG. 6 Absorbance spectra of TOTO-1 and TOTO-3 in the presence of DNA

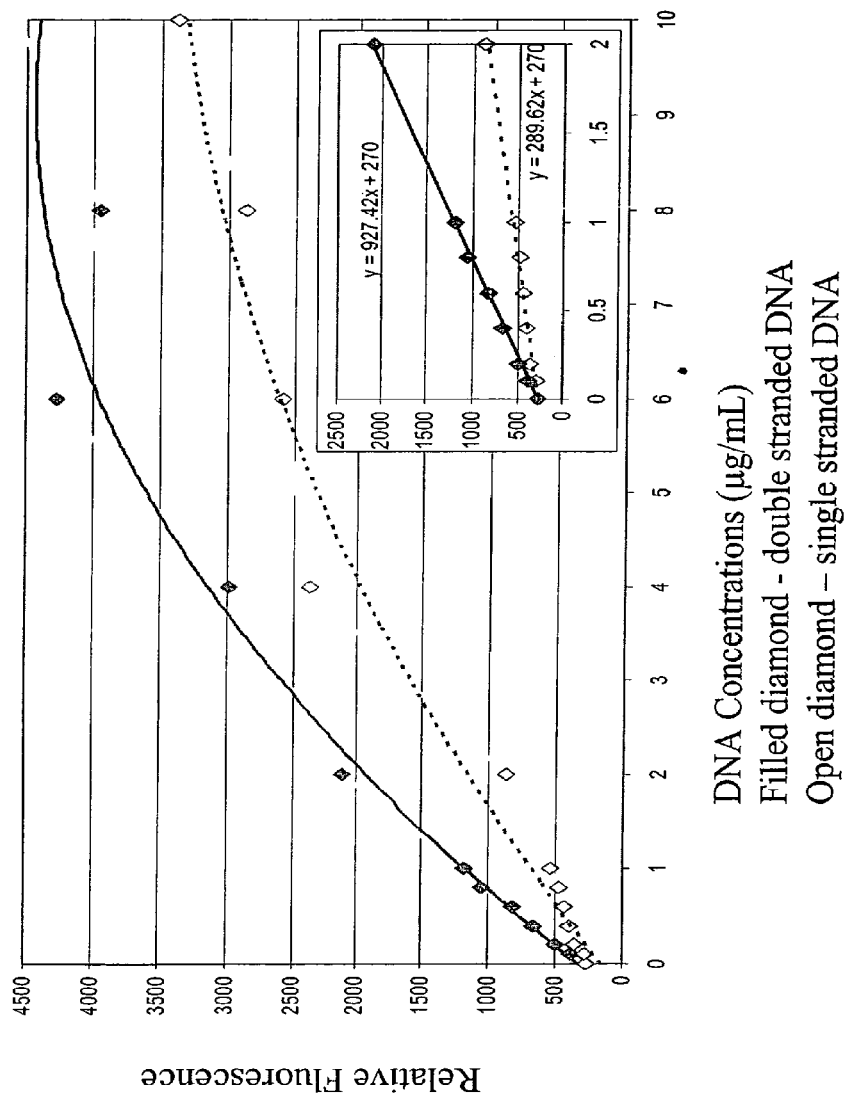
FIG. 7 Fluorescence response curve of AOAO-12 to DNA
DNA Concentrations (μg/mL)
Filled diamond - double stranded DNA
Open diamond – single stranded DNA

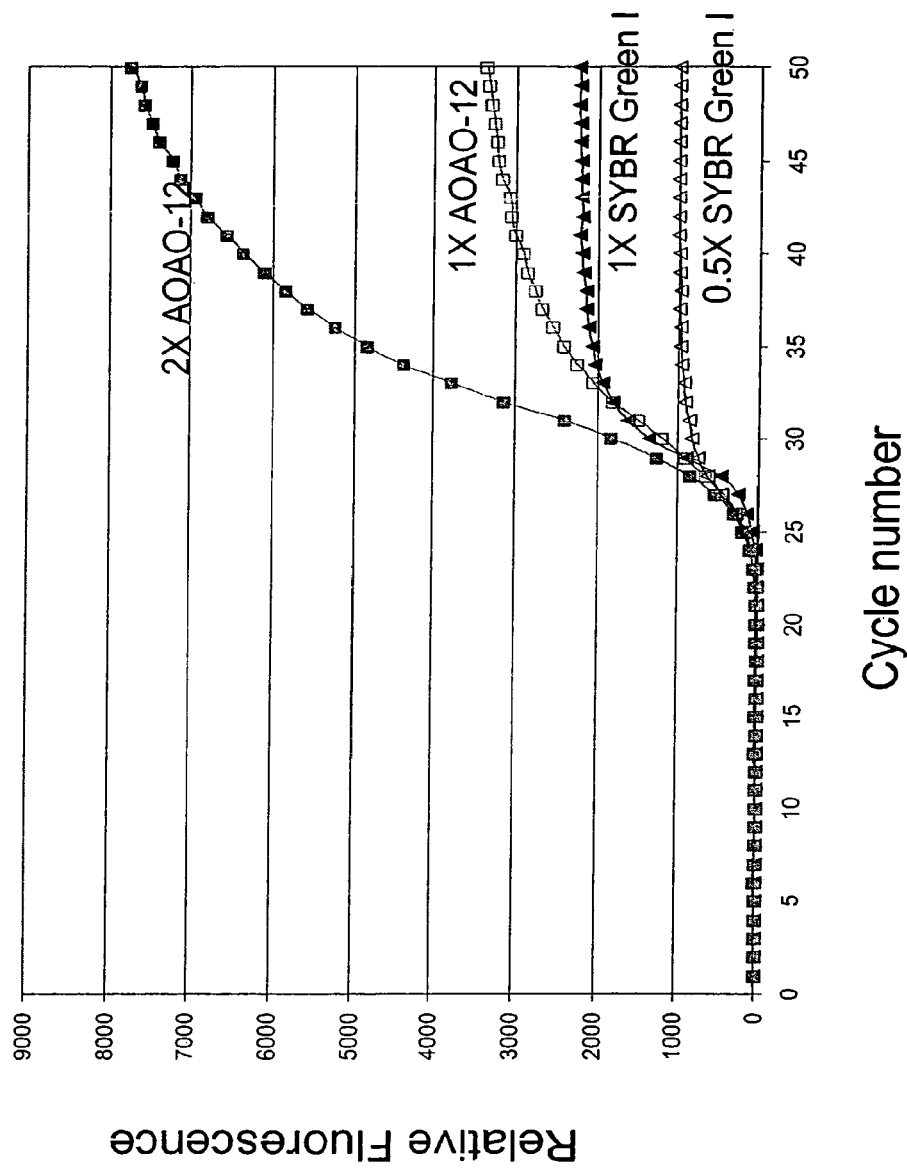
FIG. 8 AOAO-12 or SYBR Green I in qPCR

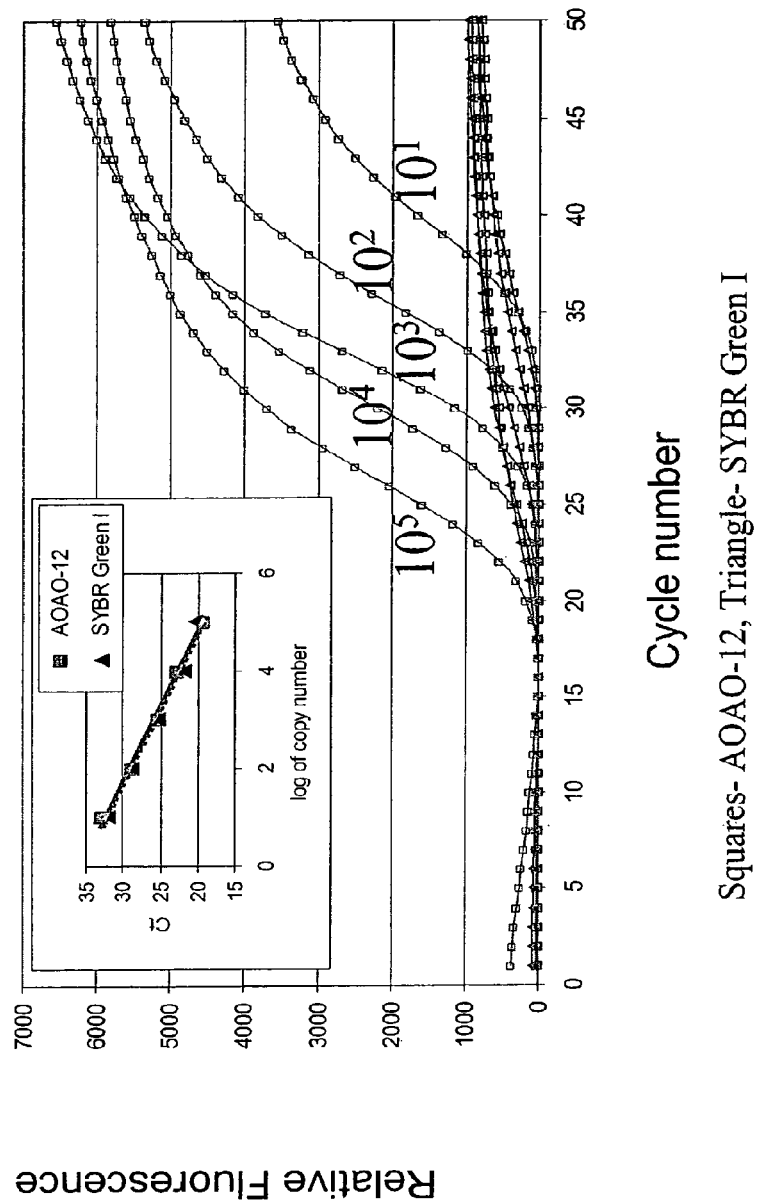
FIG. 9 Comparing AOAO-12 and SYBR Green I in amplification a fragment from human genomic DNA

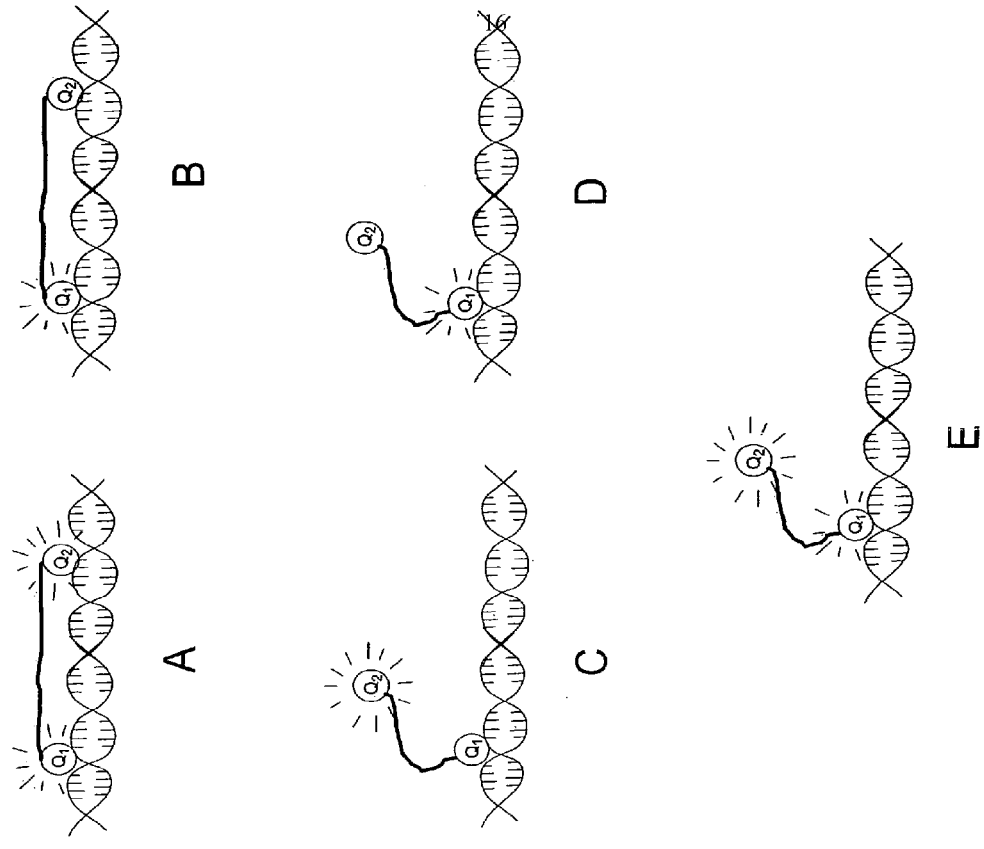
FIG. 10 Possible combinations of monomeric dyes $Q_1$ and $Q_2$ to form a dimeric dye of the invention

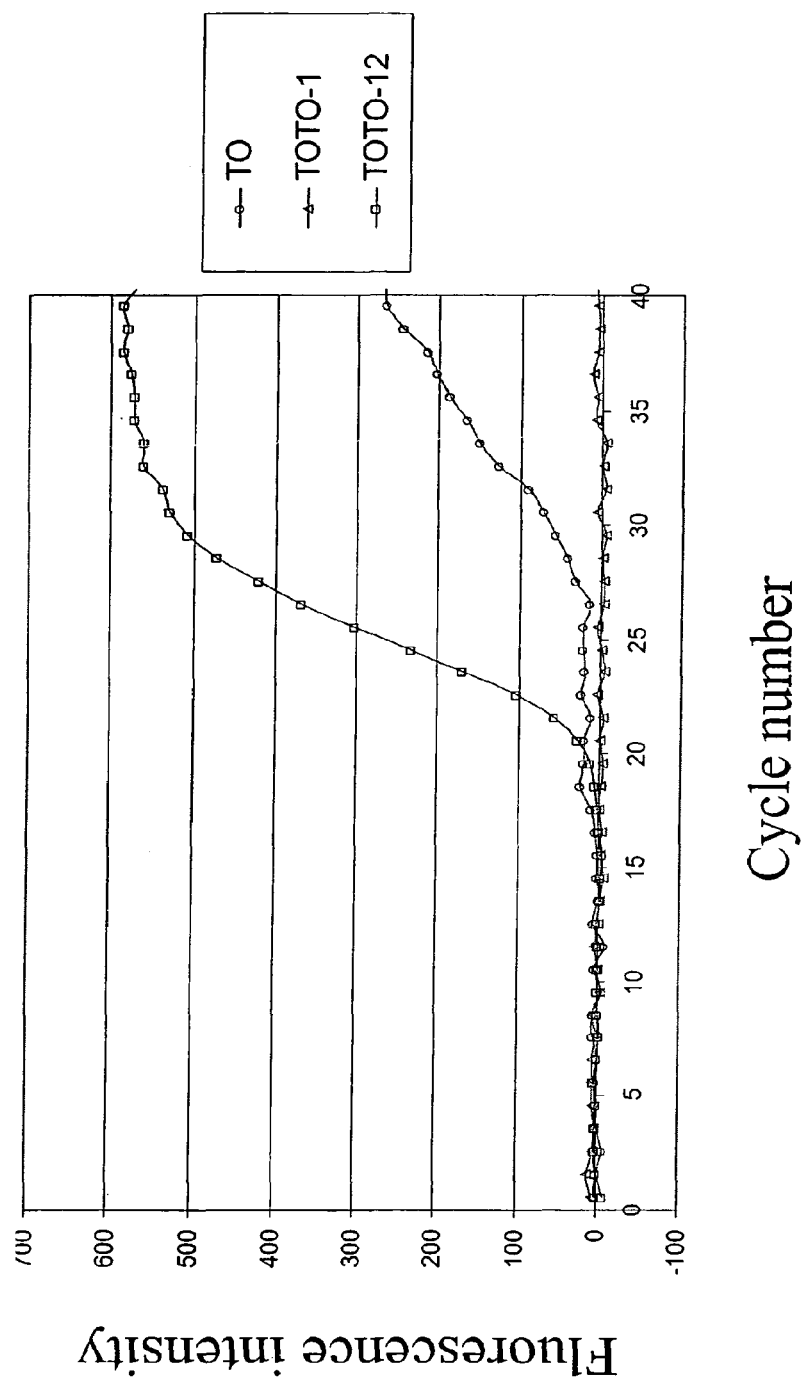
FIG. 11 TO, TOTO-1 and TOTO-12 in qPCR

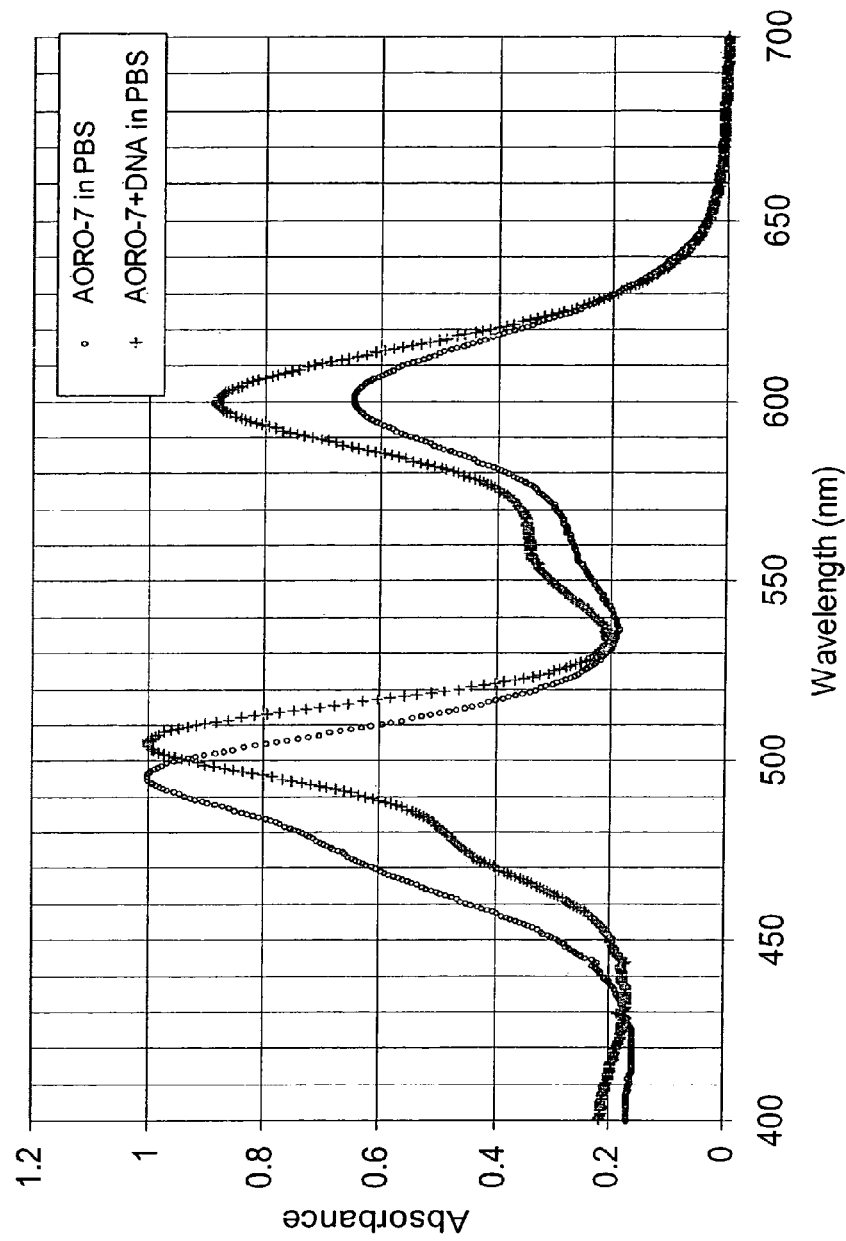
FIG. 12 Spectra of AORO-7 in the absence and presence of DNA in PBS

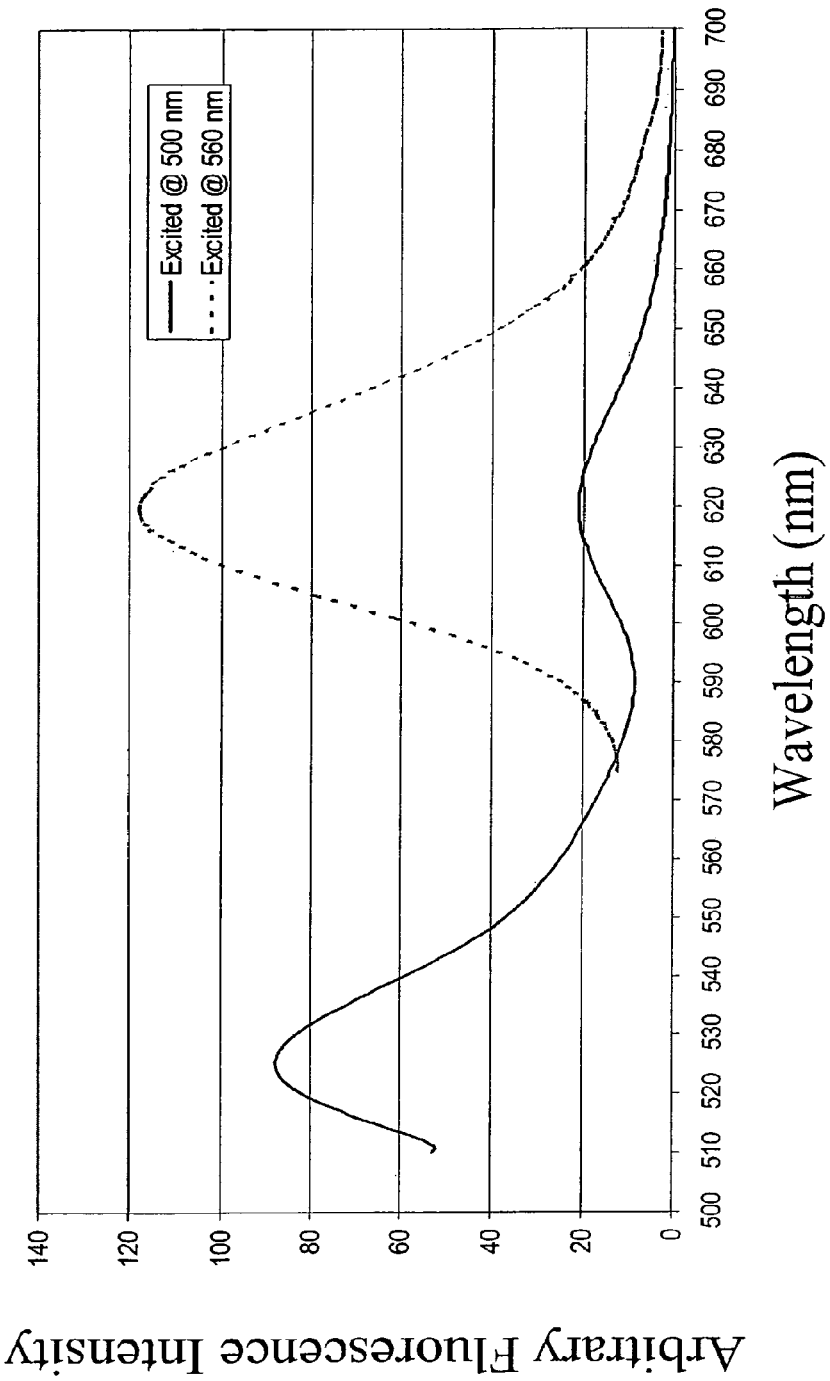
FIG. 13 Emission spectra of AORO-7 in the presence of DNA in PBS

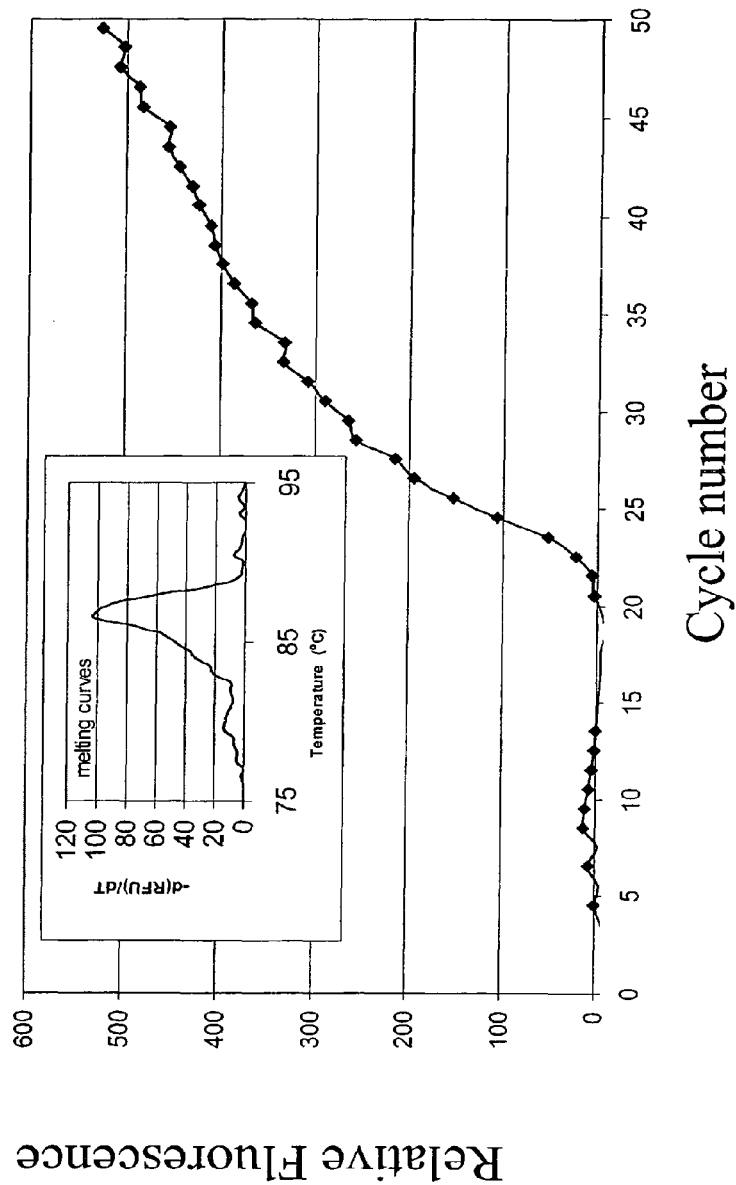
FIG. 14 Amplification of ATPB monitored by AORO-7 (excited at 570nm, monitored at 630 nm)

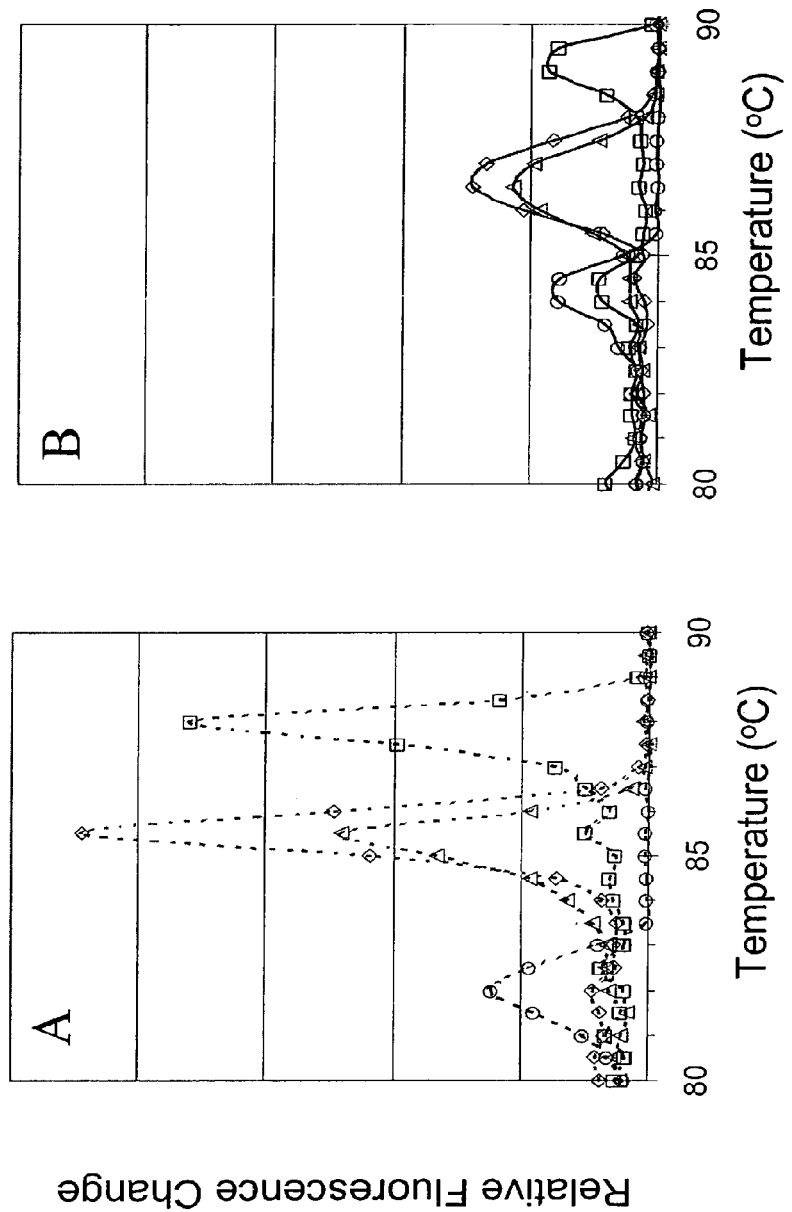
FIG. 15 Melting peaks monitored with AOAO-12 and SYBR Green I
Dash lines- AOAO-12, Solid lines- SYBR Green I
Circles: TBP, Triangles: SDHA, Diamond: RPL4, Square: HMBS

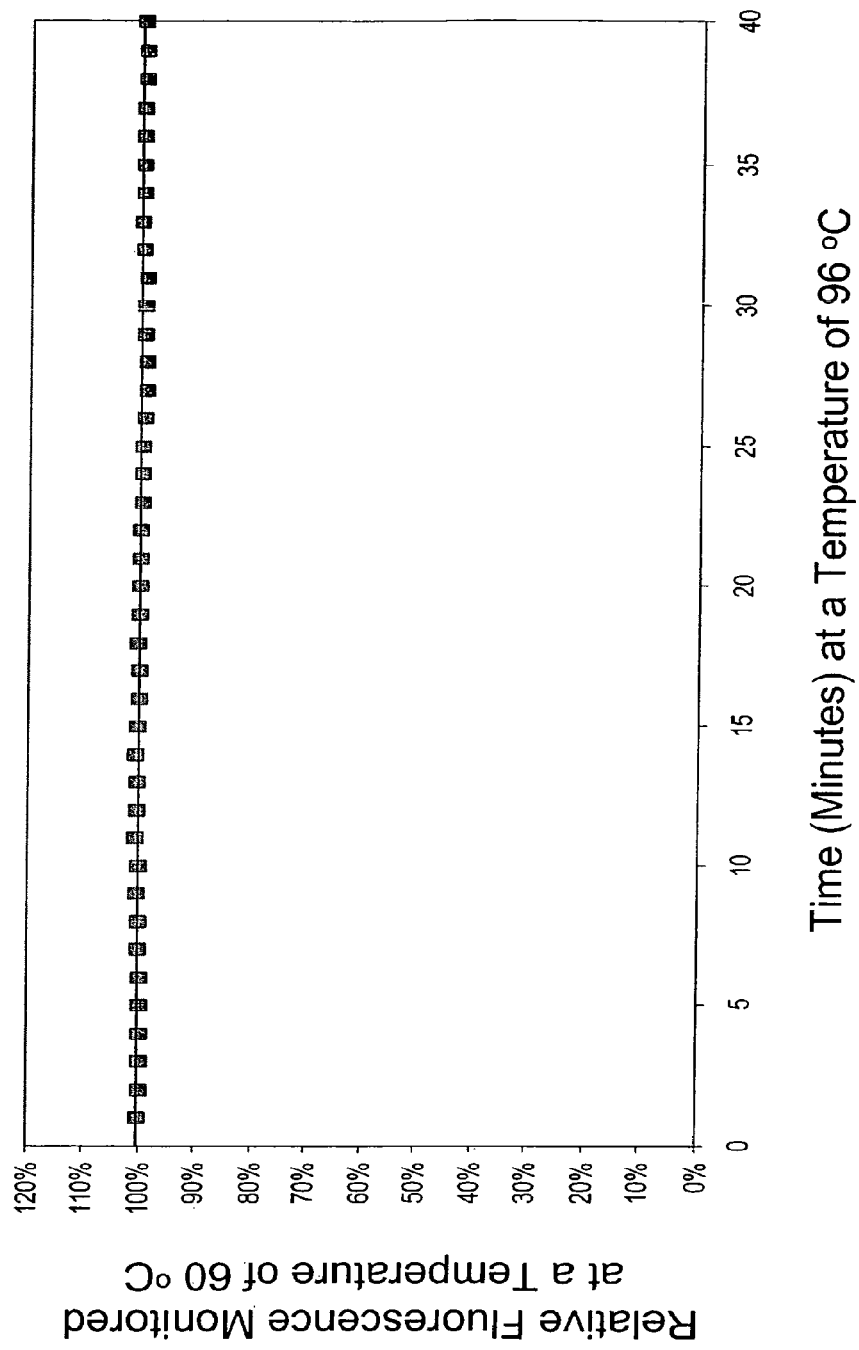
FIG. 16 Stability of AOAO-12 at a temperature of 96 °C

DYES AND LABELED MOLECULES

CROSS-REFERENCE TO RELATED APPLICATIONS

This application is a Continuation application to U.S. application Ser. No. 12/820,983, filed Jun. 22, 2010, which is a Continuation application and claims priority to U.S. application Ser. No. 11/377,253, filed Mar. 16, 2006, now U.S. Pat. No. 7,776,567, issued Aug. 17, 2010, which claims the benefit of U.S. Provisional Application No. 60/663,613, filed on Mar. 17, 2005, the entire contents of which are incorporated herein in their entirety by this reference.

STATEMENT REGARDING NAMES OF PARTIES TO A JOINT RESEARCH AGREEMENT

Biotium, Inc. (Hayward, Calif. (CA)) and AlleLogic Biosciences Corp. (Hayward, Calif.) are parties to a joint research agreement pertaining to the present invention.

REFERENCE TO A SEQUENCE LISTING AND REQUEST AND INCORPORATION BY REFERENCE CONCERNING SAME

An original ASCII diskette and another ASCII diskette, which was a duplicate of the original diskette, containing the Sequence Listing for SEQ ID NO: 1 through SEQ ID NO: 10 disclosed herein, as well as a paper copy of the Sequence Listing, were submitted in, referred to in, and incorporated in their entireties, including the contents thereof, by reference in, the aforementioned U.S. Provisional Application No. 60/663,613. A paper copy of the Sequence Listing is submitted herewith. It is hereby requested that the compliant computer readable Sequence Listing that is already on file for the aforementioned U.S. Provisional Application No. 60/663,613 be used in connection with this application. The paper or compact disc copy of the Sequence Listing in this application, and the content thereof, are identical to the computer readable copy of the Sequence Listing that was filed for the aforementioned U.S. Provisional Application No. 60/663,613. The Sequence Listing, the paper copy of the Sequence Listing that is submitted herewith, and the computer readable Sequence Listing that is already on file for the aforementioned U.S. Provisional Application No. 60/663,613 are hereby incorporated herein, in their entireties, including the contents thereof, by this reference.

The instant application contains a Sequence Listing which has been submitted electronically in ASCII format and is hereby incorporated by reference in its entirety. Said ASCII copy, created on Dec. 1, 2016, is named 35993-701_305_SL.txt and is 3,374 bytes in size.

BACKGROUND

Fluorescent dyes have been used for the detection and analysis of biological samples. As fluorescent dyes are highly sensitive, they can be used to detect a very small number of fluorescent molecules. For example, such fluorescent dyes can be used to detect fewer than 50 fluorescent molecules that are associated with cells. Barak, et al., *J. Cell Biol.* 90, 595 (1981).

Fluorescent dyes may be used as probes for use in imaging in live cells or tissue samples. For example, a fluorescent-dye probe bound to a receptor on the surface of *Dictyostelium* cells has been used in the imaging of a single molecule of fluorescently labeled cAMP. Ueda, et al., *Science* 294, 864 (2001). Several fluorescent probes having different fluorescent wavelengths may be used to perform multi-color imaging in live cells or tissue samples. Fluorescent probes are highly sensitive, of relatively low toxicity, and easy to dispose of relative to radioactive probes.

Fluorescent dyes can be used in the detection of nucleic acids, including DNA and RNA, and biological samples involving nucleic acids. Nucleic acid polymers such as DNA and RNA are involved in the transmission of genetic information from one generation to the next and to the routine functioning of living organisms. Nucleic acids are thus of interest and the objects of study. Fluorescent nucleic acid dyes that specifically bind to nucleic acids and form highly fluorescent complexes are useful tools for such study. These dyes can be used to detect the presence and quantities of DNA and RNA in a variety of media, including pure solutions, cell extracts, electrophoretic gels, micro-array chips, live or fixed cells, dead cells, and environmental samples. These dyes can be used in the quantitative detection of DNA in real-time polymerase chain reaction (qPCR), which is a technique used in genomic research and medical diagnosis.

Polymerase chain reaction (PCR) is a primer extension reaction that provides a method for amplifying specific nucleic acids in vitro. Generally, in PCR, the reaction solution is maintained for a short period at each of three temperatures, 96° C., 60° C. and 72° C., to allow strand separation or denaturation, annealing, and chain extension, respectively. These three temperature stages are repeated for 30 or 40 cycles with the use of an automated thermo-cycler that can heat or cool the tube containing the reaction mixture very rapidly. By repeating the PCR cycle, a million-fold copies of a DNA sample can be produced in a single enzymatic reaction mixture within a matter of hours, enabling researchers to determine the size and sequence of target DNA. This DNA amplification technique has been used for cloning and other molecular biological manipulations. Further discussion of PCR is provided in Mullis, et al., *Methods Enzymol.* (1987), and Saiki, et al., *Science* (1985).

One PCR-based technique that is useful is quantitative real-time PCR (qPCR). Briefly, the mechanism of qPCR is based on PCR amplification of a target DNA in an exponential manner. By running a PCR reaction and measuring the total number of DNA copies at given points during the course of the amplification reaction, one can retroactively calculate the amount of starting DNA material.

Fluorescence-based DNA detection is a generally sensitive, versatile, and convenient detection method that is used in qPCR. There are two types of fluorescent reagents used in qPCR. The first type is based on oligonucleotides labeled with one or more fluorescent dyes, or with a combination of a fluorescent dye and a quencher dye. These labeled oligonucleotides release fluorescence either upon hybridization to a target sequence, or upon cleavage of the oligonucleotides following hybridization in a manner proportional to the amount of DNA present. The mechanism and the use of the oligo-based fluorescent reagents have been described in various patents and publications. See, for example, Holland, et al., *Proc. Natl. Acad. Sci. USA* (1991); Lee, et al., *Nucleic Acids Res.* (1993); and U.S. Pat. Nos. 5,210,015, 5,538,848, 6,258,569, 5,691,146, 5,925,517, 5,118,801, 5,312,728, and 6,635,427. Although oligo-based fluorescent reagents for qPCR have the advantage of being highly specific toward a target sequence, they are very complex in design and consequently expensive to use. The second type of fluorescent reagents used in qPCR is based on DNA-binding fluorescent dyes, which are commonly referred to as fluorescent nucleic acid dyes or stains. Because fluorescent nucleic acid dyes are relatively simple molecules, they are easy to manufacture and thus inexpensive to use. Their application in qPCR is useful for routine genetic detection in research labs.

Not all commonly available fluorescent nucleic acid stains can be used for qPCR. Ideally, a fluorescent nucleic acid dye should meet certain criteria for it to be suitable for qPCR use. First, it should be chemically stable during PCR and storage. Since PCR is carried out at high temperature, the dye should be thermo-stable. Additionally, since the pH of the Tris buffer used for PCR can vary considerably from alkaline (pH 8.5) at low temperature (4° C.) to neutral or slightly acidic at high temperature, the dye should be resistant to acid- or base-assisted decomposition. Second, the dye, when present in the PCR solution, should not inhibit the PCR process. Third, the dye should be non-fluorescent or minimally fluorescent in the absence of DNA, and should become highly fluorescent in the presence of DNA. Fourth, the dye should have absorption and emission wavelengths that are compatible with existing instruments, which are normally equipped with optical channels optimized for common fluorescent dyes, such as FAM, JOE, VIC (Applied Biosystems, Foster City, Calif.), TAMRA, ROX, Texas Red, Cy3, and Cy5, for example. Fifth, the dye should bind with DNA with little or no sequence preference. Sixth, the DNA-dye complexes should have fluorescence intensities that are linearly related to the amount of DNA present.

Given the foregoing criteria, it is not surprising that very few nucleic acid-binding dyes can be used for qPCR. Ethidium bromide (EB) is a DNA dye that has been used to demonstrate the feasibility of using a simple dye for qPCR. Higuchi, et al., *Bio-Technol.* 10(4), 413 (1992). However, EB suffers from problems of low sensitivity and undesirable wavelengths. A widely used dye for qPCR is SYBR Green I from Molecular Probes, Inc. (Eugene, Oreg. (OR)). Wittwer, et al., *Biotechniques* 22(1), 130 (1997). SYBR Green I is a cyclically substituted asymmetric cyanine dye. Zipper, et al., *Nucleic Acids Res.* 32(12), e103 (2004); and U.S. Pat. Nos. 5,436,134 and 5,658,751. The advantages of SYBR Green I are that it has excitation and emission wavelengths very closely matching those of FAM, with which most of the instruments are compatible, and that it is highly fluorescent when bound to DNA. Recently, a DNA dye called LC Green was used for qPCR, although the structure of the dye was not disclosed. Although the LC Green dye appears to have desirable wavelengths matching the commonly used FAM optical channel in most of the PCR instruments, it is much less sensitive than SYBR Green I. More recently, a DNA minor groove-binder called BEBO and a related dye called BOXTO, both of which are asymmetric cyanine dyes, have been reported for use in qPCR. Bengtsson, et al., *Nucleic Acids Res.* 31(8), e45 (2003); and U.S. Patent Application Publication No. 2004/0132046. Like LC Green, both BEBO and BOXTO significantly lag behind SYBR Green I in terms of sensitivity.

Although SYBR Green I has been widely used DNA dye for qPCR, it still is lacking in several respects. For one, SYBR Green I has an inhibitory effect on the PCR process, which limits the maximum signal strength one can achieve by increasing dye concentration. The fluorescent signal strength of qPCR using SYBR Green I is initially proportional to the dye concentration until the dye concentration reaches a point where the dye starts to inhibit the PCR process significantly. A further increase in dye concentration will actually lower the signal strength or increase the cycle number (Ct) because of reduced DNA amplification. For another, SYBR Green I is chemically unstable under alkaline conditions, such as the alkaline condition of the PCR buffer when stored at low temperature. It has been reported that SYBR Green I stored in Tris buffer at 4° C. decomposes significantly over the course of a few days and that the dye decomposition products are apparently potent inhibitors. Karsai, et al., *BioTechniques* 32(4), 790 (2002). For yet another, SYBR Green I provides only one fluorescence color. Many commercially available fluorescence detection instruments have multiple optical channels (the FAM optical channel and additional other optical channels) and are thus capable of detecting multiple fluorescence colors.

Development of fluorescent dyes or the making or the use thereof is desirable.

SUMMARY

A method of producing or designing a fluorescent dye suitable for useful application, such as in a qPCR process, for example, is provided. The method involves covalently linking two or three monomeric dyes via a bridge that may be flexible and substantially neutral (for example, neutral or slightly charged). A method of producing or designing a dye, as provided herein, may allow for the development of a fluorescent nucleic acid dye that has a wavelength and/or other spectral property that heretofore could not be obtained.

A fluorescent dye suitable for useful application, such as that described above, for example, is provided. A dimeric or trimeric dye, which may be produced according to a method described herein, may form a hairpin structure, which, it is believed, may enable the dye to stain nucleic acids via a release-on-demand mechanism, as further described herein. A dye described herein may have at least one feature or all of the following features: relatively low "fluorescence background" (fluorescence in the absence of nucleic acids), if any, and ideally, no fluorescence background; relatively low PCR inhibition, and ideally, no PCR inhibition; relatively high fluorescent signal strength; and relative high stability. The dye may be better as to at least one of these features, or as to all of these features, than an existing dye, such as SYBR Green I, merely by way of example. A dye described herein may have a property, such as a wavelength and/or another spectral property, for example, that heretofore could not be obtained.

Dimeric and/or trimeric nucleic acid dyes or stains that are capable of intramolecular dimer formation, or the formation of a hairpin structure, are provided. It is believed that a hairpin-shaped dye may non-fluorescent or minimally fluorescent by itself, but may become highly fluorescent in the presence of nucleic acids. It is believed that nucleic acid binding of the dye may occur via an intermediate state wherein the dye forms, in part, an open random conformation. It is further believed that this open random conformation of the dye may exist in a small quantity and in equilibrium with the hairpin state. It is believed that as the amount of nucleic acids increases, an equilibrium shift from the hairpin state toward the nucleic acid-bound state of the dye may occur, such that the strength of the resulting fluorescence signal may be substantially linearly proportional to the amount of nucleic acids present.

The above-described mechanism, which may be referred to as a release-on-demand mechanism of DNA staining, may be desirable for various applications, such as quantitative, real-time PCR (qPCR), for example. Merely by way of explanation, it is believed that the formation of the hairpin structure may render the "effective dye concentration" low, such that a dye described herein may interfere very little with the PCR process. Thus, as compared with previous dyes, such as SYBR Green I, for example, a higher concentration of a dye described herein may be used in qPCR. This higher concentration of dye may increase DNA detection sensitivity, perhaps significantly.

A method of determining nucleic acid formation or a lack thereof in a sample is provided. The sample may or may not comprise a target nucleic acid. Such a method may comprise providing a test solution comprising the sample and a fluorescent nucleic acid dye, where the fluorescent nucleic acid dye has the formula:

wherein BRIDGE is a substantially aliphatic, substantially neutral linker comprising from about 8 to about 150 non-hydrogen atoms; $Q_1$ is a dye constituent selected from a fluorescent nucleic acid dye constituent, a non-fluorescent nucleic acid dye constituent, a fluorescent non-nucleic acid dye constituent, and a non-fluorescent non-nucleic acid dye constituent; $Q_2$ is a dye constituent selected from a fluorescent nucleic acid dye constituent, a non-fluorescent nucleic acid dye constituent, a fluorescent non-nucleic acid dye constituent, and a non-fluorescent non-nucleic acid dye constituent. The dye constituents may be any of suitable dye constituents, such as those described herein, for example. Merely by way of example, the fluorescent nucleic acid dye constituent may be selected from an acridine dye, an asymmetric cyanine dye, a symmetric cyanine dye, a phenanthridinium dye, and a pyronin dye, and a styryl dye. At least one dye constituent of the $Q_1$ dye constituent and the $Q_2$ dye constituent is a reporter dye constituent, and at least one dye constituent of the $Q_1$ dye constituent and the $Q_2$ dye constituent is a fluorescent nucleic acid dye constituent or a non-fluorescent nucleic acid dye constituent. The reporter dye constituent and the fluorescent nucleic acid dye constituent may or may not be the same. The method may comprise performing a process using the test solution that would be sufficient for amplification of the target nucleic acid should the sample comprise the target nucleic acid. Merely by way of example, the process may be a PCR process, such as a real-time PCR process, for example. The method may comprise illuminating the test solution with light at a wavelength sufficient for absorption by the reporter dye constituent and determining fluorescent emission or a lack thereof.

Another method of determining nucleic acid formation or a lack thereof in a sample is provided. The sample may or may not comprise a target nucleic acid. Such a method method may comprise providing a test solution comprising the sample and a fluorescent nucleic acid dye, where the fluorescent nucleic acid dye has the formula:

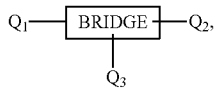

wherein BRIDGE is a substantially aliphatic, substantially neutral linker comprising from about 15 to about 150 non-hydrogen atoms; $Q_1$ is a dye constituent selected from a fluorescent nucleic acid dye constituent, a non-fluorescent nucleic acid dye constituent, a fluorescent non-nucleic acid dye constituent, and a non-fluorescent non-nucleic acid dye constituent; $Q_2$ is a dye constituent selected from a fluorescent nucleic acid dye constituent, a non-fluorescent nucleic acid dye constituent, a fluorescent non-nucleic acid dye constituent, and a non-fluorescent non-nucleic acid dye constituent; $Q_3$ is a dye constituent selected from a fluorescent nucleic acid dye constituent, a non-fluorescent nucleic acid dye constituent, a fluorescent non-nucleic acid dye constituent, and a non-fluorescent non-nucleic acid dye constituent. The dye constituents may be any suitable dye constituents, such as those described herein, for example. Merely by way of example, the fluorescent nucleic acid dye constituent may be selected from an acridine dye, an asymmetric cyanine dye, a symmetric cyanine dye, a phenanthridinium dye, and a pyronin dye, and a styryl dye. At least one dye constituent of the $Q_1$ dye constituent, the $Q_2$ dye constituent, and the $Q_3$ dye constituent is a reporter dye constituent, and at least one dye constituent of the $Q_1$ dye constituent, the $Q_2$ dye constituent, and the $Q_3$ dye constituent is a fluorescent nucleic acid dye constituent or a non-fluorescent nucleic acid dye constituent. The reporter dye constituent and the fluorescent nucleic acid dye constituent may or may not be the same. The method may comprise performing a process using the test solution that would be sufficient for amplification of the target nucleic acid should the sample comprise the target nucleic acid. Merely by way of example, the process may be a PCR process, such as a real-time PCR process, for example. The method may comprise illuminating the test solution with light at a wavelength sufficient for absorption by the reporter dye constituent and determining fluorescent emission or a lack thereof.

In the formulas provided above, BRIDGE may have the formula set forth directly below.

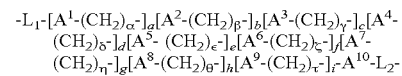

In this formula, each of $L_1$ and $L_2$, independently, is a moiety comprising a single bond; a polymethylene unit having 1 carbon to about 12 carbons, inclusive, optionally comprising at least one hetero atom selected from N, O and S; or an aryl optionally comprising at least one hetero atom selected from N, O and S; each of $A^1$, $A^2$, $A^3$, $A^4$, $A^5$, $A^6$, $A^7$, $A^8$, $A^9$, and $A^{10}$, independently, is a nucleic-acid-binding-enhancing-group (NABEG); a branched alkyl optionally comprising at least one hetero atom selected from N, O and S; or at least one saturated 5- or 6-membered ring, optionally comprising at least one hetero atom selected from N, O and S; each of $\alpha$, $\beta$, $\gamma$, $\delta$, $\epsilon$, $\zeta$, $\eta$, $\theta$, and $\tau$, independently, is zero or an integer from 1 to about 20, inclusive; and each of a, b, c, d, e, f, g, h, and i, independently, is zero or an integer from 1 to about 20, inclusive. BRIDGE may comprise a suitable number of non-hydrogen atoms, such as from about 8 to about 100 or about 150, inclusive, about 12 to about 60, inclusive, or about 15 to about 40, inclusive, merely by way of example. BRIDGE may comprise up to one positive charge, merely by way of example. BRIDGE may be any suitable linker molecule, such as any described herein, for example. In one example, BRIDGE has the formula:

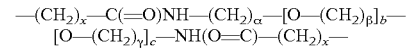

wherein each x, independently, is an integer selected from 1 to 11, inclusive; $\alpha$ is an integer selected from 2 to about 20, inclusive; each of $\beta\square$ and $\gamma$, independently, is 2 or 3; b is zero or an integer from 1 to about 20, inclusive; and c is zero or 1.

Compositions associated with the above-described methods are also provided. Merely by way of example, a dye of any of the structures provided directly below is provided.

acid dye constituent; $Q_2$ is a fluorescent nucleic acid dye constituent; and $R_r$ is a reactive group or a functional group. The reactive group or functional group may be any of

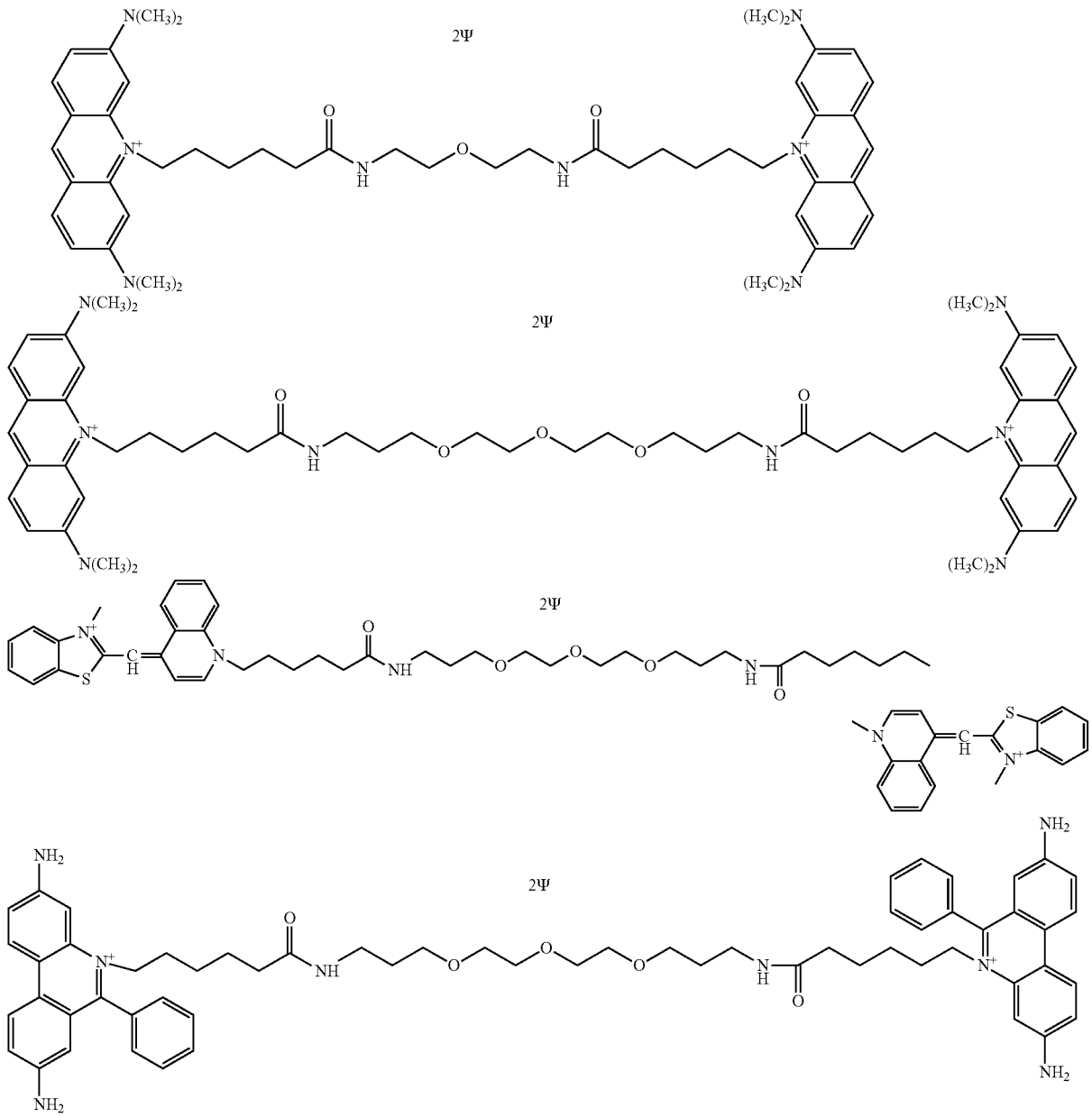

In the dye structures above, Ψ represents an anion, such as a iodide or a chlorine anion, merely by way of example.

A composition having the formula set forth directly below is also provided.

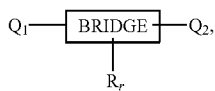

In this formula, BRIDGE is a substantially aliphatic linker comprising from about 15 to about 150 non-hydrogen atoms and up to one positive charge; $Q_1$ is a fluorescent nucleic suitable such groups, such as those described herein, for example. The composition may be any suitable composition, such as any of those described herein, for example. A method of using the composition, or dye, may comprise conjugating the composition to a substrate molecule, such as a substrate molecule selected from a nucleotide, an oligonucleotide, a peptide, a protein, a hapten, a drug, a microparticle, a synthetic polymer, a natural polymer, a biological cell, a virus, and a molecule of a solid surface.

A method of preparing a sample that may or may not comprise nucleic acid is also provided. The method may comprise providing a combination of the sample and a composition, or dye, such as those described herein, wherein if nucleic acid is present in the sample, a nucleic acid-dye complex is formed. The method may further comprise incubating the combination. A method of determining presence or absence of nucleic acid in a sample, is also provided. The method may comprise providing a combination of the sample and a composition, or dye, such as those described herein, wherein if nucleic acid is present in the sample, a nucleic acid-dye complex is formed; illuminating the combination with light at a wavelength sufficient such that if a nucleic acid-complex is formed the light is absorbed thereby; and determining fluorescent emission or a lack thereof. A kit for determining nucleic acid formation or a lack thereof in a sample is also provided. The kit may comprise at least one composition sufficient for amplification of the target nucleic acid in the sample should the sample comprise the target nucleic acid, and a composition, or dye, such as those described herein.

These and various other aspects, features, and embodiments are further described herein.

BRIEF DESCRIPTION OF THE DRAWINGS

A detailed description of various aspects, features and embodiments is provided herein with reference to the accompanying drawings, which are briefly described below. The drawings are illustrative and are not necessarily drawn to scale. The drawings illustrate various aspects or features and may illustrate one or more embodiment(s) or example(s) in whole or in part. A reference numeral, letter, and/or symbol that is used in one drawing to refer to a particular element or feature may be used in another drawing to refer to a like element or feature.

FIG. 1 is a schematic illustration of DNA binding via a release-on-demand mechanism, in which three conformation states of the dye are in substantial equilibrium.

FIG. 2 is a graphical representation of normalized absorbance versus wavelength (nm), or normalized absorption spectra, of a) a dimeric dye, AOAO-7 (○), and b) a monomeric AO dye, DMAO (Δ), in PBS buffer.

FIG. 3 is a graphical representation of normalized absorbance versus wavelength (nm), or normalized absorption spectra, of a) a dimeric dye, AOAO-7 (●), and b) a monomeric AO dye, DMAO (▲), in a buffer and in the presence of DNA.

FIG. 4 is a graphical representation of relative fluorescence versus wavelength (nm), or fluorescence emission spectra, of DMAO (Δ) and AOAO-7 (○) in PBS buffer before DNA addition, a) and c), respectively, and DMAO (▲) and AOAO-7 (●) in PBS buffer after DNA addition, b) and d), respectively.

FIG. 5 is a graphical representation of normalized absorbance versus wavelength (nm), or normalized absorption spectra, of a) TOTO-1 (prepared according to U.S. Pat. No. 5,582,977) (darker line), and b) TOTO-3 (lighter line), in a buffer.

FIG. 6 is a graphical representation of normalized absorbance versus wavelength (nm), or normalized absorption spectra, of a) TOTO-1 according to U.S. Pat. No. 5,582,977 (darker line), and b) TOTO-3 (lighter line), in a buffer and in the presence of DNA.

FIG. 7 includes a graphical representation of relative fluorescence versus DNA concentration (ng/mL), or a titration, of single-stranded DNA (◊), and double-stranded DNA (♦), in solution and in the presence of AOAO-12 (at 0.2 μM). FIG. 7 also includes an inset graphical representation of relative fluorescence versus DNA concentration that shows a substantially linear relationship between the two.

FIG. 8 is a graphical representation of relative fluorescence versus cycle number (Ct), or PCR amplification, using SYBR Green I at a lower dye concentration (Δ) and a higher dye concentration (▲), and AOAO-12 at a lower dye concentration (□) and a higher dye concentration (■), where Ct generally refers to the cycle number at which the fluorescence signal reaches an arbitrary threshold and, in a PCR amplification plot, generally corresponds to where the fluorescence signal just begins to rise from the baseline. For each dye, relative dye concentration was measured in optical density (OD) at the absorption maximum of the dye in PBS buffer, with the dye concentration of 1× and 2×AOAO-12 at 471 nm corresponding to an OD of 0.1 and 0.2, respectively, and the dye concentration of 0.5× and 1×SYBR Green I at 495 nm corresponding to an OD of 0.025 and 0.05, respectively.

FIG. 9 includes a graphical representation of relative fluorescence versus cycle number (Ct), or PCR amplification, using AOAO-12 (□), and SYBR Green I (Δ), as the fluorescent probe, each at optimal concentrations. For each dye, relative dye concentration was measured in optical density (OD) at the absorption maximum of the dye in PBS buffer, with the dye concentration of AOAO-12 at 471 nm corresponding to an OD of 0.4 and the dye concentration of SYBR Green I at 495 nm corresponding to an OD of 0.025. FIG. 9 also includes an inset graphical representation of Ct versus log of DNA sample copy number, using AOAO-12 (■) and SYBR Green I (▲), respectively, that in each case, shows a substantially linear relationship between the two.

FIG. 10 is a schematic illustration of possible combinations A, B, C, D, and E, of monomeric dyes, $Q_1$ and $Q_2$, to form a dimeric dye. Combination A comprises two identical reporter fluorescent nucleic acid dyes or two reporter fluorescent nucleic acid dyes of similar spectra. Combination B comprises one reporter fluorescent nucleic acid dye and one non-reporter DNA-binding molecule. Combination C comprises one non-reporter DNA-binding molecule and one reporter non-DNA-binding dye. Combination D comprises one reporter fluorescent nucleic acid dye and one non-reporter non-fluorescent non-nucleic acid dye. Combination E comprises one reporter fluorescent nucleic acid dye and one reporter fluorescent non-nucleic acid dye.

FIG. 11 is a graphical representation of fluorescence intensity versus cycle number (Ct), or PCR amplification, using TO monomeric dye (○), TOTO-1 monomeric dye (Δ), and TOTO-12 dimeric dye (□) (Compound No. 24, Table 2).

FIG. 12 is a graphical representation of absorbance versus wavelength (nm), or absorption spectra, of heterodimeric dye AORO-7 in PBS buffer (○), and of heterodimeric dye AORO-7 in PBS buffer and in the presence of DNA (+).

FIG. 13 is a graphical representation of arbitrary fluorescence intensity versus wavelength (nm), or emission spectra, of the heterodimeric dye AORO-7, with excitation either at 500 nm (solid, darker line) or at about 560 nm (broken, lighter line), recorded separately.

FIG. 14 includes a graphical representation of relative fluorescence versus cycle number (Ct), or PCR amplification, using the heterodimeric dye AORO-7. FIG. 14 also includes an inset graphical representation, or melting curve plot, of relative fluorescence signal versus temperature (° C.).

FIG. 15 is a graphical representation, or melting curve plot, of relative fluorescence change versus temperature (° C.), A) using AOAO-12 (dashed lines) monitoring, and B) using SYBR Green I (solid lines) monitoring, of four amplicons, TBP (○), SDHA (Δ), RPL4 (◊), and HMBS (□).

FIG. 16 is a graphical representation of relative fluorescence monitored at 60° C. versus minutes at 96° C., or thermo-stability at 96° C., of AOAO-12.

DESCRIPTION

Fluorescent dyes or stains that may be useful in various applications, such as nucleic acid detection, for example, are described herein. Such dyes may be dimeric or trimeric nucleic acid dyes, for example, that have low background fluorescence in the absence of nucleic acids, but become highly fluorescent in the presence of nucleic acids. Dimeric and trimeric nucleic acid dyes may be useful in various applications, such as nucleic acid detection, for example, as described herein. Methods associated with the preparation and use of fluorescent dyes or stains are also described herein, as are useful systems, or kits, that comprise fluorescent dyes or stains.

Herein, it will be understood that a word appearing in the singular encompasses its plural counterpart, and a word appearing in the plural encompasses its singular counterpart, unless implicitly or explicitly understood or stated otherwise. Further, it will be understood that for any given component described herein, any of the possible candidates or alternatives listed for that component, may generally be used individually or in combination with one another, unless implicitly or explicitly understood or stated otherwise. Additionally, it will be understood that any list of such candidates or alternatives, is merely illustrative, not limiting, unless implicitly or explicitly understood or stated otherwise. Still further, it will be understood that any figure or number presented herein is approximate, and that any numerical range includes the minimum number and the maximum number defining the range, whether or not the term "inclusive" or the like appears, unless implicitly or explicitly understood or stated otherwise. Additionally, it will be understood that any permissive, open, or open-ended language encompasses any relatively permissive to restrictive language, open to closed language, or open-ended to closed-ended language, respectively, unless implicitly or explicitly understood or stated otherwise. Merely by way of example, the word "comprising" may encompass "comprising"-, "consisting essentially of"-, and/or "consisting of"-type language.

Various terms are generally described below or used herein to facilitate understanding. It will be understood that a corresponding general description of these various terms applies to corresponding linguistic or grammatical variations or forms of these various terms. It will also be understood that the general description of any term below may not apply or may not fully apply when the term is used in a non-general or more specific manner. It will also be understood that the terminology used or the description provided herein, such as in relation to various embodiments, for example, is not limiting. It will further be understood that embodiments described herein or applications described herein, are not limiting, as such may vary.

Generally, the terms "stain" and "dye" may be used interchangeably and refer to an aromatic molecule capable of absorbing light in the spectral range of from about 250 nm to about 1,200 nm. Generally, the term "dye" may refer to a fluorescent dye, a non-fluorescent dye, or both. Generally, the term "fluorescent dye" refers to a dye capable of emitting light when excited by another light of appropriate wavelength.

Generally, the term "fluorescence quencher" refers to a molecule capable of quenching the fluorescence of another fluorescent molecule. Fluorescence quenching can occur via at least one of the three ways. The first type of fluorescence quenching occurs via fluorescence resonance energy transfer (FRET) (Förster, *Ann. Phys.* (1948); and Stryer, et al., *Proc. Natl. Acad. Sci.* (1967)), wherein a quencher absorbs the emission light from a fluorescent molecule. The absorption peak of a FRET quencher usually has to have significant overlap with the emission peak of a fluorescent dye for the FRET quencher to be an efficient fluorescent quencher. A FRET quencher is typically a non-fluorescent dye, but can also be a fluorescent dye. When a quencher is a fluorescent dye, only the absorption property of the dye is utilized. A second type of fluorescence quenching occurs via photo-induced electron transfer (PET), wherein the quencher is an electron-rich molecule that quenches the fluorescence of a fluorescent molecule by transferring an electron to the electronically excited dye. A third type of fluorescence quenching occurs via dye aggregation, such as H-dimer formation, wherein two or more dye molecules are in physical contact with one another, thereby dissipating the electronic energy into the vibrational modes of the molecules. This type of contact fluorescence quenching can occur between two identical fluorescent dyes, or between two different fluorescent dyes, or between a fluorescent dye and a FRET quencher, or between a fluorescent dye and a PET quencher. Other types of fluorescence quenchers, though not used as commonly, include stable free radical compounds and certain heavy metal complexes.

Generally, the term "nucleic acid" refers to double-stranded DNA (dsDNA), single-stranded DNA (ssDNA), double-stranded RNA (dsRNA), single-stranded RNA (ssRNA), and/or derivatives thereof. A nucleic acid may be natural or synthetic.

Generally, the term "fluorescent nucleic acid stain" or "fluorescent nucleic acid dye" refers to a dye capable of binding to a nucleic acid to form a fluorescent dye-nucleic acid complex. A fluorescent nucleic acid dye is typically non-fluorescent or weakly fluorescent by itself, but becomes highly fluorescent upon nucleic acid binding. Generally, the term "non-fluorescent, nucleic acid-binding molecule" refers to a nucleic acid-binding molecule that may or may not be a dye and that does not become fluorescent upon binding to nucleic acid. Generally, the term "fluorescent DNA dye" refers to a dye that becomes fluorescent upon binding to DNA. Generally, the term "fluorescent, non-nucleic acid dye" refers to a fluorescent dye that does not bind to nucleic acid. Generally, the term "non-fluorescent, non-nucleic acid dye" refers to a dye that is neither fluorescent nor nucleic acid-binding. Such a dye is commonly called a fluorescence quencher. Frequently, a fluorescence quencher is used to form a FRET pair with a fluorescent dye. Generally, the term "reporter dye" refers to a fluorescent dye whose emitted fluorescence contributes to the final detected fluorescence signal.

Generally, the term "polymerase chain reaction" or "PCR" refers to a technique for amplifying the amount of DNA. Generally, the term "quantitative, real-time PCR" or "qPCR" refers to a technique to monitor the growing amount of DNA in the course of a PCR.

In general, fluorescent nucleic acid dyes can be classified into two major classes: intercalators and minor groove-binders. Generally, fluorescent intercalators are dyes that bind to double-stranded DNA or double-stranded RNA by inserting themselves in between a neighboring base pair. Generally, minor groove-binders are dyes that bind to the minor groove of double-stranded DNA. There are still other dyes that may bind to nucleic acids via multiple modes, including electrostatic interaction between a positively charged dye and the negatively charged nucleic acid.

Although a variety of fluorescent nucleic acid dyes have become commercially available, and methods for improving the dyes for non-qPCR uses have been developed, not all nucleic acid stains are suitable for qPCR application. Additionally, little is known as to what structural elements are required for a good qPCR dye.

In general, from a performance point of view, an ideal dye for qPCR should meet various criteria, as now described. The dye should be thermally stable at high temperature (from about 60° C. to about 96° C.) in a PCR buffer and hydrolytically stable at low temperature (from about −20° C. to about 4° C.) when the media becomes alkaline. The dye should not inhibit the PCR process, this generally being the most important criteria, as in the most severe cases of PCR inhibition, the PCR process may not even start, and in milder cases, the Ct number may be delayed, or only a very low dye concentration may be used, such that the fluorescence signal is limited. The dye should be non-fluorescent or minimally fluorescent in the absence of DNA, but become highly fluorescent in the presence of DNA. The absorption and emission wavelengths of the dye should be compatible with instruments used in connection with qPCR, such as the existing instruments previously described. The DNA binding of the dye should have little or no sequence preference. The fluorescence intensity of the DNA-dye complexes should be linearly related to the amount of DNA present. A dye described herein may or may not meet one or more of the above-described criteria.

A method for designing a fluorescent nucleic acid dye, such as one suitable for qPCR, for example, is provided. The method comprises covalently linking two or three monomeric dyes with a suitable linker to form a dimeric dye or a trimeric dye. A dye described herein, when in solution, may assume a predominantly hairpin-like conformation due to intramolecular dimer formation. This hairpin-like conformation or state of the dye is inactive with respect to nucleic acids, or incapable of interacting with nucleic acids. It is believed that the dye, when in solution and in the presence of nucleic acids, also assumes an open random conformation or state, which exists in small quantity and in substantial equilibrium with the hairpin conformation. The open random conformation or state of the dye is active with respect to nucleic acids, or capable of interacting or binding with nucleic acids. It is believed that when the dye is in the presence of an increasing amount of nucleic acids, an equilibrium shift from the hairpin state toward the intermediate, open random state, or DNA-binding state, occurs. It is believed that this mechanism, sometimes referred to as a "release-on-demand DNA-binding mechanism," reduces PCR inhibition that may otherwise be associated with the dye. As a consequence, the dye may be used in PCR processes at a higher concentration than might otherwise be possible, and thus, may provide for greater nucleic acid detection sensitivity than might otherwise be possible. The reduction in PCR inhibition may be dramatic, and the increase in nucleic acid detection sensitivity may be significant.

A dimeric dye or trimeric dye described herein may posses any number of desirable characteristics. By way of example, such a dye may have a background fluorescence that is reduced relative to that of its monomeric dye constituents. Relatively low background fluorescence generally corresponds to relatively enhanced nucleic acid detection sensitivity. Thus, such a dye is generally associated with enhanced nucleic acid detection sensitivity. Further by way of example, a dye described herein may be more thermally and/or hydrolytically stable than SYBR Green I. Still further by way of example, a dye described herein may have absorption and emission wavelengths other than those associated with existing qPCR dyes.

A fluorescent dimeric nucleic acid dye may have the general structure (Structure 1) set forth directly below.

Structure 1

In Structure 1, independently, each dye of dye $Q_1$ and dye $Q_2$ is selected from a fluorescent nucleic acid dye, a non-fluorescent nucleic acid dye, a fluorescent non-nucleic acid dye, and a non-fluorescent non-nucleic acid dye. $Q_1$ and $Q_2$ may be selected and combined in a manner to encourage or to ensure desired properties of the resulting dimeric dye. At least one dye of dye $Q_1$ and dye $Q_2$ is a reporter dye. Further, at least one dye of dye $Q_1$ and dye $Q_2$ is a fluorescent nucleic acid dye or a non-fluorescent nucleic acid dye. The reporter dye and fluorescent nucleic acid dye may be the same or different. BRIDGE may be positively charged to a relatively limited extent or substantially neutral in charge, and may be a substantially flexible constituent that facilitates intramolecular dimer formation to produce the dimeric dye.

A fluorescent trimeric nucleic acid dye may have the general structure (Structure 2) set forth directly below.

Structure 2

In Structure 2, independently, each dye of dye $Q_1$, dye $Q_2$, and dye $Q_3$ is selected from a fluorescent nucleic acid dye, a non-fluorescent nucleic acid dye, a fluorescent non-nucleic acid dye, and a non-fluorescent non-nucleic acid dyes. $Q_1$, $Q_2$, and $Q_3$ may be selected and combined in a manner to encourage or to ensure desired properties of the resulting trimeric dye. At least one dye of dye $Q_1$, dye $Q_2$, and dye $Q_3$ is a reporter dye. Further, at least one dye of dye $Q_1$, dye $Q_2$, and dye $Q_3$ is a fluorescent nucleic acid dye or non-fluorescent nucleic acid dye. The reporter dye and fluorescent nucleic acid dye may be the same or different. BRIDGE may be positively charged to a relatively limited extent or substantially neutral in charge, and may be a substantially flexible constituent that facilitates intramolecular dimer formation to produce the trimeric dye.

A fluorescent nucleic acid dye may have the general structure (Structure 3) set forth directly below.

Structure 3

In Structure 3, independently, each dye of dye $Q_1$, dye $Q_2$, may be as described above in relation to Structure 1 and Structure 2; BRIDGE may be a substantially aliphatic linker, as previously described; and $R_r$ may be a reactive group or a functional group. Merely by way of example, $Q_1$ may be a fluorescent nucleic acid dye constituent; $Q_2$ may be a fluorescent nucleic acid dye constituent; BRIDGE may be a substantially aliphatic linker comprising from about 15 to about 150 non-hydrogen atoms and up to one positive charge; and $R_r$ may be a reactive group or a functional group, as described herein.

BRIDGE

BRIDGE may be a substantially flexible linker molecule, having no more than one positive charge. BRIDGE may be a substantially neutral and substantially flexible linker molecule. The constituents of BRIDGE may be selected to achieve such a limited positive charge or such a substantial neutrality. The property of substantial neutrality, which includes actual neutrality, is discussed further below. The property of substantial flexibility is generally related to the substantially aliphatic nature, which includes actual aliphatic nature, of BRIDGE. This substantial aliphatic nature generally refers to the non-aromaticity of BRIDGE, or non-rigidity of BRIDGE.

In Structure 1, BRIDGE is covalently attached to $Q_1$ and $Q_2$. In the case of dimeric dyes, BRIDGE may have from about 8 to about 150 non-hydrogen atoms, from about 8 to about 100 non-hydrogen atoms, from about 12 to about 60 non-hydrogen atoms, or from about 15 or about 20 to about 40 or about 50 non-hydrogen atoms, for example. In Structure 2, BRIDGE is covalently attached to $Q_1$, $Q_2$ and $Q_3$. In the case of trimeric dyes, BRIDGE may have from about 15 to about 150 non-hydrogen atoms, from about 20 to about 150 non-hydrogen atoms, from about 20 to about 100 non-hydrogen atoms, or from about 30 to about 70 non-hydrogen atoms, for example.

BRIDGE may incorporate at least one independent nucleic-acid-binding-enhancing-group (NABEG). A NABEG is a moiety capable of binding to nucleic acids in the form of electrostatic, hydrophobic, or hydrogen-bonding interactions. Merely by way of example, a NABEG may be selected from primary amines; secondary amines; tertiary amines; ammoniums; amidines; aryl groups optionally comprising hetero atoms selected from N, O, S, and any combination thereof moieties having bonds comprising hetero atoms of high electronegativity; and any combination thereof.

Primary, secondary and tertiary amines and amidines are basic groups and therefore are positively charged or at least partially positively charged at physiological pH. Ammonium groups, or quaternized nitrogen groups, are permanently positively charged. Generally speaking, positively charged or partially positively charged groups enhance the nucleic acid binding of the dye via electrostatic interaction, a property that may be exploited in the development of highly sensitive fluorescent nucleic acid stains. It is generally undesirable to use BRIDGE having excessive positive charges to produce a dye of the present invention. For example, a suitable BRIDGE of a dimeric dye or a trimeric dye of the invention may comprise no more than one positive charge. BRIDGE may be a substantially flexible and neutral or substantially neutral linker. In this context, substantially neutrality refers to slight charge. By way of example, BRIDGE could comprise a weakly basic constituent, such as a pyridine group or a pyrazine group, for example, such that when it is in aqueous solution, a very small amount of positive charges may be present. Further by way of example, in a case (optional) in which BRIDGE comprises at least one neutral NABEG, the exact amount of positive charge may be generally related to the $pK_a$ of the NABEG. Generally, the higher the $pK_a$ of the NABEG, the more likely the NABEG is protonated and thus, positively charged. By way of example, a suitable weakly basic NABEG group may have a $pK_a$ of about 11 or less, about 8 or less, or about 7 or less.

There may be a tendency to form an intramolecular dimer, primarily H-dimer, which may be a particularly useful property in the nucleic acid dye produced. For example, in the case of a dimeric dye described herein, H-dimer formation may produce a hairpin-like structure, wherein H-dimer forms a stem portion of the hairpin and BRIDGE forms a curved portion, as schematically illustrated in FIG. 1. The phenomenon of H-dimer formation in connection with certain dyes has been described in West, et al., *J. Phys. Chem.* (1965); Rohatgi, et al., *J. Phys. Chem.* (1966); Rohatgi, et al., *Chem. Phys. Lett.* (1971); and Khairutdinov, et al., *J. Phys. Chem.* (1997). Formation of an intramolecular H-dimer may be facilitated when BRIDGE is a flexible and neutral or substantially neutral hydrocarbon linker, optionally comprising one or more neutral NABEG(s).

H-dimer formation may be characterized by a large blue shift of the dye absorption spectrum. By way of example, the absorption spectra of a monomeric dye AO (acridine orange) and a related dimeric dye, AOAO-7, that forms an intramolecular dimer, are shown in FIG. 2. The 471 nm peak associated with the AOAO-7 dimer indicates intramolecular H-dimer formation. The absorption spectra of both the monomer and the dimer become similar once DNA-binding occurs, indicating the opening up of the hairpin structure. By way of example, as shown in FIG. 3, the disappearance of the 471 nm peak from AOAO-7 dimer indicates the opening up of the hairpin structure upon DNA binding.

H-dimer formation in a dye described herein may be associated with two major benefits. One of the major benefits is a reduction, sometimes dramatic, in background fluorescence, coupled with a substantial increase in fluorescence upon DNA-binding, as demonstrated by a large gain in the fluorescence signal. This benefit may be appreciated by comparing the fluorescence spectra of a monomeric acridine orange dye, DMAO, and a dimeric acridine orange dye, AOAO-7, in the absence and presence of DNA. For example, as shown in FIG. 4, relative to the monomeric DMAO dye, the dimeric AOAO-7 dye is associated with lower background fluorescence and higher fluorescence upon binding to DNA.

Intramolecular dimer-associated fluorescence quenching may be so efficient that a dye described herein may be constructed from at least one monomeric dye that is not normally considered to be very desirable, such as at least one monomeric dye that has high background fluorescence, for example. An example of this is shown in FIG. 4, which features acridine orange (AO) and a dimer thereof. Although AO is one of the earliest known nucleic acid-binding dyes and has desirable wavelengths, it has not been widely used for nucleic acid detection because of its relatively high background fluorescence. As demonstrated in FIG. 4, relative to the monomeric AO dye, the dimeric dye AOAO-7 has much lower background fluorescence.

H-dimer formation occurs via intramolecular, rather than intermolecular, interaction. The H-dimer formation occurs via the covalent linkage of two or three dyes, such as a pair of desirable monomeric dyes, for example. The H-dimer formation may be accomplished relatively easily, without the need for an additional reagent, such as an additional reagent that may interfere with a useful application of the dye, for example. By way of example, a dimeric dye may be formed from a pairing of one nucleic acid-binding dye constituent and one non-nucleic acid-binding fluorescent dye constituent in solution, without the use of an additional reagent. Further by way of example, a trimeric dye may be prepared from two nucleic acid-binding dye constituents and one non-nucleic acid-binding fluorescent dye constituent in solution, again, without the use of an additional reagent. The H-dimer formation provides a useful way to trap the dye in a non-DNA-binding state, which has no inhibitory effect on PCR and which shifts to the open random state or the DNA-binding state only when DNA is present. Thus, the effective dye concentration, or the concentration of the dye in the open random state, can be kept low, even though a high total dye concentration is used to increase the qPCR sensitivity.

As mentioned above, H-dimer formation in a dye described herein may be associated with another major benefit. This unexpected benefit is that H-dimer formation in a dye may significantly reduce the inhibitory effect of the dye to PCR in a qPCR application. By way of example, usually, for a DNA sample of a given concentration, the fluorescent signal from a fluorescent DNA dye is proportional to the dye concentration, until dye saturation. By way of example, a higher dye concentration is associated with a greater formation of DNA-dye complexes, and thus, greater, or brighter, fluorescence, until dye saturation. Therefore, ideally, one would wish to start with a high enough dye concentration for maximal sensitivity in a qPCR application. In practice, however, all DNA dyes that have previously used for qPCR inhibit the DNA amplification process in varying degrees. Typically, a higher concentration of such a previous dye has been associated with greater dye inhibition of the amplification or PCR process. Thus, the concentration of such a previous dye has usually been made to be much lower for a qPCR application than it would be for a non-qPCR application.

This lowering of dye concentration in qPCR applications results in a sacrifice in terms of end-point fluorescent signal strength, as may be discerned from the following discussion of the most widely used DNA dye for qPCR, SYBR Green I, by way of example. The concentration of SYBR Green 1 that used in qPCR is not provided by the manufacturer, such that precise comparison with other dyes is not easy or routine. However, as the concentration of a dye is linearly related to its optical density according to Beer's law, the optical density characteristics of SYBR Green 1 solution used in qPCR and another dye solution used in qPCR may be used to at least qualitatively compare the respective concentrations. For example, a typical optical density for SYBR Green 1 solution used in qPCR is from 0.025 to 0.05, while the optical density for a solution of Dye No. 19 of Table 2 herein used in qPCR is typically from about 0.04 to about 0.8, or more typically, from about 0.1 to about 0.4. The SYBR Green I dye shows a significant inhibition effect when the dye concentration is increased from 0.5×, which corresponds to an optical density of 0.025 at the absorption peak of 495 nm, to a 1× concentration, which corresponds to an optical density of 0.05 at the same absorption peak. As shown in FIG. 8, while SYBR Green I at the 1× concentration has a higher end-point fluorescent signal relative to SYBR Green I at the 0.5× concentration, the cycle number, or Ct value, associated with the 1× dye concentration is delayed. This delayed Ct value indicates that SYBR Green I significantly inhibits PCR at higher dye concentration. The dimeric dye, AOAO-12, exhibits little or no inhibition when the dye concentration is increased from a 1× dye concentration, which corresponds to an optical density of 0.1 at the absorption peak of 471 nm, to a 2× dye concentration, which corresponds to an optical density of 0.2 at the same absorption peak. Because AOAO-12 shows little or no PCR inhibition, it can be used at a concentration that is relatively high and provide a fluorescent signal that can be several times higher than that of SYBR Green I, as shown in FIG. 9. In brief, AOAO-12 shows little or no PCR inhibition within a wide concentration range, and thus can be used at a higher concentration for an increased fluorescent signal.

It is believed that the above-described substantial lack of PCR inhibition that may be associated with dyes described herein, such that a higher dye concentration can be used, may be explained by a "release-on-demand" mechanism that is schematically illustrated in FIG. 1. That is, it is believed that in solution, a dimeric dye exists in a dynamic equilibrium between a closed hairpin conformation and an open random conformation, as shown in FIG. 1. In general, the hairpin conformation is much more stable than the open random conformation and is predominant. The dominance of the hairpin conformation of the dye is supported by ultraviolet/visible spectra, which show a substantial shift of the dimer spectrum relative to the monomer spectrum. The hairpin conformation is an inactive form of the dye, while the open conformation is an active form of the dye, capable of DNA binding. When DNA is present, dye in the open conformation shifts to a DNA-bound conformation, more dye in the hairpin conformation shifts to the open conformation, and dye in the open conformation stays at a very low concentration. In other words, the majority of the dye is trapped in the non-DNA-binding hairpin conformation and is only released to the open conformation, or the DNA-binding form, in response to greater DNA presence. This "release-on-demand" mechanism makes it possible for a dye to be used at a relatively high concentration without adversely affecting the PCR process itself. Unlike a dye described herein, SYBR Green I does not have a non-DNA-binding conformation that helps lower the effective concentration of the dye and thus shows a highly concentration-dependent PCR inhibitory effect.

The nucleic acid stains described herein are relatively simple and can be prepared on a desirable scale, such as in amounts measured in grams to tens of grams, for example, on a fairly routine basis. These nucleic acid stains may be used fairly universally for detection of DNA amplification and for relatively routine research applications. By way of example, fluorescent nucleic acid dyes may be used to detect the presence and amount of DNA in a substantially non-sequence-selective manner, and in a relatively universal manner.

BRIDGE may have the formula (Formula 1) set forth directly below.

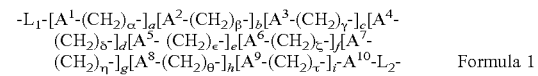
Formula 1

In Formula 1, each substituent of substituent $L_1$ and substituent $L_2$ (each of which may be referred to as simply "L") is part of BRIDGE. $L_1$ is covalently bound to one dye constituent of the $Q_1$ dye constituent and the $Q_2$ dye constituent, and $L_2$ is covalently bound to the dye constituent of the $Q_1$ dye constituent and the $Q_2$ that is other than said one dye constituent. Independently, each of $L_1$ and $L_2$ is a moiety comprising a single bond; a polymethylene unit having 1 carbon to about 12 carbons optionally comprising at least one hetero atom selected from N, O and S; or an aryl group optionally comprising at least one hetero atom selected from N, O and S. The subscripts associated with the $(CH_2)$ methylene units, namely, $\alpha$, $\beta$, $\gamma$, $\delta$, $\epsilon$, $\zeta$, $\eta$, $\theta$, and $\tau$, may be the same or different, each independently indicating the size of the associated methylene unit and being zero or an integer from 1 to about 20 or from 1 to about 12. The subscripts associated with the bracketed portions of Formula 1, namely, a, b, c, d, e, f, g, h, and i, may be the same or different, each independently indicating the size of the associated bracketed portion of the formula and being zero or an integer from 1 to about 20, or from 1 to about 10 or from 1 to about 5.

$A^1$, $A^2$, $A^3$, $A^4$, $A^5$, $A^6$, $A^7$, $A^8$, $A^9$, and $A^{10}$ may be the same or different, each independently, being a nucleic-acid-binding-enhancing-group (NABEG); a branched alkyl optionally comprising at least one hetero atom selected from N, O and S; or at least one saturated 5- or 6-membered ring optionally comprising at least one hetero atom selected from N, O and S. $A^1$, $A^2$, $A^3$, $A^4$, $A^5$, $A^6$, $A^7$, $A^8$, $A^9$, and $A^{10}$ may be such that BRIDGE comprises at most one positive charge, or is substantially neutral, and in the latter case, each of these constituents, independently, may itself be substantially neutral, which includes actual neutrality. NABEGs may be selected from moieties comprising at least one bond linkage that comprises at least one hetero atom of high electronegativity or S; and aryl groups optionally comprising at least one hetero atom selected from halogens, N, O, and S. Examples of moieties comprising at least one bond linkage that comprises at least one hetero atom of high electronegativity or S include, but are not limited to moieties comprising at least one amide bond, urethane bond, urea bond, thiourea bond, ether bond, or thioether bond.

One of $A^1$, $A^2$, $A^3$, $A^4$, $A^5$, $A^6$, $A^7$, $A^8$, $A^9$, and $A^{10}$ may be a branching unit covalently linked to $Q_3$ through a branch B' and a linker L, as shown in the formula (Formula 2) set forth directly below.

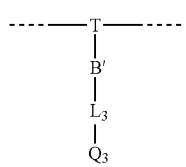

Formula 2

In Formula 2, T may be a substituted carbon, a substituted nitrogen, or an aryl optionally comprising at least one hetero atom selected from O, N and S. B' has the formula (Formula 3) set forth directly below.

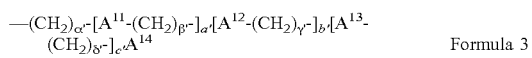

Formula 3

The —$(CH_2)_{\alpha'}$ of Formula 3 is covalently linked to T of Formula 2 and $A^{14}$ of Formula 3 is covalently linked to $L_3$ of Formula 2. Independently, each of $A^{11}$, $A^{12}$, $A^{13}$, and $A^{14}$ may be a neutral or substantially neutral nucleic-acid-binding-enhancing-group (NABEG); a neutral branched alkyl optionally comprising at least one hetero atom selected from N, O and S; or at least one neutral saturated 5- or 6-membered ring optionally comprising at least one hetero atom selected from N, O and S, as described previously in connection with each of $A^1$, $A^2$, $A^3$, $A^4$, $A^5$, $A^6$, $A^7$, $A^8$, $A^9$, and $A^{10}$ of Formula 1. The subscripts associated with the ($CH_2$) methylene units, namely, $\alpha'$, $\beta'$, $\gamma'$, and $\delta'$, may be the same or different, each independently indicating the size of the associated methylene unit and being zero or an integer from 1 to about 20. The subscripts associated with the bracketed portions of Formula 3, namely, a', b', and c', may be the same or different, each independently indicating the size of the associated bracketed portion and being zero or an integer from 1 to about 20.

In Formula 2, independently, $L_3$ may be a moiety comprising a single bond; a polymethylene unit having 1 carbon to about 12 carbons optionally comprising at least one hetero atom selected from N, O and S; or an aryl group optionally comprising at least one hetero atom selected from halogens, N, O and S, as described previously in connection with each of the L components of Formula 1. The resulting molecule is a trimeric nucleic acid stain.

One of $A^1$, $A^2$, $A^3$, $A^4$, $A^5$, $A^6$, $A^7$, $A^8$, $A^9$, and $A^{10}$ may be a branching unit covalently linked to a reactive group $R_r$, through a branch B' and a linker $L_3$, as shown in the formula (Formula 4) set forth directly below.

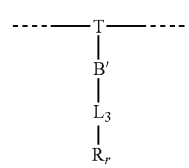

Formula 4

In Formula 4, T, B' and $L_3$ are defined as set forth above in connection with Formula 2 and Formula 3, with the exception that $L_3$ is covalently bound to $R_r$. The resulting molecule may be a nucleic acid stain as represented by Structure 3 above.

A dye with a reactive group —$R_r$ can be used to label any of a wide variety of molecules that comprise a suitable functional group or are derivatized to comprise a suitable functional group. It is understood that the term "reactive group" can be used to refer to a "reactive group" or a "functional group" and that the term "functional group" can be used to refer to a "reactive group" or a "functional group." Either term may refer, and both terms may refer, to a bond-forming group on a dye, or to a bond-forming group on the substrate molecule to be labeled. Here, by way of convenience, but not limitation, a bond-forming group on the dye will generally be referred to as a reactive group and a bond-forming group on the substrate molecule will generally be referred to as a functional group. Merely by way of example, a dye with a reactive group or functional group —$R_r$ may have up to one positive charge.

In general, conjugation of a dye to a substrate molecule may confer a nucleic acid-detection property of the dye on the conjugated substrate molecule. The reactive group and the functional group are typically an electrophile and a nucleophile, respectively, that can form a covalent bond. According to one alternative, the reactive group is a photoactivatable group capable of reacting with a hydrocarbon molecule upon ultraviolet photoactivation or photolysis. According to another alternative, the reactive group is a dienophile capable of reacting with a conjugated diene via a Diels-Alder reaction. According to yet another alternative, the reactive group is a 1,3-diene capable of reacting with a dienophile. Still other reactive group/functional group pairs may be selected based on Staudinger chemistry or the reaction between an azido group and a terminal alkyne (the so-called Click chemistry). Merely by way of example, examples of useful reactive groups, functional groups, and corresponding linkages are listed below in Table 1.

TABLE 1

Examples of Reactive Groups, Functional Groups, and Covalent Linkages

| Electrophilic Group | Nucleophilic Group | Resulting Covalent Linkage |
|---|---|---|
| activated esters* | amines/anilines | Carboxamides |
| acrylamides | Thiols | Thioethers |
| acyl azides** | amines/anilines | Carboxamides |
| acyl halides | amines/anilines | Carboxamides |
| acyl halides | Alcohols/phenols | Esters |
| acyl nitriles | Alcohols/phenols | Esters |
| acyl nitriles | amines/anilines | Carboxamides |
| aldehydes | amines/anilines | Imines |
| aldehydes or ketones | Hydrazines | Hydrazones |
| aldehydes or ketones | Hydroxylamines | Oximes |
| alkyl halides | amines/anilines | alkyl amines |
| alkyl halides | carboxylic acids | Esters |
| alkyl halides | Thiols | Thioethers |
| alkyl halides | alcohols/phenols | Esters |
| alkyl sulfonates | Thiols | Thioethers |
| alkyl sulfonates | carboxylic acids | Esters |
| alkyl sulfonates | alcohols/phenols | Esters |
| anhydrides | alcohols/phenols | Esters |
| anhydrides | amines/anilines | Carboxamides |
| aryl halides | Thiols | Thiophenols |
| aryl halides | Amines | aryl amines |
| aziridines | Thiols | Thioethers |
| boronates | Glycols | boronate esters |
| carboxylic acids | amines/anilines | Carboxamides |
| carboxylic acids | Alcohols | Esters |
| carboxylic acids | Hydrazines | Hydrazides |
| carbodiimides | carboxylic acids | N-acylureas or anhydrides |
| diazoalkanes | carboxylic acids | Esters |
| epoxides | Thiols | Thioethers |
| haloacetamides | Thiols | Thioethers |
| halotriazines | amines/anilines | Aminotrizaines |
| halotriazines | alcohols/phenols | triazinyl ethers |
| imido esters | amines/anilines | Amidines |
| isocyanates | amines/anilines | Ureas |
| isocyanates | alcohols/phenols | Urethanes |
| isothiocyanates | amines/anilines | Thioureas |
| maleimides | Thiols | Thioethers |
| phosphoramidites | Alcohols | phosphite esters |
| silyl halides | Alcohols | silyl ethers |
| sulfonate esters | amines/anilines | alkyl amines |
| sulfonate esters | Thiols | Thioethers |
| sulfonate esters | carboxylic acids | Esters |
| sulfonate esters | Alcohols | Ethers |
| sulfonyl halides | amines/anilines | Sulfonamides |
| sulfonyl halides | phenols/alcohols | sulfonate esters |

*Activated esters, as understood in the art, generally have the formula □□COΩ, where Ω is a good leaving group, such as succinimidyloxy (□□OC$_4$H$_4$O$_2$), sulfosuccinimidyloxy (□□OC$_4$H$_3$O$_2$□□SO$_3$H), or -l-oxybenzotriazolyl (□□OC$_6$H$_4$N$_3$), for example; or an aryloxy group or aryloxy substituted one or more times by electron-withdrawing substituent(s), such as nitro, fluoro, chloro, cyano, trifluoromethyl, or combinations thereof, for example, used to form activated aryl esters; or a carboxylic acid activated by a carbodiimide to form an anhydride or mixed anhydride □□OCOR$^a$ or □□OCNR$^a$NHR$^b$, where R$^a$ and R$^b$, which may be the same or different, are independently C$_1$-C$_6$ alkyl, C$_1$-C$_6$ perfluoroalkyl, or C$_1$-C$_6$ alkoxy; or cyclohexyl, 3-dimethylaminopropyl, or N- morpholinoethyl.
**Acyl azides can also rearrange to isocyanates.

The reactive group may be one that will react with an amine, a thiol, or an aldehyde. The reactive group may be an amine-reactive group, such as a succinimidyl ester, for example, or a thiol-reactive group, such as a maleimide, a haloacetamide, or a methanethio-sulfonate (MTS), for example, or an aldehyde-reactive group, such as an amine, an aminooxy, or a hydrazide, for example.

A reactive dye may be conjugated to any of a wide variety of substrate molecules. For example, a suitable substrate may be a nucleotide, an oligonucleotide, a peptide, a protein, a hapten, a drug, a microparticle, a synthetic polymer, a natural polymer, a biological cell, a virus, a molecule of a solid surface, such as the surface of a silicon wafer, the surface of a polypropylene substrate or container, or the like, for example. A molecule to be labeled may be a nucleotide, an oligonucleotide, a peptide, or a molecule that may interact with a nucleic acid. For example, DNA-binding dyes have been used to label an oligonucleotide-based probe for qPCR applications. Shiguro, T., et al, *Nucleic Acids Res.* 24: 4992-7 (1996).

$A^1$, $A^2$, $A^3$, $A^4$, $A^5$, $A^6$, $A^7$, $A^8$, $A^9$, and $A^{10}$, which may be the same or different, may, independently, be NABEGs selected from moieties comprising at least one bond linkage that comprises at least one hetero atom of high electronegativity or S; and aryl groups optionally comprising at least one hetero atom selected from halogens, N, O, and S. Examples of moieties comprising at least one bond linkage that comprises at least one hetero atom of high electronegativity or S include, but are not limited to moieties comprising at least one amide bond, urethane bond, urea bond, thiourea bond, ether bond, or thioether bond. $A^1$, $A^2$, $A^3$, $A^4$, $A^5$, $A^6$, $A^7$, $A^8$, $A^9$, and $A^{10}$ may be such that BRIDGE comprises at most one positive charge, or is substantially neutral, and in the latter case, each of these constituents may itself be substantially neutral, which includes actual neutrality.

BRIDGE may comprise any suitable number of non-hydrogen atoms, as previously described, such as from about 10 to about 100 non-hydrogen atoms, for example, or from about 12 to about 60 non-hydrogen atoms for the dimeric dyes, and from about 20 to about 100 non-hydrogen atoms for the trimeric dyes. For example, BRIDGE may have from about 15 to about 40 non-hydrogen atoms for the dimeric dyes, and from about 30 to about 70 non-hydrogen atoms for the trimeric dyes.

Merely by way of example, BRIDGE may have the formula (Formula 5) set forth directly below.

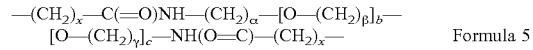

$$-(CH_2)_x-C(=O)NH-(CH_2)_\alpha-[O-(CH_2)_\beta]_b-[O-(CH_2)_\gamma]_c-NH(O=C)-(CH_2)_x- \qquad \text{Formula 5}$$

In one such case, for example, $L_1$ of BRIDGE is $-(CH_2)_x-$ and $L_2$ of BRIDGE is $-(CH_2)_x-$, where each x, independently, is an integer selected from 1 to 11, inclusive; $A^1$ of BRIDGE is $-C(=O)NH-$; a of BRIDGE is 1; $A^2$ of BRIDGE is $-O-$; $A^3$ of BRIDGE is $-O-$; α may be an integer selected from 2 to about 20, inclusive; each of β and γ, independently, may be 2 or 3; b may be zero or an integer selected from 2 to about 20; and c may be zero or 1; each of d, e, f, g, h and i of BRIDGE is 0; and $A^{10}$ of BRIDGE is $-NH(O=C)C-$. Merely by way of example, BRIDGE may be as just described, wherein c is 1. Further, merely by way of example, BRIDGE may be as just described, wherein c is 1, and further, wherein x may be 5; α and γ may be the same and may be 2 or 3; β may be 2; and b may be 0, 1, 2 or 3.

Monomeric Dyes

Independently, each of the constituent monomeric dyes or functional molecules, Q1, Q2, and Q3, used for the dimeric and trimeric dyes may be selected from: 1) fluorescent nucleic acid dyes; 2) non-fluorescent, nucleic acid-binding molecules; 3) fluorescent, non-nucleic acid dyes; and 4) non-fluorescent, non-nucleic acid dyes. In general, Q1, Q2 and Q3 may be selected and covalently linked via BRIDGE in a manner to encourage or to ensure intramolecular dimer formation in the absence of DNA and formation of highly fluorescent DNA-dye complexes upon DNA binding. Intramolecular dimer formation may be sufficient to provide the useful hairpin conformation of a dimeric dye, as previously described. Such a dimeric dye may possess desirable properties, such as low background fluorescence and low PCR inhibition, for example. As previously described, it is possible to use a dimeric dye as described herein at a relatively high concentration to generate a desirable, or strong, fluorescent signal.

Intramolecular dimer formation may be confirmed by comparing the absorption spectra of a dimeric dye or trimeric dye in an aqueous solution with the absorption spectra of the related monomeric dye or dyes also in an aqueous solution. Any intramolecular dimer formation dye should cause the spectra of the component monomeric dyes in the dimer or trimer to be shifted significantly relative to the spectra of the related monomeric dye(s). In this regard, a significant shift may be about 10 nm or more, by way of example. For example, in FIG. 2, the spectra associated with AOAO-7 are shifted significantly relative to the spectra of DMAO.

When the intramolecular dimer formation is a H-dimer formation, the spectra will usually undergo a significant blue shift. In this regard, a significant shift may be about 10 nm or more, by way of example. Other types of intramolecular dimer formation are also possible and may result in spectral shift in another direction, in spectral shifts in separate directions for each of the component monomeric dyes, in an insignificant spectral shift, or in no spectral shift. In this regard, an insignificant shift may be about 5 nm or less, by way of example. In general, when there is no significant spectral shift observed, other analytical techniques may be employed to confirm the formation of any intramolecular dimer. Such analytical techniques include, but are not limited to, nuclear magnetic resonance (NMR) spectroscopy, infrared spectroscopy, and fluorescence spectroscopy, for example. Any intramolecular dye aggregation that results in a hairpin structure is generally desirable.

Various combinations of Q1, Q2, and Q3 may be useful or desirable. Merely by way of example, a dimeric dye may be constructed via five different combinations of Q1 and Q2, as schematically shown in FIG. 10. Further by way of example, examples of prepared dyes and associated intermediates are listed below in Table 2.

TABLE 2
Prepared Fluorescent Nucleic Acid Dyes
| No. | Name | Structure | MWt. | SPACER LENGTH (ATOMS) |
|---|---|---|---|---|
| 1 | DMAO | 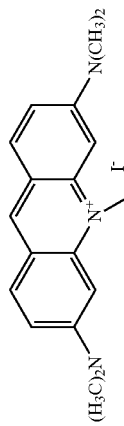 | 478.41 | N/A |
| 2 | TMAO | 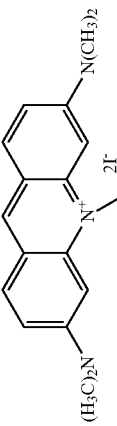 | 620.35 | N/A |
| 3 | AO-3N | 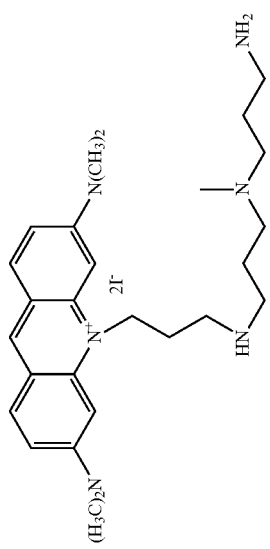 | 705.16 | N/A |

TABLE 2-continued

Prepared Fluorescent Nucleic Acid Dyes

| No. | Name | Structure | MWt. | SPACER LENGTH (ATOMS) |
|---|---|---|---|---|
| 4 | AO-2N | (structure) | 493.43 | N/A |
| 5 | PMAO | (structure) | 691.47 | N/A |
| 6 | AOAO-1 | (structure) | 926.76 | 10 |

TABLE 2-continued
Prepared Fluorescent Nucleic Acid Dyes
| No. | Name | Structure | MWt. | SPACER LENGTH (ATOMS) |
|---|---|---|---|---|
| 7 | AOAO-2 | 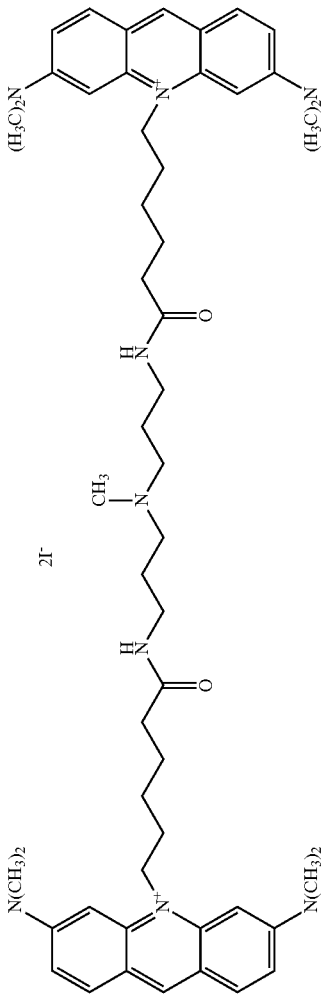 | 1124.03 | 21 |
| 8 | AOAO-3 | 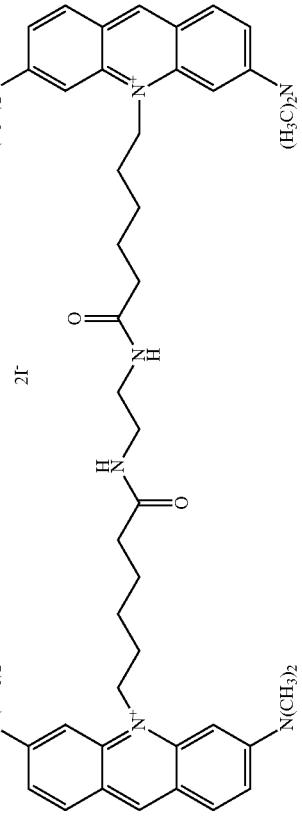 | 1038.88 | 16 |

TABLE 2-continued
Prepared Fluorescent Nucleic Acid Dyes
| No. Name | Structure | MWt. | SPACER LENGTH (ATOMS) |
|---|---|---|---|
| 9 AOAO-2Q | 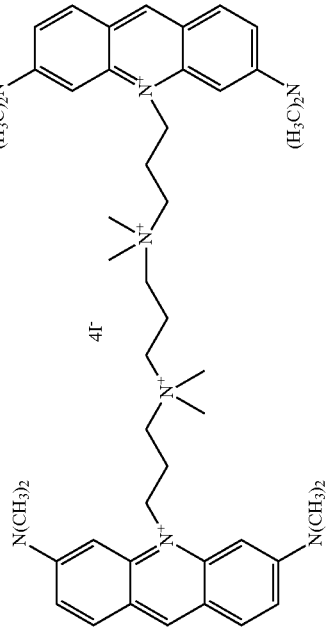 | 1252.71 | 11 |
| 10 AOAO-4 | 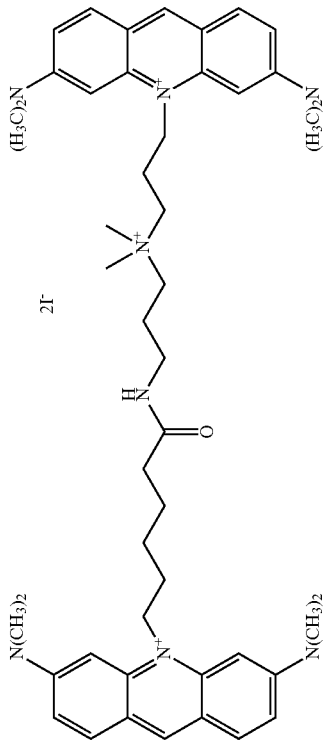 | 1041.95 | 14 |

TABLE 2-continued
Prepared Fluorescent Nucleic Acid Dyes
| No. | Name | Structure | MWt. | SPACER LENGTH (ATOMS) |
|---|---|---|---|---|
| 11 | AOAO-5 | 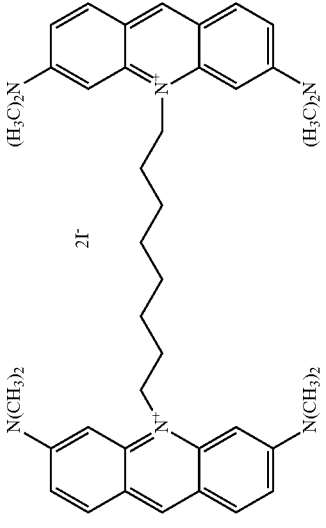 | 896.73 | 8 |
| 12 | AOAO-6 | 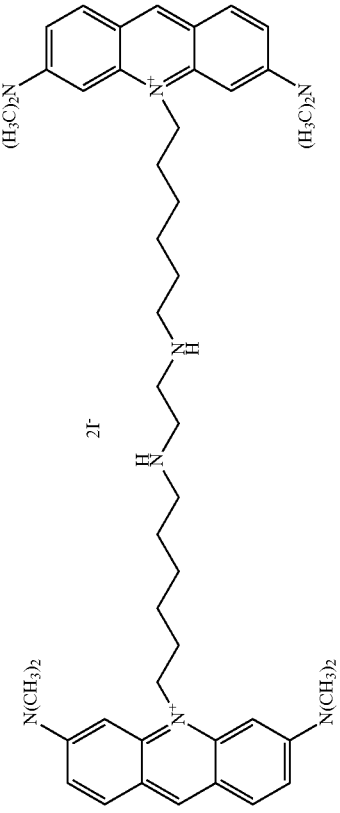 | 1010.92 | 16 |

TABLE 2-continued

Prepared Fluorescent Nucleic Acid Dyes

| No. Name | Structure | MWt. | SPACER LENGTH (ATOMS) |
|---|---|---|---|
| 13 AOAO-7 | 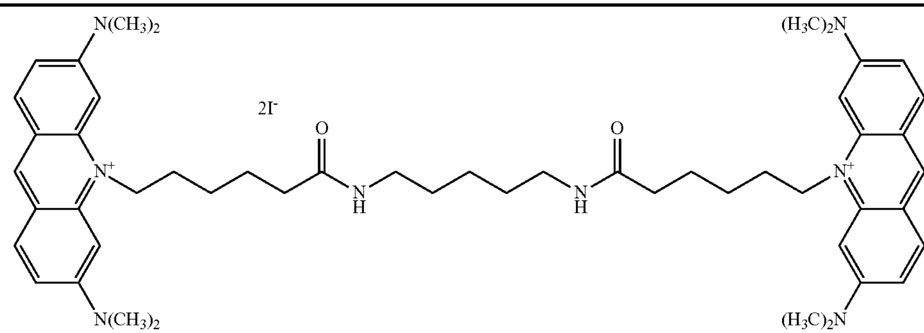 | 1080.96 | 19 |
| 14 TOTO-3 | 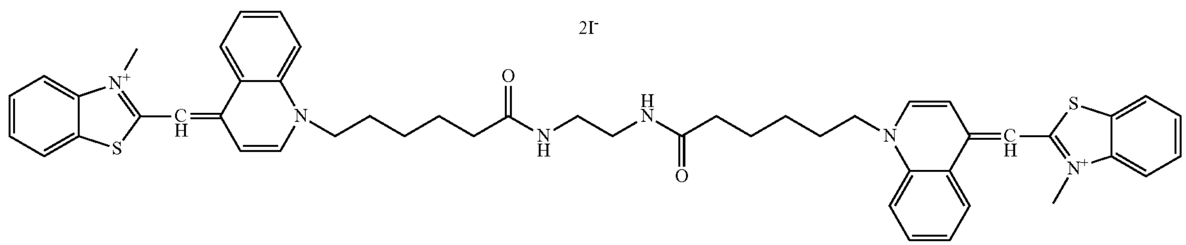 [SMILES: C[n+]1c(C=C2C=CN(CCCCCC(=O)NCCNC(=O)CCCCCN3C=CC(=Cc4sc5ccccc5[n+]4C)c4ccccc43)c3ccccc32)sc2ccccc21] | 1088.94 | 16 |
| 15 AOAO-8 | 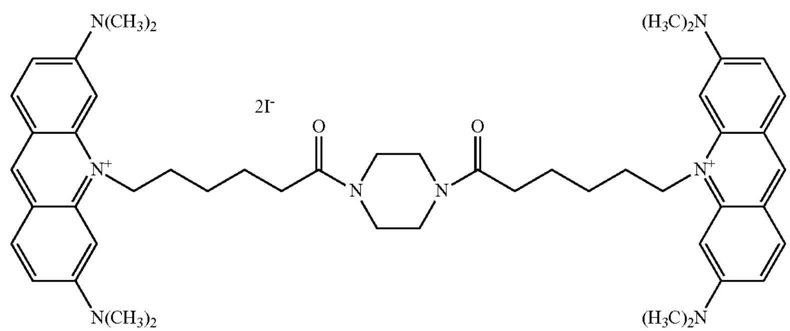 | 1064.92 | 16* |

TABLE 2-continued

Prepared Fluorescent Nucleic Acid Dyes

| No. Name | Structure | MWt. | SPACER LENGTH (ATOMS) |
|---|---|---|---|
| 16 AOAO-9 | 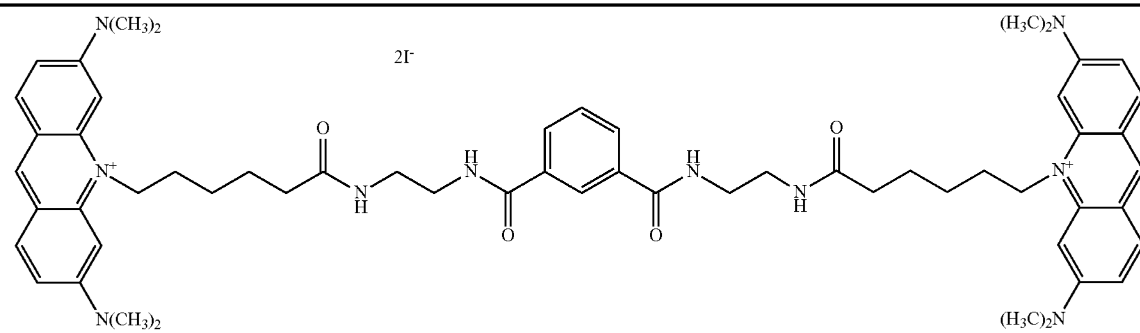 | 1229 | 25 |
| 17 AOAO-10 | 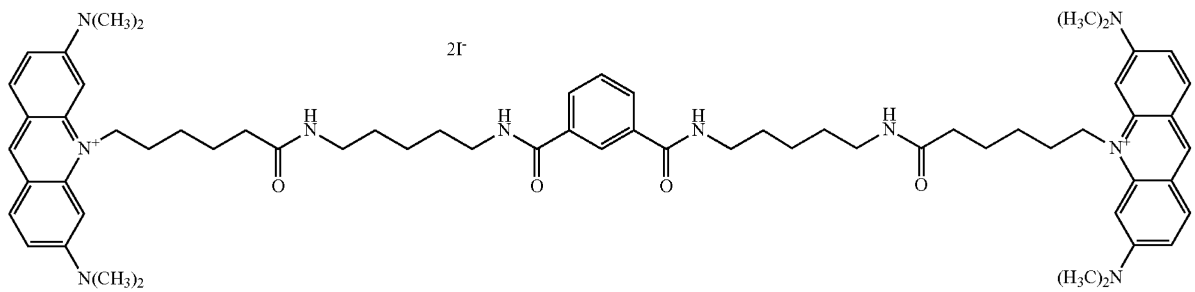 | 1313.24 | 31 |
| 18 AOAO-11 | 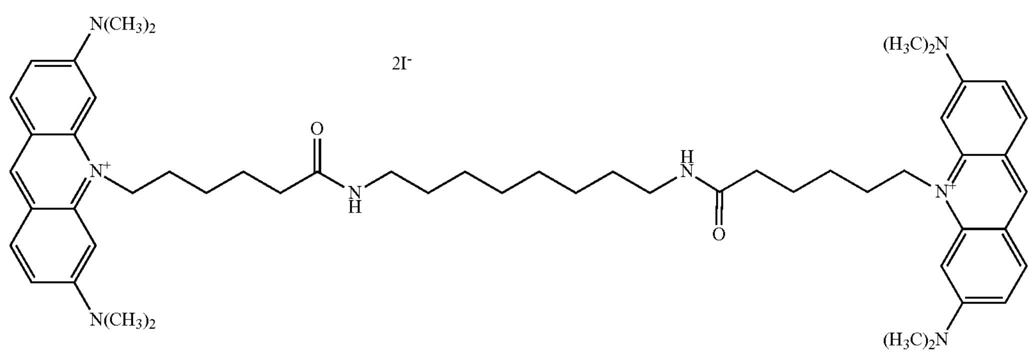 | 1123 | 22 |

TABLE 2-continued
Prepared Fluorescent Nucleic Acid Dyes
| No. | Name | Structure | MWt. | SPACER LENGTH (ATOMS) |
|---|---|---|---|---|
| 19 | AOAO-12 | 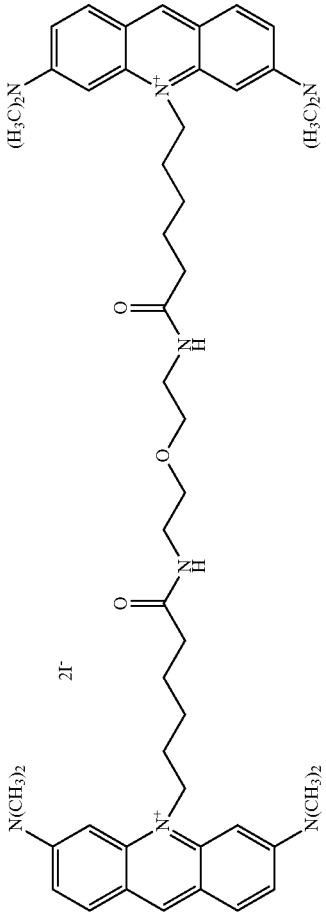 | 1082.94 | 19 |
| 20 | AOAO-13 | 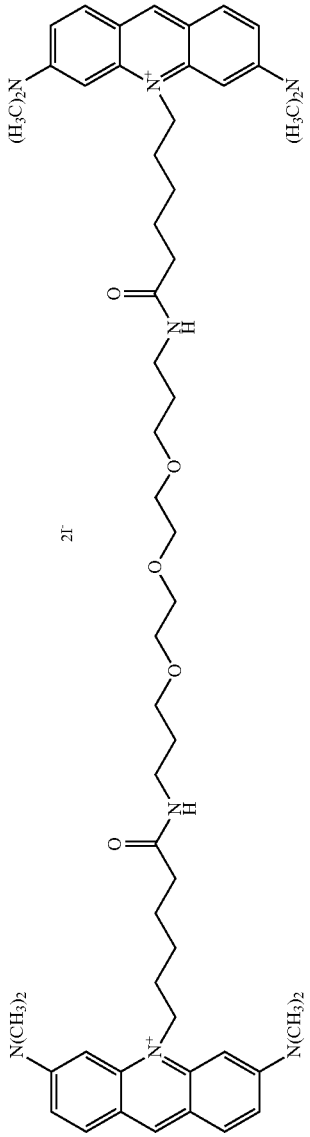 | 1215.14 | 27 |

TABLE 2-continued
Prepared Fluorescent Nucleic Acid Dyes
| No. Name | Structure | MWt. | SPACER LENGTH (ATOMS) |
|---|---|---|---|
| 21 AOAO-14 | 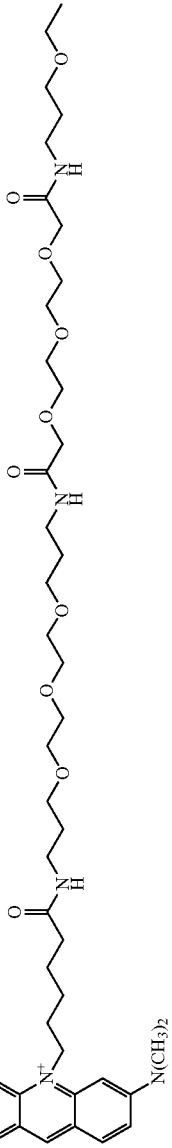 | 1621.61 | 53 |
| 22 AOAO-12R | 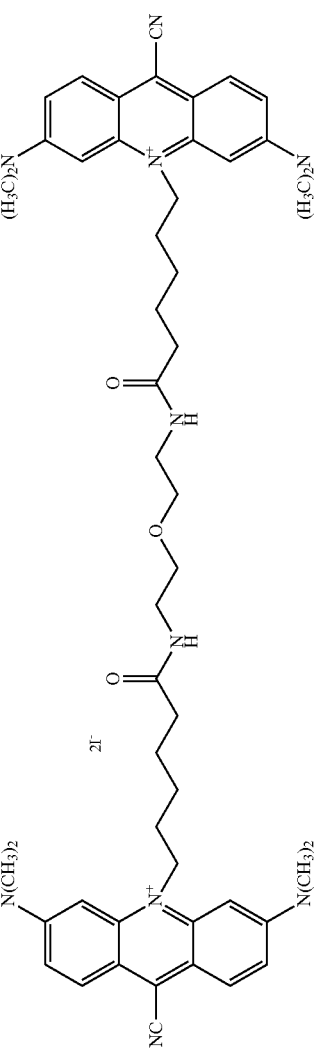 | 1132.95 | 19 |

TABLE 2-continued

Prepared Fluorescent Nucleic Acid Dyes

| No. Name | Structure | MWt. | SPACER LENGTH (ATOMS) |
|---|---|---|---|
| 23 AOTO-3 | | 1094.99 | 16 |
| 24 TOTO-12 | | 1146.23 | 20 |
| 25 TO(3)ITO(3)-12 | | 1245.34 | 20 |

TABLE 2-continued

Prepared Fluorescent Nucleic Acid Dyes

| No. | Name | Structure | MWt. | SPACER LENGTH (ATOMS) |
|---|---|---|---|---|
| 26 | TO(3)TO(3)-2 | | 1302.44 | 22 |
| 27 | AORO-7 | | 1320.25 | 21 |

TABLE 2-continued
Prepared Fluorescent Nucleic Acid Dyes
| No. Name | Structure | MWt. | SPACER LENGTH (ATOMS) |
|---|---|---|---|
| 28 RORO-12 | 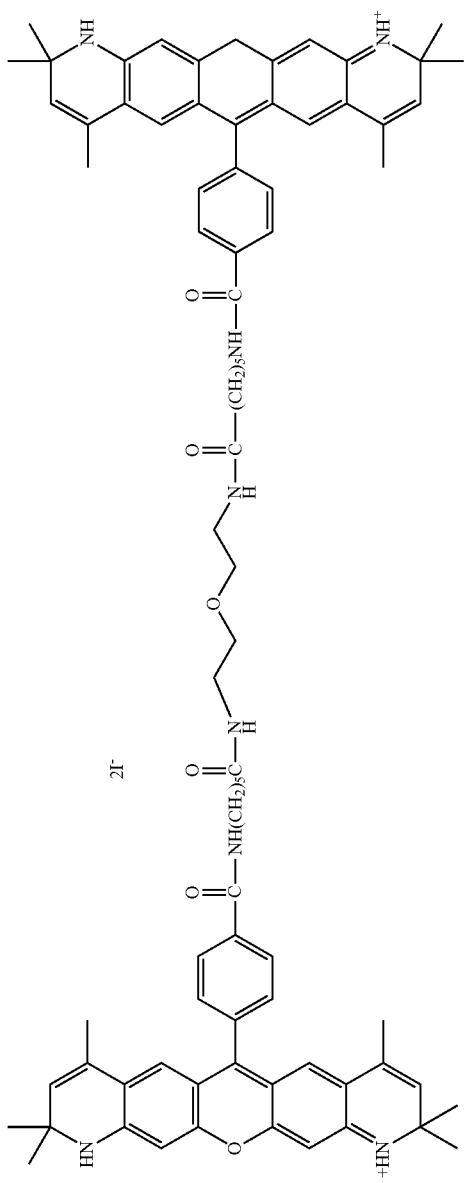 | 1550.51 | 22 |
| 29 TOTO-13 | 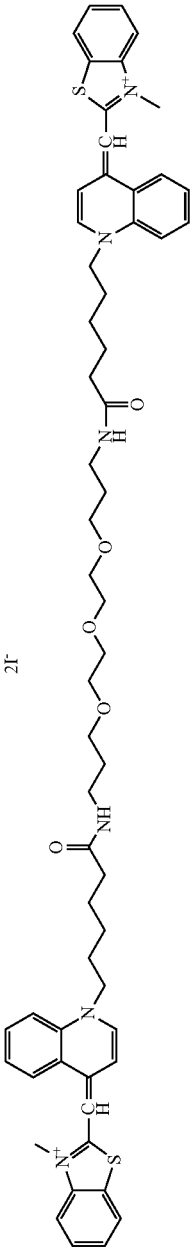 | 1248 | 27 |

TABLE 2-continued

Prepared Fluorescent Nucleic Acid Dyes

| No. Name | Structure | MWt. | SPACER LENGTH (ATOMS) |
|---|---|---|---|
| 30 STST-27 | | 1116 | 27 |
| 31 STST-19 | | 1000.8 | 19 |
| 32 AOAO-47 | | 1547.6 | 47 |

TABLE 2-continued
Prepared Fluorescent Nucleic Acid Dyes
| No. | Name | Structure | MWt. | SPACER LENGTH (ATOMS) |
|---|---|---|---|---|
| 33 | AOAO-67 | 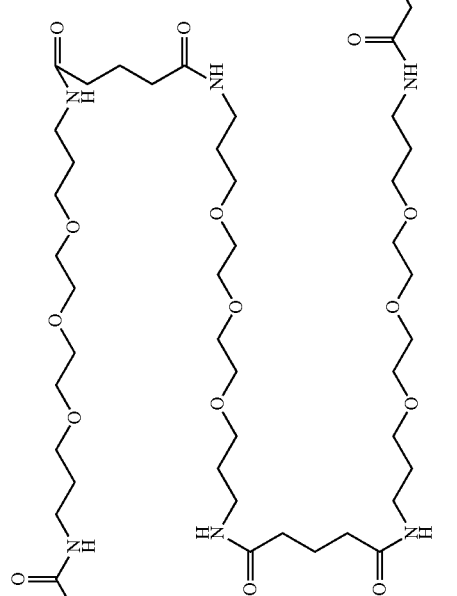 | 1864 | 67 |

TABLE 2-continued
Prepared Fluorescent Nucleic Acid Dyes
| No. | Name | Structure | MWt. | SPACER LENGTH (ATOMS) |
|---|---|---|---|---|
| 33 | AOAO-113 | 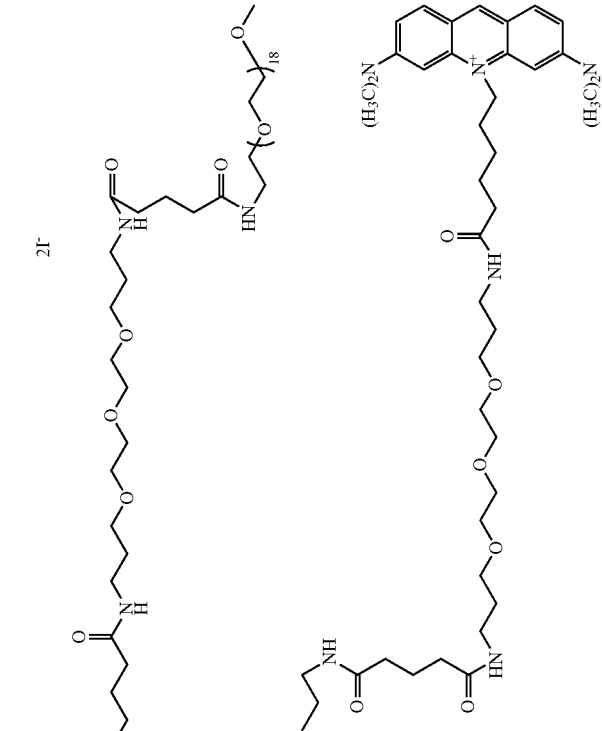 | 2541 | 113 |

TABLE 2-continued

Prepared Fluorescent Nucleic Acid Dyes

| No. Name | Structure | MWt. | SPACER LENGTH (ATOMS) |
|---|---|---|---|
| 35 ET-27 | (structure with 2r counterion) | 1239 | 27 |
| 36 STSF-21N | (structure with 2r counterion) | 1041 | 21 |

While many of the structures shown in Table 2 show one or more iodide anion(s), any other appropriate anion(s), such as those described herein, such as chloride anion(s), merely by way of example, may be used in place of the iodide anions shown.

A dimeric dye of the invention may comprise a fluorescent nucleic acid dye $Q_1$ and a fluorescent nucleic acid dye $Q_2$, wherein $Q_1$ and $Q_2$ may be the same or different. When $Q_1$ and $Q_2$ are the same, the resulting dye is a homodimer, such as any of Dye Nos. 6-22, 24-26, and 28-36 of Table 2, merely by way of example. When $Q_1$ and $Q_2$ are different fluorescent nucleic acid dyes that have similar absorption and emission spectra, the resulting dimer is a heterodimer, such as that of Dye No. 23 of Table 2, merely by way of example. Such a heterodimer is functionally similar to a homodimer. In either case, both $Q_1$ and $Q_2$ are reporter dyes, such that upon DNA binding, they both contribute to the detected fluorescent signal, as schematically illustrated in Combination A of FIG. 10. Alternatively, a heterodimeric dye may comprise two different fluorescent nucleic acid dyes that have substantially different absorption and emission spectra. In this case, only one of the two dyes is selected as a reporter dye.

$Q_1$ and $Q_2$ may form a fluorescence resonance energy transfer (FRET) pair. In this case, the dye with the shorter wavelength acts as a fluorescence donor dye, while the dye with the longer wavelength acts as an acceptor or reporter dye. For efficient FRET to occur, the emission spectrum and the absorption of the donor dye need to overlap sufficiently. Further discussions of FRET are provided in Förster, *Ann. Phys.* (1948) and Stryer, et al., *Proc. Natl. Acad. Sci.* (1967). A FRET-based dye allows for excitation at one wavelength and re-emission of fluorescence at a substantially longer wavelength.

When a heterodimer comprising $Q_1$ and $Q_2$ of substantially different spectra is not a FRET-based dye, either one of $Q_1$ and $Q_2$, but not both at the same time, may be selected as a reporter dye. The other non-reporter dye serves as a partner for the necessary intramolecular dimer formation and provides additional nucleic acid binding ability for the dimeric dye. An example of a heterodimeric dye having one reporter dye, a fluorescent nucleic acid dye $Q_1$, and one non-reporter dye, a non-fluorescent nucleic acid-binding molecule $Q_2$, is schematically illustrated in Combination B of FIG. 10.

A heterodimeric dye may comprise a non-fluorescent nucleic acid-binding molecule $Q_1$ and a fluorescent non-nucleic acid dye $Q_2$. Here, $Q_2$ is the reporter dye, while $Q_1$ serves as a DNA anchoring dye and a pairing partner for the necessary intramolecular dimer formation. The DNA binding mode for this type of heterodimer is schematically illustrated in Combination C of FIG. 10.

A heterodimeric dye may comprise a fluorescent nucleic acid dye $Q_1$ and a non-fluorescent non-nucleic acid dye $Q_2$. In such a case, $Q_1$ is the reporter dye and $Q_2$ serves as a partner for the necessary intramolecular dimer formation. The DNA binding mode for this type of heterodimer is schematically illustrated in Combination D of FIG. 10.

A heterodimeric dye may comprise a fluorescent nucleic acid dye $Q_1$ and a fluorescent non-nucleic acid dye $Q_2$. If $Q_1$ and $Q_2$ have similar absorption and emission spectra, both $Q_1$ and $Q_2$ are reporter dyes, although only $Q_1$ is bound to the nucleic acids. The DNA binding mode for this type of heterodimer is schematically illustrated in Combination E of FIG. 10. When $Q_1$ and $Q_2$ form a FRET pair, the dye with the shorter wavelength acts as the fluorescence donor dye, while the dye with the longer wavelength acts as the acceptor or reporter dye. When $Q_1$ and $Q_2$ are substantially different in spectra and are not a FRET pair, either one of $Q_1$ and $Q_2$, but not both at the same time, may be selected as a reporter dye. An example of this latter case is the heterodimer AORO-7 (Dye No. 27 of Table 2), which comprises AO with an absorption peak and an emission peak at 503 nm and 523 nm (DNA), respectively, and a rosamine dye with an absorption peak and an emission peak and at 600 nm and ~620 nm, respectively, as shown in FIGS. 12 and 13. FIG. 14 shows a PCR amplification plot using AORO-7, with the fluorescent non-nucleic rosamine dye component chosen as the reporter dye by using channel no. 3 on an iCycler IQ Multiple-Color Real-Time PCR Detection System from Bio-Rad Laboratories (Hercules, Calif.).

A dimeric dye may comprise a pair of monomeric dyes selected from two identical fluorescent nucleic acid dyes and two different fluorescent nucleic acid dyes.

A trimeric dye may comprise a fluorescent nucleic acid dye $Q_1$, a fluorescent nucleic acid dye $Q_2$, a fluorescent nucleic acid dye $Q_3$, wherein $Q_1$, $Q_2$ and $Q_3$ may be the same or different. For example, $Q_1$, $Q_2$, and $Q_3$ may be the same fluorescent nucleic acid dye. A trimeric dye may comprise a fluorescent nucleic acid dye $Q_1$, a fluorescent nucleic acid dye $Q_2$, and a fluorescent non-nucleic acid dye $Q_3$, wherein $Q_1$ and $Q_2$ serve as DNA anchoring molecules and $Q_3$ is a reporter dye. A trimeric dye of the invention may comprise a non-fluorescent nucleic acid-binding molecule $Q_1$, a non-fluorescent nucleic acid-binding molecule $Q_2$, and a third fluorescent non-nucleic acid dye $Q_3$, wherein $Q_1$ and $Q_2$ serve as DNA anchoring molecules and $Q_3$ is a reporter dye.

Fluorescent nucleic acid dyes, non-fluorescent nucleic acid-binding molecules, fluorescent non-nucleic acid dyes, non-fluorescent non-nucleic acid dyes, and examples thereof, are further described below.

Fluorescent Nucleic Acid Dyes

Examples of a monomeric fluorescent nucleic acid dye suitable for constructing dyes include, but are not limited to, an acridine dye, an asymmetric cyanine-based nucleic acid stain, a phenanthridinium dye, a symmetric cyanine nucleic acid stain, a derivative of DAPI, and a derivative of a Hoechst dye. DAPI and Hoechst dyes generally cannot be directly attached to BRIDGE because they do not possess a reactive group for bond formation. In this context, a derivative refers to a base dye, such as DAPI or a Hoechst dye, that is modified sufficiently for bond formation, such as by addition of a reactive group, by way of example.

Acridine Dyes

Merely by way of example, the monomeric fluorescent nucleic acid dye may be an acridine dye having the general structure (Structure 4) set forth directly below.

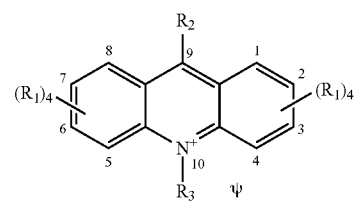

Structure 4

Acridine orange (AO) is an acridine dye that stains dsDNA with green fluorescence and stains RNA with red fluorescence. Traganos, et al., *J. Histochem. Cytochem.* 25(1), 46 (1977). Unlike some other acridine dyes, AO has a high extinction coefficient (>50,000) and a long absorption wavelength ($\lambda_{abs}$=500 nm (DNA bound)). However, the affinity of AO for nucleic acid is very low and the dye has significant intrinsic fluorescence in the absence of nucleic acids. In this regard, the level of intrinsic fluorescence may be significant in that it precludes the dye from being used in detecting nucleic acid at a low level, such as in the low nanogram/mL range, for example, or in detecting nucleic acid in gels without a destaining step, for example. Consequently, AO itself is of little utility for DNA or RNA quantification, particularly for highly sensitive DNA detection associated with applications such as real-time qPCR.

An acridine dye may comprise any of a variety of substituents at various positions on the ring structure. The nature of a substituent and its substitution position may strongly affect the spectral properties of the dye produced. In general, electron-donating substituents at the 3- and 6-positions and an electron-withdrawing substituent at the 9-position typically red-shift the absorption and emission spectra of the dye. Examples of a typical electron-donating group include, but are not limited to, an amino group, a hydroxyl group, an alkoxy group, and an alkylmercapto group. Examples of a typical electron-withdrawing group include, but are not limited to, a cyano group, a perfluoroalkyl group, a carboxamido group, a sulfonamide group, a nitro group, and a halogen group. Any additional ring structure fused with the core structure will also increase the wavelengths of the dye produced.

Various portions of Structure 4 are now described. In Structure 4, as in various other monomeric dye structures provided or described herein, a symbol of "R" followed by a subscript, such as $R_1$, merely by way of example, may indicate a substituent of the structure that is not part of BRIDGE, or may represent where BRIDGE attaches to the structure, in which case, it is not a substituent of the structure. Each $R_1$, independently, may be H; an alkyl or alkenyl having 1 carbon to 6 carbons; a halogen; —$OR_4$; —$SR_5$; —$NR_6R_7$; —CN; —NH(C=O)$R_8$; —NHS(=O)$_2$$R_9$; or —C(=O)NHR$_{10}$; any adjacent pair of $R_1$s optionally forms a 5- or 6-membered saturated or unsaturated ring, which further optionally comprises at least one hetero atom selected from N, O and S; and one of the $R_1$s is -L-$R_r$, as previously described, or one of the $R_1$s represents where BRIDGE attaches to the structure, in which case, that $R_1$ is merely representative and not actually a substituent of the monomeric dye. In any case where $R_1$ involves at least one of $R_4$, $R_5$, $R_6$, $R_7$, $R_8$, $R_9$, and $R_{10}$, any applicable one of same is independently H or an alkyl having 1 carbon to 6 carbons, and for any applicable pair of adjacent $R_6$ and $R_7$, independently, $R_6$ and $R_7$ may in combination form a 5- or 6-membered saturated or unsaturated ring, which optionally comprises at least one hetero atom selected from N and O.

Typically, $R_2$ is H; an alkyl or alkenyl having 1 carbon to 6 carbons; an aryl optionally comprising at least one hetero atom selected from halogens, N, O and S; a halogen; —$OR_{11}$; —$SR_{12}$; —$NHR_{13}$; —CN; or —C(=O)NHR$_{14}$; or represents where BRIDGE attaches to the structure. In any case where $R_2$ involves at least one of $R_{11}$, $R_{12}$, $R_{13}$ and $R_{14}$, any applicable one of same is independently H or alkyl having 1 carbon to 6 carbons.

Typically, $R_3$ is H; or an alkyl having 1 carbon to 6 carbons; or represents where BRIDGE attaches to the structure.

$\Psi$ is an anion, such as an anion that balances positive charge(s) associated with the dye, for example. $\Psi$ may be biologically compatible. Examples of a suitable anion include, but are not limited to, a halide, a sulfate, a phosphate, a perchlorate, a tetrafluoroborate, and a hexafluorophosphate. Merely by way of example, the anion may be chloride or iodide.

Only one of $R_1$, $R_2$ and $R_3$ must represent where BRIDGE attaches to the structure. Merely by way of example, one of $R_2$ and $R_3$ may represent where BRIDGE attaches to the structure. As described herein, BRIDGE may be covalently linked to a monomeric acridine dye, such as any such dye described herein, and to another suitable monomeric dye, to form a dimeric dye, or to two other suitable monomeric dyes to form a trimeric dye. Generally, only one of $R_1$, $R_2$ and $R_3$ may be optionally -L-$R_r$, as previously described. A dimeric dye or a trimeric dye may comprise only one -L-$R_r$.

Merely by way of example, the monomeric acridine dye may have the structure (Structure 5) set forth directly below.

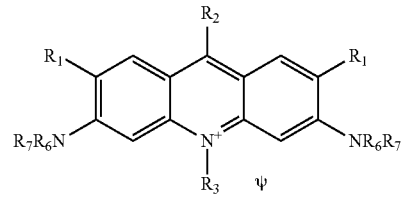

Structure 5

In Structure 5, generally, each $R_1$, independently, is H, or a C1-C2 alkyl; one of $R_2$ and $R_3$ represents where BRIDGE attaches to the structure; optionally, one of $R_2$ and $R_3$ is -L-$R_r$, as previously described; when $R_2$ does not represent where BRIDGE attaches to the structure and is not L-$R_r$, $R_2$ is selected from H, —$CH_3$, —$NH_2$, —$NHCH_3$, —CN, and —C(=O)$NH_2$; when $R_3$ does not represent where BRIDGE attaches to the structure and is not L-$R_r$, $R_3$ is selected from H or —$CH_3$; each of $R_6$ and $R_7$, independently, is H, or a C1-C2 alkyl; and $\Psi$ is an anion, as previously described. Merely by way of example, for each pair of adjacent $R_6$ or $R_7$ and $R_1$, independently, $R_6$ or $R_7$ and $R_1$ may in combination form a 5- or 6-membered, saturated or unsaturated ring.

In one example, the monomeric acridine dye, as represented by Structure 5, may be such that each $R_1$ is H; $R_2$ is H; $R_3$ represents where BRIDGE attaches to the structure; each $R_6$ is —$CH_3$; each $R_7$ is —$CH_3$; and $\Psi$ is an anion, as previously described.

Merely by way of example, a dimeric dye may comprise two identical monomeric acridine dye molecules of Structure 5 and BRIDGE of Formula 5.

Asymmetric Cyanine Dyes

Merely by way of example, the monomeric fluorescent nucleic acid dye may be an asymmetric cyanine dye having the general structure (Structure 6) set forth directly below.

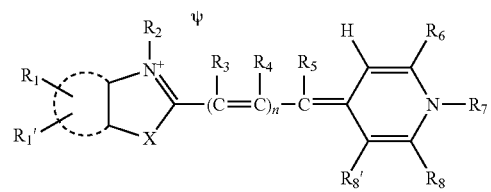

Structure 6

The general structure (Structure 6, above) of asymmetric cyanine dyes comprises a heterocyclic ring that is a substituted benzazolium ring; a methane or polymethine bridge; and a heterocyclic ring that is a substituted pyridinium or quinolinium ring. The dotted line in the structure represents the atoms necessary to form one or more fused aromatic ring(s), optionally incorporating one or more nitrogen(s), which may or may not be quaternized. When the dotted line represents a 6-membered ring comprising one or more nitrogen atom(s), the resulting fused ring is called an azabenzole ring.

In Structure 6, in general, each of $R_1$ and $R_1'$ on the benzazolium ring, independently, is H; alkyl or alkenyl having 1 carbon to 6 carbons; a halogen; —$OR_9$; —$SR_{10}$; —$NR_{11}R_{12}$; —CN; —NH(C=O)$R_{13}$; —NHS(=O)$_2R_{14}$; or —C(=O)NH$R_{15}$. Merely by way of example, one of $R_1$ and $R_1'$ may be a substituent that is meta to X or to the benzazole nitrogen, wherein the substituent confers at least one desirable property as further described below. In any case where $R_1$ or $R_1'$ involves at least one of $R_9$, $R_{10}$, $R_{11}$, $R_{12}$, $R_{13}$, $R_{14}$ and $R_{15}$, any applicable one of same, independently, is H; or alkyl having 1 carbon to 12 carbons, optionally incorporating 1 to 2 nitrogen(s); or an aryl; and any applicable $R_{11}$ and $R_{12}$ may in combination form a 5- or 6-membered saturated or unsaturated ring, which optionally comprises at least one hetero atom selected from N and O.

As mentioned above, one of $R_1$ and $R_1'$ of Structure 6 may be a substituent that confers at least one desirable property to the dye. One such desirable property is DNA minor groove-binding. A minor groove-binding molecule typically has a structure with a crescent shape that fits into the minor groove of a double-stranded DNA. Examples of a DNA minor groove-binding dye molecule or non-dye molecule, which may include a natural molecule, include, but are not limited to, DAPI, a Hoechst dye, distamycin A, netropsin, and any of numerous synthetic minor groove-binders based on polyamides of N-methylpyrrole and N-methylimidazole. Catalog of Biotium, Inc. (Hayward, Calif. (CA)), 2005-2006; Boger, et al., *Acc. Chem. Res.* 37, 61 (2004); and Dervan, P. B., *Bioorg. & Med. Chem.* 9, 2215 (2001). The crescent shape of a minor groove-binder is typically created by meta-substitution of a 5- or 6-membered ring with a minor groove-binder substituent, which includes, but is not limited to, a substituted or an unsubstituted benzoxazol-2-yl, a substituted or an unsubstituted benzimidazol-2-yl, a substituted or an unsubstituted benzothiazol-2-yl, a substituted or an unsubstituted imidazol-2-yl, a substituted or an unsubstituted oxazol-2-yl, a substituted or an unsubstituted thiazol-2-yl, a substituted or an unsubstituted N-methylpyrrolyl-2-aminocarbonyl, a substituted or an unsubstituted N-methylpyrrolyl-3-carboxamido, a substituted or an unsubstituted 1-methylimidazol-2-carboxamido, a substituted or an unsubstituted 1-methylimidazol-4-aminocarbonyl, a substituted or an unsubstituted phenyl, a substituted or an unsubstituted pyridyl, a substituted or an unsubstituted pyrazinyl, and a substituted or an unsubstituted triazinyl. A DNA dye may be meta-substituted by a minor groove-binder substituent as described in U.S. Patent Application Publication No. 2004/0132046.

One of $R_1$ and $R_1'$ may be -L-$R_r$, as previously described. One of $R_1$ and $R_1'$ may represent where BRIDGE attaches to the structure.

X is selected from O and S. In general, a dye wherein X is S has longer absorption and emission wavelengths than a similar dye wherein X is O.

$R_2$ may be methyl or ethyl, or may represent wherein BRIDGE attaches to the structure. Merely by way of example, $R_2$ may be methyl or ethyl.

The subscript n represents a number of double bond units in any methine bridge and is selected from 0, 1, and 2. Typically, a dye with a longer methine bridge will have longer wavelengths than a dye with a shorter methine bridge. Merely by way of example, n may be 0 or 1.

Substitutents $R_3$, $R_4$, and $R_5$ are independently H or —$CH_3$. Optionally, any adjacent pair of these substitutents may form a 5- or 6-membered ring. Merely by way of example, $R_3$, $R_4$, and $R_5$ may be H.

In general, independently, each of substituents $R_6$, $R_8$, and $R_8'$ may be H; an alkyl or alkenyl having 1 carbon to 10 carbons, optionally comprising at least one hetero atom selected from N, O, and S; a halogen; —$OR_{16}$; —$SR_{16}$; —$NR_{16}R_{17}$; a substituted or unsubstituted aryl, optionally comprising 1 to 3 hetero atom(s) selected from halogens, N, O, and S. $R_8$ and $R_8'$ may in combination form a fused aromatic ring, which may be further substituted 1 to 4 time(s), independently, by C1-C2 alkyl, C1-C2 alkoxy, C1-C2 alkylmercapto, or a halogen. In any case in which any of $R_6$, $R_8$, and $R_8'$ involve at least one of $R_{16}$ and $R_{17}$, any applicable one of same, independently, is H; or alkyl having 1 carbon to 12 carbons, optionally incorporating 1 to 2 nitrogen(s); or an aryl; and any applicable $R_{16}$ and $R_{17}$ may in combination form a 5- or 6-membered saturated or unsaturated ring, which optionally comprises at least one hetero atom selected from N and O.

$R_6$ may represent where BRIDGE attaches to the structure. $R_6$ may be a -L-$R_r$, as previously described.

$R_7$ is selected from H; an alkyl or alkenyl having 1 carbon to 10 carbons, optionally comprising an aryl and at least one hetero atom selected from N, O, and S; a substituted or unsubstituted aryl optionally comprising 1 to 3 hetero atom(s) selected from halogens, N, O, and S; a -L-$R_r$, as previously described; or may represent where BRIDGE attaches to the structure.

Ψ is an anion, as previously described herein.

Only one of $R_1$, $R_1'$, $R_6$, $R_7$ and $R_8$ must represent where BRIDGE attaches to the structure. As described herein, BRIDGE may covalently link the monomeric asymmetric cyanine dye and another suitable monomeric dye to form a dimeric dye, or the monomeric asymmetric cyanine dye and two other suitable monomeric dyes to form a trimeric dye. Generally, only one of $R_1$, $R_1'$, $R_6$, $R_7$ and $R_8$ may optionally be -L-$R_r$, as previously described. More typically, a dimeric dye or a trimeric dye may comprise only one -L-$R_r$.

Merely by way of example, an asymmetric cyanine dye may have the structure (Structure 7) set forth directly below, wherein each of $R_1'$, $R_6$, $R_7$, $R_8$ and $R_8'$ is as previously described in connection with Structure 6.

Structure 7

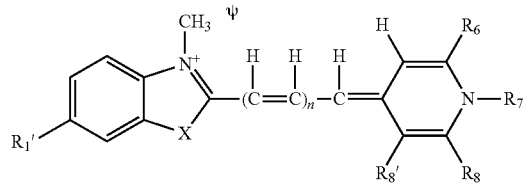

By way of example, the asymmetric cyanine dye, as represented by Structure 7, may be such that $R_1'$ is H; alkyl or alkenyl having 1 carbon to 6 carbons; a halogen; —$OR_9$; —$SR_{10}$; —$NR_{11}R_{12}$; —CN; —NH(C=O)$R_{13}$; —NHS(=O)$_2R_{14}$; —C(=O)NH$R_{15}$; a substituent associated with minor groove binding; or -L-$R_r$, as previously described; or represents where BRIDGE attaches to the structure. Further, when $R_1'$ comprises at least one of $R_9$, $R_{10}$, $R_{11}$, $R_{12}$, $R_{13}$, $R_{14}$ and $R_{15}$, any said one of $R_9$, $R_{10}$, $R_{11}$, $R_{12}$, $R_{13}$, $R_{14}$ and $R_{15}$, independently, is H or alkyl having 1 carbon to 12 carbons, optionally incorporating 1 to 2 nitrogen(s), or an aryl; and when $R_1'$ comprises $R_{11}$ and $R_{12}$, $R_{11}$ and $R_{12}$ may in combination form a 5- or 6-membered, saturated or unsaturated ring, which optionally comprises at least one hetero atom selected from N and O. X may be selected from O and S and n may be selected from 0, 1, and 2. $R_6$ may be H; alkyl or alkenyl having 1 carbon to 10 carbons, optionally comprising at least one hetero atom selected from N, O, and S; a halogen; —$OR_{16}$; —$SR_{16}$; —$NR_{16}R_{17}$; a substituted or an unsubstituted aryl, optionally comprising 1 to 3 hetero atom(s) selected from halogens, N, O, and S; or -L-$R_r$, as previously described; or may represent where BRIDGE attaches to the structure. $R_7$ may be H; alkyl or alkenyl having 1 carbon to 10 carbons, optionally comprising an aryl and at least one hetero atom selected from N, O, and S; a substituted or an unsubstituted aryl optionally comprising 1 to 3 hetero atom(s) selected from halogens, N, O, and S; or -L-$R_r$, as previously described; or may represent where BRIDGE attaches to the structure. $R_8$ may be H; alkyl or alkenyl having 1 carbon to 10 carbons, optionally comprising at least one hetero atom selected from N, O, and S; a halogen; —$OR_{16}$; —$SR_{16}$; —$NR_{16}R_{17}$; or a substituted or an unsubstituted aryl, optionally comprising 1 to 3 hetero atom(s) selected from halogens, N, O, and S; or -L-$R_r$, as previously described; or may represent where BRIDGE attaches to the structure. $R_8'$ may be H; alkyl or alkenyl having 1 carbon to 10 carbons, inclusive, optionally comprising at least one hetero atom selected from N, O, and S; a halogen; —$OR_{16}$; —$SR_{16}$; —$NR_{16}R_{17}$; or a substituted or an unsubstituted aryl, optionally comprising 1 to 3 hetero atom(s) selected from halogens, N, O, and S. $R_8$ and $R_8'$ may in combination form a fused aromatic ring, which may be further substituted 1 to 4 time(s), independently, by C1-C2 alkyl, C1-C2 alkoxy, C1-C2 alkylmercapto, or a halogen. For any $R_6$, $R_8$, or $R_8'$ that comprises at least one of $R_{16}$ and $R_{17}$, any said one of $R_{16}$ and $R_{17}$ thereof, independently, may be H; alkyl having 1 carbon to 12 carbons, optionally incorporating 1 to 2 nitrogen(s) or an aryl. For any $R_6$, $R_8$, and $R_8'$ that comprises $R_{16}$ and $R_{17}$, $R_{16}$ and $R_{17}$ thereof may in combination form a 5- or 6-membered saturated or unsaturated ring, which optionally comprises at least one hetero atom selected from N and O. Only one of $R_1'$, $R_6$, $R_7$ and $R_8$ represents where BRIDGE attaches to the structure. Generally, only one of $R_1'$, $R_6$, $R_7$ and $R_8$ may optionally be -L-$R_r$, as previously described. $\Psi$ is an anion, as previously described.

In one example, an asymmetric cyanine dye has the structure (Structure 8) set forth directly below, wherein $R_7$ represents where BRIDGE attaches to the structure and $\Psi$ is an anion, as previously described.

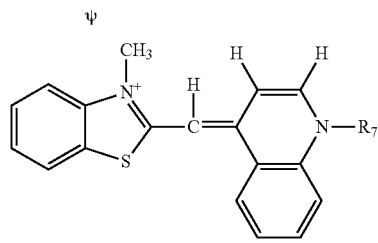

Structure 8

Merely by way of example, a dimeric dye may comprise two identical monomeric asymmetric cyanine dye molecules of Structure 8 and BRIDGE of Formula 5.

Merely by way of example, in a fluorescent nucleic acid dye, such as that of Structure 1, for example, when the $Q_1$ dye constituent is an asymmetric cyanine dye, such as any of Structures 6-8, for example, and the $Q_2$ dye constituent is an asymmetric cyanine dye, such as any of Structures 6-8, for example, a sum of a, b, c, d, e, f, g, h, and i of BRIDGE, such as BRIDGE of Formula 1, for example, may be greater than three, or at least one of $A^1$, $A^2$, $A^3$, $A^4$, $A^5$, $A^6$, $A^7$, $A^8$, $A^9$, and $A^{10}$ of BRIDGE, such as BRIDGE of Formula 1, for example, may be a NABEG comprising a moiety that comprises at least one bond linkage that comprises at least one amide bond, urethane bond, urea bond, or thiourea bond; or an aryl optionally comprising at least one hetero atom selected from halogens, N, O, and S.

Phenanthridinium Dyes

Merely by way of example, the monomeric fluorescent nucleic acid dye may be a phenanthridinium derivative, having the general structure (Structure 9) set forth directly below.

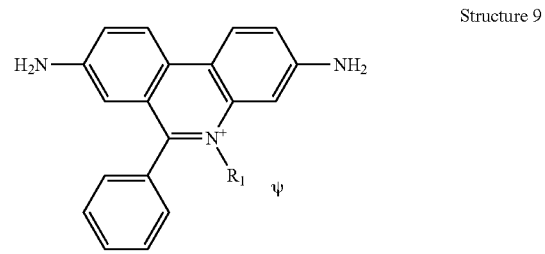

Structure 9

In general, $R_1$ may represent where BRIDGE attaches to the structure, although it will be understood that many variations of Structure 9 above are possible and contemplated herein, via a variety of techniques, such as synthesis techniques that may provide for the attachment of BRIDGE to the structure elsewhere or that may modify the structure to provide a dye with any of various desirable wavelengths. $\Psi$ is an anion, as previously described.

Merely by way of example, two monomeric phenanthridinium dye molecules of Structure 9 in combination with BRIDGE of Formula 5 may form a dimeric dye.

Merely by way of example, the monomeric fluorescent nucleic acid dye may be a xanthene derivative, having the general structure (Structure 10) set forth directly below.

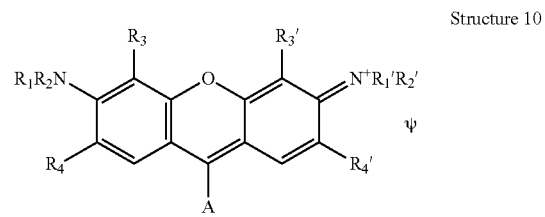

Structure 10

Certain cationically charged xanthene dyes are known to bind to nucleic acids. For example, pyronin Y, in which $R_1$, $R_2$, $R_1'$, and $R_2'$ are methyl and $R_3$, $R_3'$, $R_4$, $R_4'$, and A are H, is a known fluorescent DNA binding dye that has been used for DNA gel staining Adkin, S., and Burmeister, M., *Anal. Biochem.* 240(1), 17 (1996). A dye having the general skeleton shown in Structure 10 above is expected to have similar nucleic acid staining properties and to provide other fluorescent colors. For example, pyronin Y has an absorption maximum at 548 nm and an emission maximum at 565 nm, providing a red fluorescent color.

Merely by way of example, in general, each of $R_1$, $R_2$, $R_1'$, and $R_2'$, independently, may be H, or C1-C6, inclusive, alkyl, optionally incorporating 1 to 2 hetero atom(s) selected from N and O. Further merely by way of example, independently, at least one of the pair $R_1$ and $R_2$ and the pair $R_1'$ and $R_2'$ may in combination form a 5- or 6-membered ring, optionally comprising one hetero atom selected from N and O. $R_1$ and $R_1'$ may be the same and $R_2$ and $R_2'$ may be the same.

One of $R_1$, $R_2$, $R_1'$, and $R_2'$ may represent where BRIDGE attaches to the structure. Optionally, one of $R_1$, $R_2$, $R_1'$, and $R_2'$ is -L-$R_r$, as previously described.

Merely by way of example, $R_3$, $R_3'$, $R_4$, and $R_4'$, independently, may be H or C1-C3, inclusive, alkyl. $R_3$, $R_3'$, $R_4$, and $R_4'$ may be the same. Independently, at least one of the pair $R_3$ and $R_1$, the pair $R_2$ and $R_4$, the pair $R_3'$ and $R_1'$, and the pair $R_4$ and $R_2'$ may in combination form a 5- or 6-membered ring, which may be saturated or unsaturated, substituted or unsubstituted.

A is a C1-C3 alkyl; or -L-$R_r$, where L is a C1-C12 aliphatic linker and $R_r$ is a reactive group, as previously described; or represents where BRIDGE attaches to the structure.

Only one of $R_1$, $R_2$, $R_1'$, $R_2'$ and A may represent where BRIDGE attaches to the structure.

Ψ is an anion, as previously described.

Two monomeric xanthene dye molecules of Structure 10 in combination with BRIDGE of Formula 5 may form a dimeric dye.

Other monomeric fluorescent nuclei acid stains, such as DAPI, DIPI, a Hoechst dye, LDS 751, hydroxystilbamidine, a styryl dye, a merocyanine dye, a cyanine dye, or Fluoro-Gold, merely by way of example, may be suitable for use or may be derivatized to be suitable for use as described herein. Haugland, R. P., *Handbook of Fluorescent Probes and Research Products*, 9$^{th}$ edition. It will be understood that a large number of other monomeric nucleic acid dyes may be suitable for use or may be derivatized to be suitable for use as described herein. The dyes may either be directly conjugated to BRIDGE or be derivatized so that they can be conjugated to BRIDGE using synthesis knowledge.

Non-Fluorescent Nucleid Acid Dyes

In general, non-fluorescent nucleic acid-binding molecules are nucleic acid-binding molecules that are non-fluorescent or are too weakly fluorescent to be useful as fluorescent nucleic acid dyes. Non-fluorescent nucleic acid-binding molecules include non-fluorescent nucleic acid-binding dyes and colorless synthetic or natural nucleic acid-binding molecules.

A number of non-fluorescent dyes have been used as colorimetric nucleic acid gel stains. Relative to the fluorescent nucleic acid stain ethidium bromide, these non-fluorescent dyes usually have much lower detection sensitivity, but are considered to be safer to use, such as safer in terms of toxicity for use by humans, for example. Examples of non-fluorescent nucleic acid-binding dyes include, but are not limited to, Nile Blue, Crystal Violet, Methylene Blue, Thionin, Methyl Green, Basic Blue 66, Basic Red 29, Indoline Blue, Safranin O, Janus Green B, Pinacyanol, and Stains-All. Adkins, et al., *Anal. Biochem.* 240, 17 (1996). Most of these dyes are available from Aldrich Chemical Company, Inc. (Milwaukee, Wis.).

Fluorescent Non-Nucleic Acid Dyes

One of the monomeric dyes $Q_1$, $Q_2$, and $Q_3$ may be a fluorescent non-nucleic acid dye. In general, all fluorescent dyes that are not normally considered fluorescent nucleic acid dyes are considered fluorescent non-nucleic acid dyes. Herein, the term "fluorescent non-nucleic acid dye" generally refers to a fluorescent dye that is not normally considered a nucleic acid dye. By way of example, the dye may not normally be considered a fluorescent minor groove-binder or a fluorescent intercalator. Further by way of example, while some fluorescent non-nucleic acid dyes may exhibit some weak interactions with nucleic acids, these interactions are generally not sufficient to cause significant fluorescence spectral changes to make the dyes useful for nucleic acid detection.

Various fluorescent non-nucleic acid dyes are commercially available from various sources, such as Biotium, Inc. (Hayward, Calif.). Examples of a fluorescent non-nucleic acid dye include, but are not limited to, a fluorescein dye, a sulfonated fluorescein dye, a rhodamine dye, a sulfonated rhodamine dye, a cyanine dye, a sulfonated cyanine dye, a coumarine dye, a pyrene dye, an oxazine dye, and a Bodipy dye (Molecular Probes, Inc. (Eugene, Oreg.)). A suitable fluorescent non-nucleic acid dye may comprise a reactive group $R_r$, as previously described. A suitable fluorescent non-nucleic acid dyes may be derived such that it comprises a reactive group $R_r$. A suitable reactive dye is covalently attached to BRIDGE via $R_r$ and a suitable functional group from BRIDGE.

Selection of a suitable fluorescent non-nucleic acid dye may depend on the other pairing monomeric dye or dyes. In general, a suitable fluorescent non-nucleic acid dye should be able to form an intramolecular dimer with the pairing dye or dyes. Intramolecular dimer formation is typically confirmed by a significant change in the absorption spectrum of at least one of the component monomeric dyes in an aqueous media before and after the monomeric dye is covalently linked to the other pairing monomeric dye or dyes by BRIDGE.

Non-Fluorescent Non-Nucleic Acid Dyes

In general, the term "non-fluorescent non-nucleic acid dye" refers to a dye that is neither fluorescent nor nucleic acid-binding. Such a dye is generally used as a fluorescence quencher in a FRET-based application. By way of example, a fluorogenic peptidase substrate has been constructed by covalently attaching a fluorescent donor dye to one end of a peptide, and a non-fluorescent non-nucleic acid dye, the quencher, to the other end of the peptide to quench the fluorescence of the donor. Upon enzymatic cleavage of the peptide, the donor and the quencher are separated, thereby releasing the fluorescence signal. Further by way of example, a non-fluorescent non-nucleic acid dye has been used to design so-called TaqMan probes for qPCR. A TaqMan probe consists of an oligonucleotide, which is complimentary to a target DNA sequence, a fluorescence donor dye attached to one end of the oligonucleotide, and a quencher attached to the other end of the oligonucleotide to quench the fluorescence of the donor dye. During real-time PCR, the labeled oligonucleotide binds to the target DNA, which causes the oligonucleotide to be enzymatically cleaved, thereby generating a fluorescent signal.

A non-fluorescent non-nucleic acid dye may be used mainly as a pairing partner for intramolecular dimer formation, which is responsible for the release-on-demand DNA-binding mechanism. The non-fluorescent non-nucleic acid dye should be so chosen to ensure minimal FRET between it and the fluorescent nucleic acid-binding dye it pairs with following DNA binding. In general, fluorescence loss of the fluorescent nucleic acid dye due to FRET should be minimal, such as no more than about 70% of the total emitted fluorescence, for example. The selection of the non-fluorescent non-nucleic acid dye may be based on an evaluation of the emission spectrum of the fluorescent nucleic acid-binding dye and the absorption spectrum of the non-fluorescent dye. Ideally, these spectra should have minimal overlap so that the fluorescence signal loss due to FRET is minimal, as described above. Another possible way to minimize FRET is to use sufficiently long BRIDGE so that the fluorescence signal loss due to FRET is minimal, as described above, as the efficiency of FRET is dependent on the inverse sixth power of the intermolecular separation between the constituent dyes.

Examples of commercially available non-fluorescent quenchers which may be useful include, but are not limited to, DABCYL from Fluka (Buchs, Switzerland), Black Hole Quencher (BHQ) from Biosearch Technologies, Inc. (Novato, Calif.), Eclipse Dark Quencher (DQ) from Epoch Biosciences (Bothell, Wash.), IOWA Black (IWB) from Integrated DNA Technologies (Skokie, Ill.), and QSY from Molecular Probes, Inc. (Eugene, Oreg.).

Method of Use

A nucleic acid dye described herein may be particularly useful in quantitative real-time PCR (qPCR). Using PCR coupled with fluorescence-based DNA detection via a fluorescent nucleic acid dye, one may determine the amount of a product of a PCR process without having to stop a PCR run or to sample the reaction during a PCR run. Using qPCR, one may not only quantify the original amount of a DNA sample, but may also obtain sequence information. The sensitivity and specificity of qPCR makes it highly useful in a number of practical applications including the diagnosis and prognosis of diseases, and the identification of species in agriculture and forensic science.

The use of a dye in qPCR may involve adding a solution of the dye and other components suitable for a PCR reaction (such as an amplification enzyme or enzymes, a primer or primers sufficient for amplification of the target nucleic acid sequence, and deoxynucleoside triphosphates, for example) to a solution comprising a DNA sample in a tube, placing the sealed tube in a qPCR instrument, and recording the detected fluorescent signal. The Ct value, or the number of cycles required for the fluorescence signal to reach an arbitrarily determined threshold value, may be recorded. The Ct value is linearly related to the log of the DNA sample copy number. Using a standard plot of Ct value and the log of DNA copy number, one can determine the DNA copy number of a DNA sample based on the Ct value. Merely by way of example, PCR amplification plots using selected dyes are shown in FIGS. 8, 9, 11, and 14.

Other uses of a fluorescent nucleic acid dye include, but are not limited to, DNA quantitation in solutions or gels, staining of nucleic acids in live or dead cells, and nucleic acid detection in microarrays. Generally, the use of a fluorescent nucleic acid dye may comprise contacting the dye, optionally in combination with any additional reagent(s), with a sample that comprises or is thought to comprise a nucleic acid polymer; incubating the resulting mixture of dye and sample for a sufficient amount of time to allow formation of dye-nucleic acid complexes; and detecting the fluorescent signal of the dye-nucleic acid complexes.

The dye may be prepared for suitable use as described herein. Merely by way of example, the dye may be made into a stock solution using an aqueous solvent or a water-miscible and biologically compatible organic solvent at a concentration of greater than about 100 times that used in the final staining solution. Examples of suitable aqueous solvents that may be used alone or in combination with a suitable organic solvent in the making of a dye stock solution, include, but are not limited to, water, PBS buffer, and Tris buffer. Examples of suitable organic solvents for the making of a dye stock solution, include, but are not limited to, DMSO, DMF, methanol or ethanol. The stock solution is then diluted into a staining solution with a desired final dye concentration using a suitable aqueous solvent, such as water or a biological buffer, for example. In general, the specific dye concentration for the staining solution may be determined by the nature of the sample to be analyzed and the nature of the analysis being performed. By way of example, in general, a staining solution for use in conection with a cellular sample may have a dye concentration of about 1 nM or more, or up to about 10004. Further by way of example, in general, a staining solution for use in connection with an electrophoretic gel may have a dye concentration of about 1 μM or more, or up to about 50 μM.

A method of staining nucleic acids using a dye may be determined by the nature of the analysis being carried out. In the staining of nucleic acids in cellular or tissue samples, which may or may not be pre-fixed, the samples are usually incubated in a staining solution for a few minutes to 2 hours to allow the dye to permeate the cell membranes and combine with the nucleic acids. In some cases, nucleic acids may be present in the form of a solution comprising purified nucleic acids or crude cell extracts. In such cases, in general, addition of a dye stock solution to a nucleic acid solution should result in an instantaneously detectable fluorescence signal, the strength of which is proportional to the amount of nucleic acid. By way of example, a DNA titration curve is shown in FIG. 7. The substantially linear relationship between the amount of DNA and fluorescence intensity can be used for quantitation of DNA, or when cell extract is used, estimation of the number of cells. In certain instances, a nucleic acid may be embedded in an inert matrix, such as a blot or gel, a test strip, for example, or attached to a solid surface, such as a microarray chip or any other solid surface, for example. In such cases, in general, staining is carried out by applying a staining solution to the surface of the nucleic acid-comprising matrix, or to the surface of a microarray chip or other solid surface, and incubating for a period sufficient to allow formation of dye-nucleic acid complexes.

A fluorescent nucleic acid-dye complex may be detected either via its emission or excitation. By way of example, the fluorescent nucleic acid-dye complex may be, and typically is, excited by a light with wavelength at or near the absorption maximum wavelength of the complex. Further by way of example, the nucleic acid-dye complex may be excited by UV light with wavelength from 300 nm to 400 nm, which is a common source of excitation light available on most of the transluminators used for gel visualizing applications. By way of example, the fluorescent signal may be detected via various instruments, such as plate readers, microscopes, fluorometers, quantum counters, and flow cytometers, for example. Further by way of example, the fluorescent signal may be made by visual methods, such as visual inspection or photographic recording, for example.

Synthesis

The synthesis of a dye may be described in terms of synthesis of the monomeric dye constituents, synthesis of BRIDGE, and conjugation of the monomeric dye constituents to BRIDGE. Syntheses of monomeric dyes and monomeric dyes comprising a functional group or a reactive group are now described.

Synthesis of the Monomeric Dyes and Functional Molecules

Suitable monomeric dyes and monomeric dyes comprising a functional group or a reactive group may be prepared from scratch by a known procedure or any suitable procedure, or by modifying commercially available material that already has a suitable or desirable core structure. Many monomeric acridine dyes may be prepared from commercially available acridine dyes. A few examples of a commercially available acridine dye that may serve as suitable starting material for synthesis are set forth directly below.

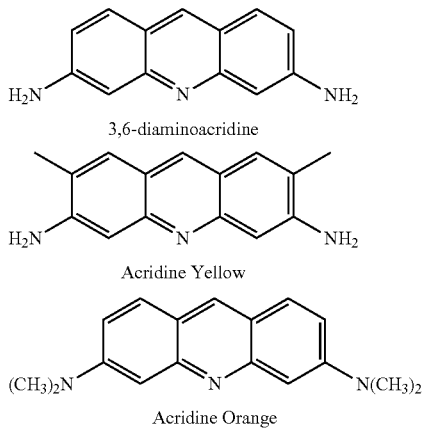

3,6-diaminoacridine

Acridine Yellow

Acridine Orange

Other acridine core structures may be prepared according to known procedures or any suitable procedures. Albert, A., *The acridines: their preparation, physical, chemical, and biological properties and uses*, Edward Arnold Ltd., London; Eldho, et al., *Synth. Commun.* 29, 4007 (1999); and Joseph, et al., *Bioconjugate Chem.* 15, 1230 (2004). An acridine core structure may be formed by condensing a suitable diphenylamine with a suitable carboxylic acid or a carboxylic acid equivalent in the presence of a Lewis acid, as schematically illustrated in Reaction 1 directly below.

Reaction 1

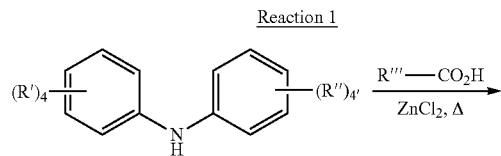

-continued

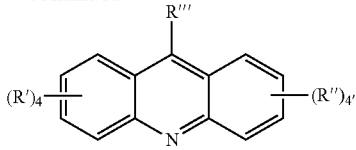

In Reaction 1, R', R" and R'" are suitable substituents, as further described below. The diphenylamine starting material is either commercially available or may be synthesized from a suitable arylhalide and a suitable arylamine using a known method or any suitable method. Yang, et al., *J. Organomet. Chem.* 576, 125 (1999); Hartwig, et al., *J. Org. Chem.* 64, 5575 (1999); and Wolfe, et al., *J. Org. Chem.* 65, 1158 (2000).

The nature of the substituents and the position where the substituents are attached may have a profound effect on the spectral property of the dye. In general, electron-donating groups at the 2-, 3-, 6- and 7-positions will increase the absorption and emission wavelengths of the dye. A typical electron-donating group may be an amino group, an alkylamino group, a dialkylamino group, a hydroxyl group, an alkoxy group, a thiol group, or an alkylthio group, by way of example. A more typical electron-donating group may be an amino group, an alkylamino group, a dialkylamino group, or an alkoxy group, by way of example. In general, an electron-withdrawing group at the 9-position will increase the absorption and emission wavelengths of the dye. A typical electron-withdrawing group may be a cyano group, a perfluoroalkyl group, an aminocarbonyl group, an alkylaminocarbonyl group, an alkylcarbonyl group, an aldehyde group, an alkoxycarbonyl group, an aminosulfonato group, an alkylaminosulfonato group, or a halide group, by way of example. A more typical electron-withdrawing group may be a cyano group, a perfluoroalkyl group, or a halide group.

In general, once the acridine core structure is built, the 10-nitrogen is alkylated with a haloalkyl group, which typically comprises an additional reactive group or a functional group that can be converted to a reactive group. The additional reactive group serves to conjugate the acridine dye to BRIDGE. Several ways of making monomeric acridine orange dyes with a suitable reactive group are schematically illustrated in Scheme 1 directly below.

Scheme 1
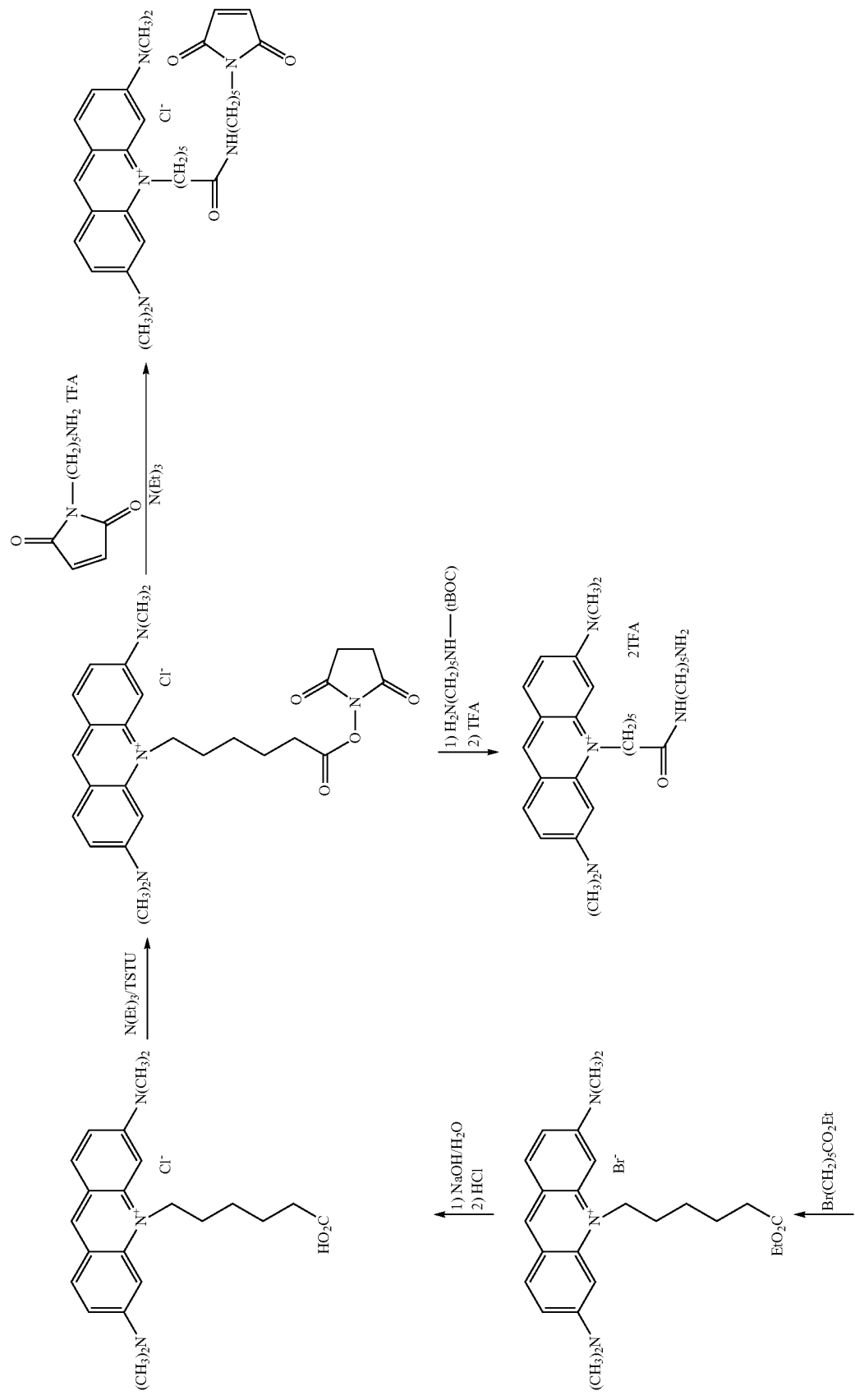

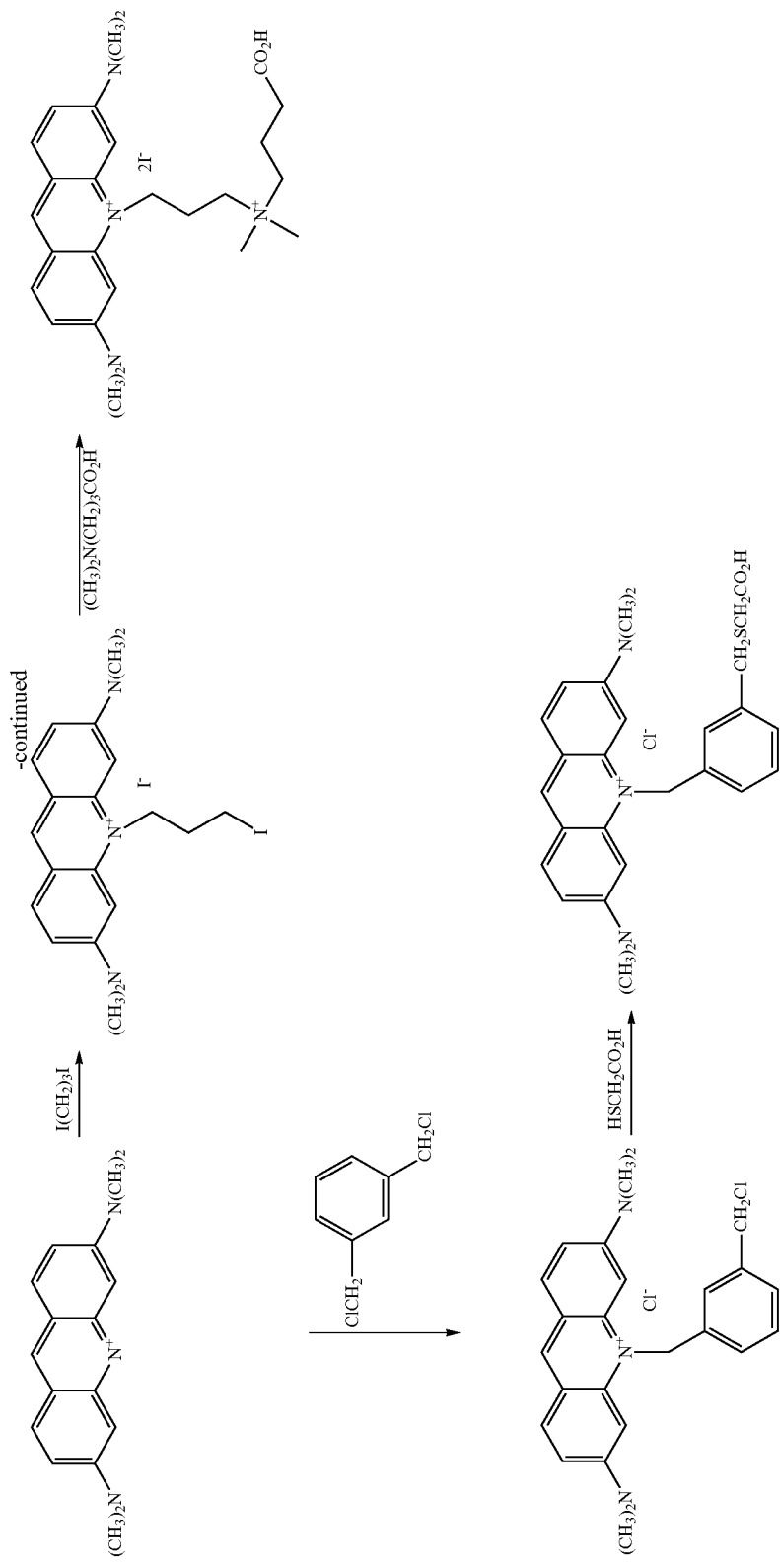

The 9-position of 10-alkylated acridine may be readily substituted with a cyano group, which can be further hydrolyzed to a carboxamide group, as schematically illustrated in Scheme 2 directly below.

dinium nitrogen. Such a substituent, especially a cyclic substituent, ortho to the quinolinium or pyridinium nitrogen, is said to confer desired properties to the asymmetric cyanine dyes, according to U.S. Pat. No. 5,436,134. These

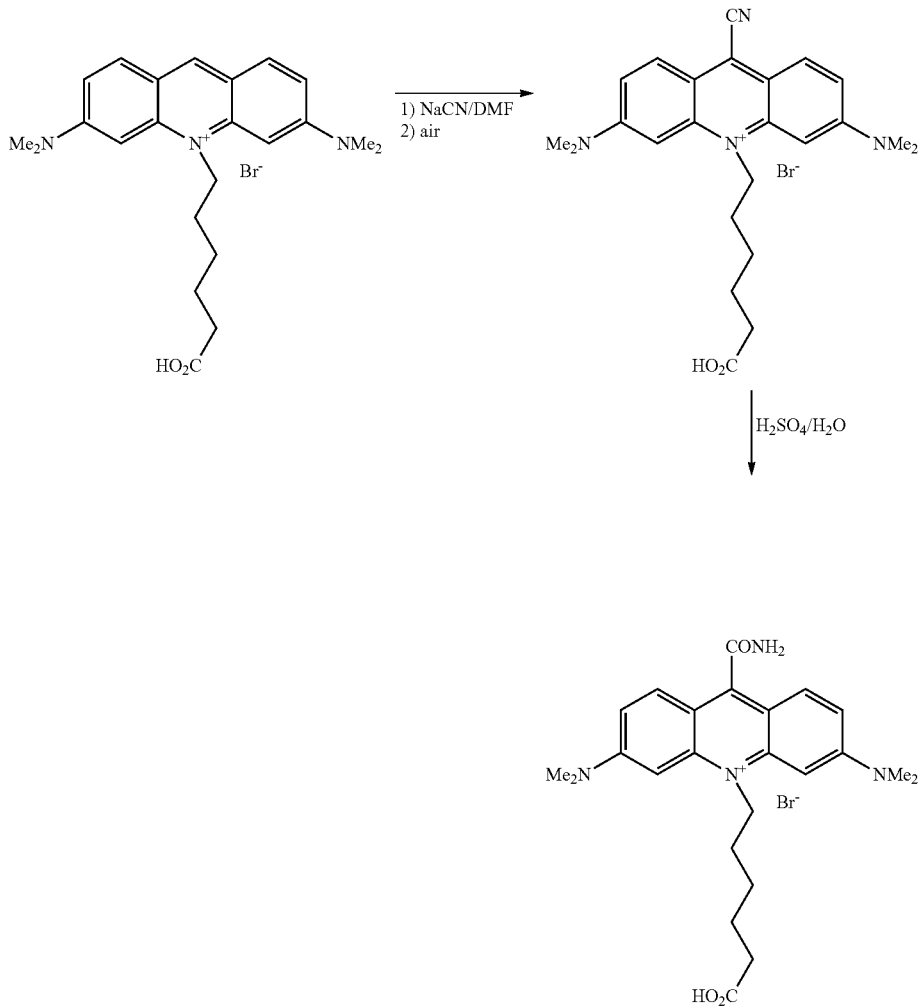

Scheme 2

Methods of preparing reactive monomeric asymmetric cyanine dyes have been described. Carreon, et al., *Org. Lett.* 6(4), 517 (2004). Such a dye may have the structure (Structure 11) set forth directly below.

Structure 11

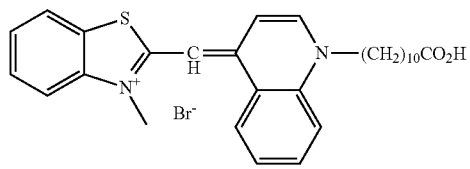

U.S. Pat. No. 5,863,753 discloses the preparation of a series of reactive asymmetric cyanine dyes, including ones that have a substituent ortho to the quinolinium or pyricyclically substituted asymmetric cyanine dyes are commonly referred to as SYBR dyes. Zipper, et al., *Nucleic Acids Res.* 32(12), e103 (2004). Some of the reactive SYBR dyes are commercially available from Molecular Probes, Inc. (Eugene, Oreg.), although the exact structures of these dyes are not known. Haugland, R. P., *Handbook of Fluorescent Probes and Research Chemicals*, 9th edition.

U.S. Patent Application Publication No. 2004/0132046 discloses methods for preparing monomeric asymmetric cyanine dyes with minor groove-binding capability. In general, these dyes possess a crescent-shaped structure by virtue of having an additional benzazolyl substituent on the benzazolyl ring of the dyes. Similar monomeric dyes having a suitable reactive group may be prepared using similar methods, for example, as schematically illustrated in Scheme 3 directly below.

Scheme 3
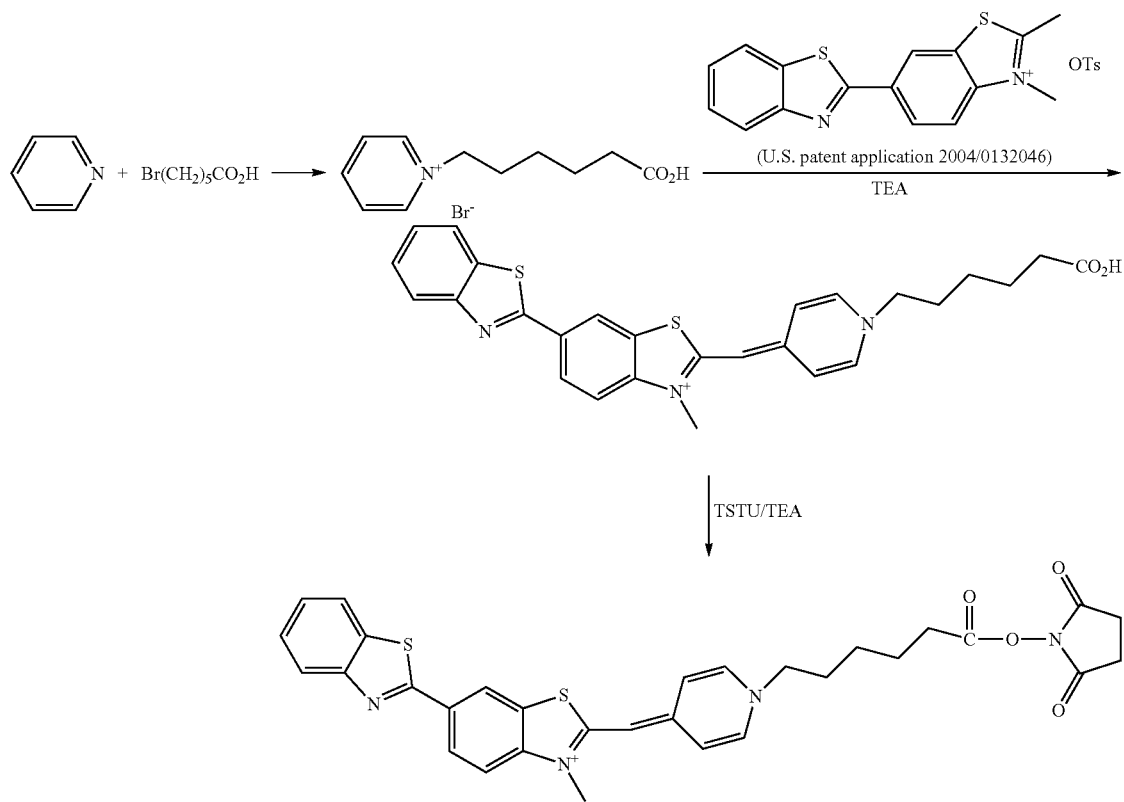
Reactive phenanthridinium dyes may be prepared from the commercially available 3,8-diamino-6-phenylphenanthridine, as schematically illustrated in Scheme 4 directly below.
Scheme 4
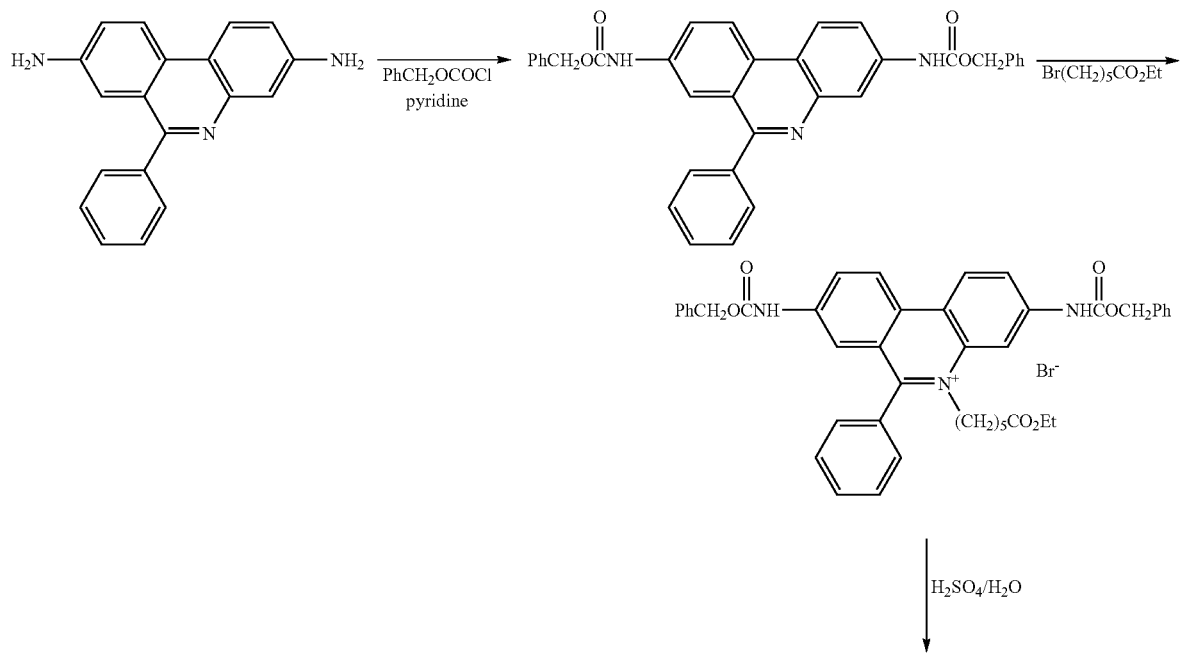

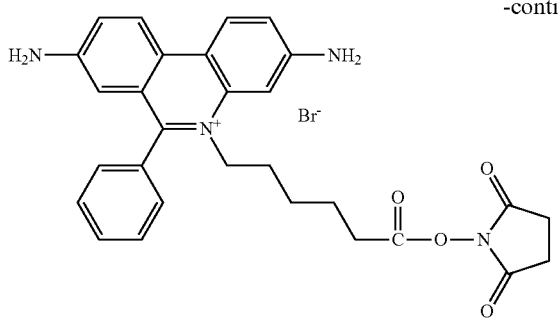
79

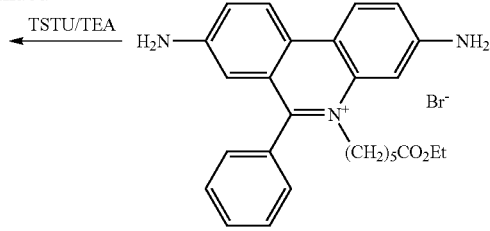
80

−continued
TSTU/TEA

Merely by way of example, Dye No. 35 of Table 2 may be prepared using the phenanthridinium intermediate with a reactive group shown in Scheme 4 above.

Preparations of pyronin derivatives with a reactive group at the 9-position may be carried out by condensing two equivalents of m-aminophenol derivative with one equivalent of dicarboxylic anhydride, as schematically illustrated in Scheme 5 directly below.

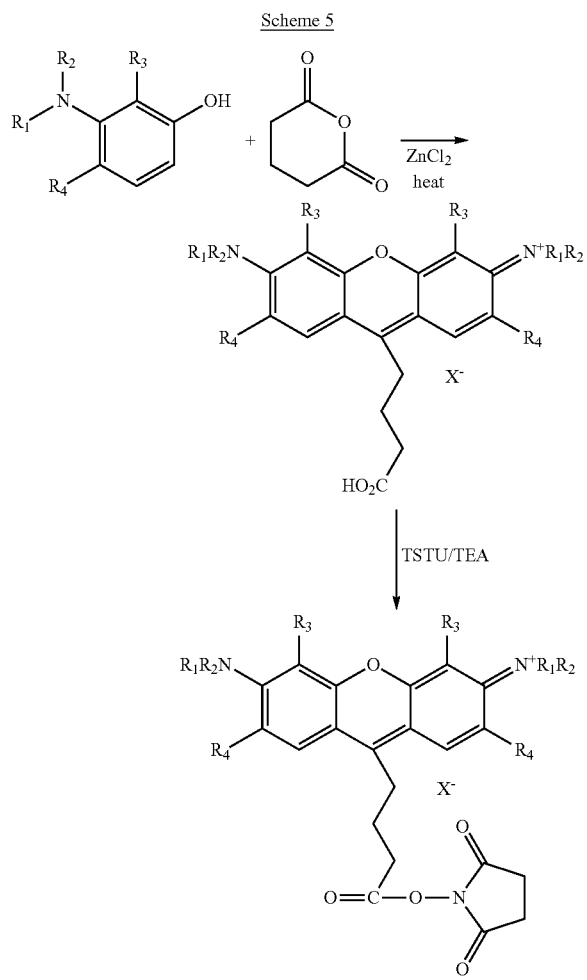

Scheme 5

Many monomeric non-fluorescent nucleic acid-binding dyes are known pigments used in textile and ink industries and are commercially available. References for preparations of these dyes can be found in the literature. Many suitable reactive monomeric fluorescent non-nucleic acid dyes and non-fluorescent non-nucleic acid dyes are commercially available or may be prepared readily using known methods.

Synthesis of BRIDGE

BRIDGE is usually formed when the monomeric dyes are coupled to a bi- or tri-functional group, which is often commercially available. In general, the terminal portions of BRIDGE are from the monomeric dyes themselves, while the middle portion of BRIDGE is from a bi- or tri-functional molecule available from a commercial source. In some cases, a significant portion of BRIDGE, such as up to about 90%, for example, may be pre-attached to the monomeric dyes prior to the final assembly of the dimeric or trimeric dye. In some other cases, most of BRIDGE may be prepared separately before the monomeric dyes are attached. In the case of heterodimer synthesis, a mono-protected bi-functional linker group is usually first attached to one monomeric dye, followed by de-protection and coupling to the second monomeric dye. Hetero trimeric dyes may be synthesized using a similar stepwise protection-de-protection strategy.

Conjugation of the Monomeric Dyes to BRIDGE

In general, dimeric and trimeric dyes may be assembled by conjugating monomeric dyes having a suitable reactive group with a bi- or tri-functional linker in a one-step coupling reaction for some of the homodimers, or in multi-step reactions for heterodimers and trimers or some of the homodimers comprising multiple bridge element A. Examples of synthetic routes to selected homodimer and heterodimers are schematically illustrated in Scheme 6 directly below.

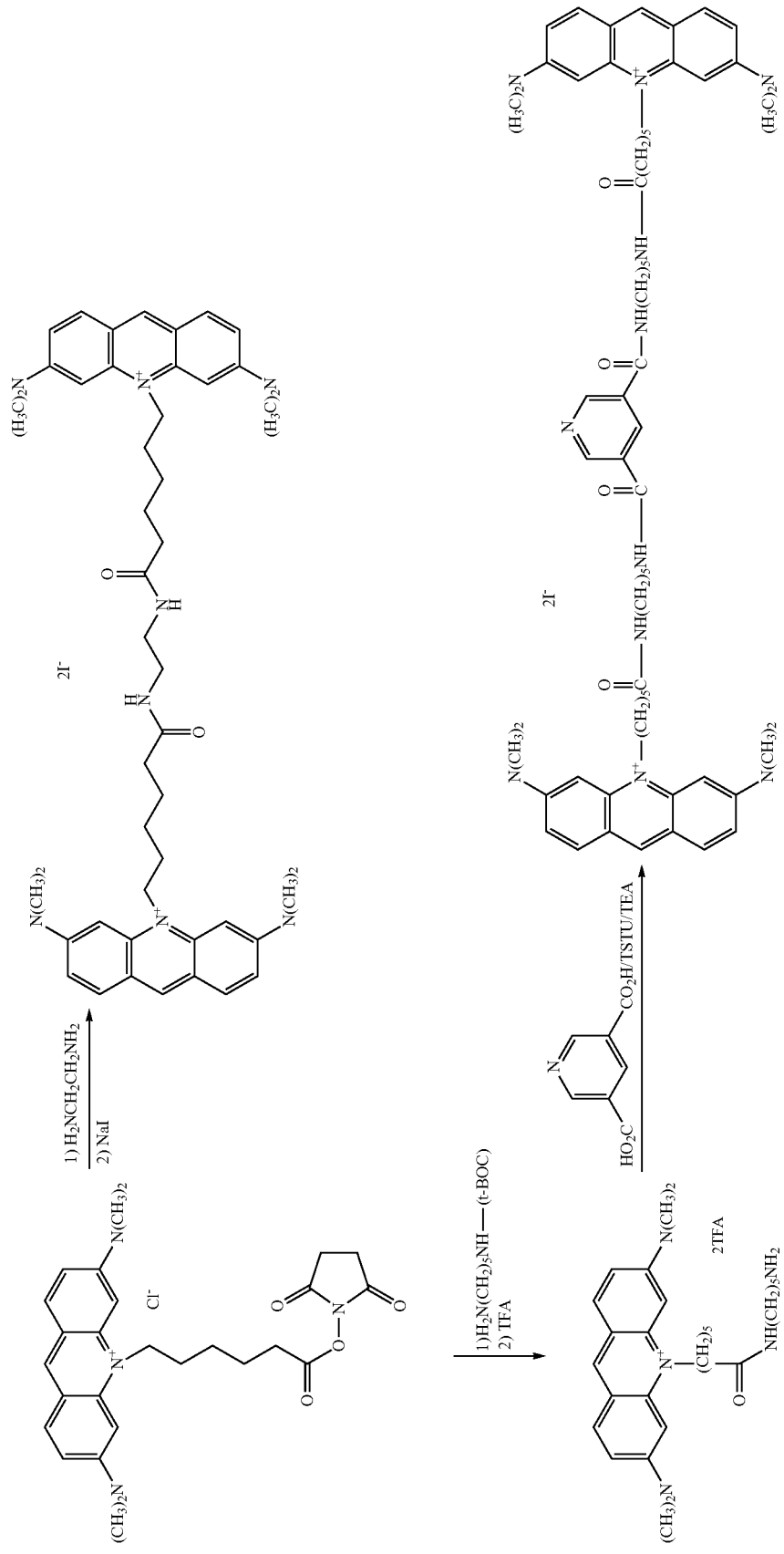

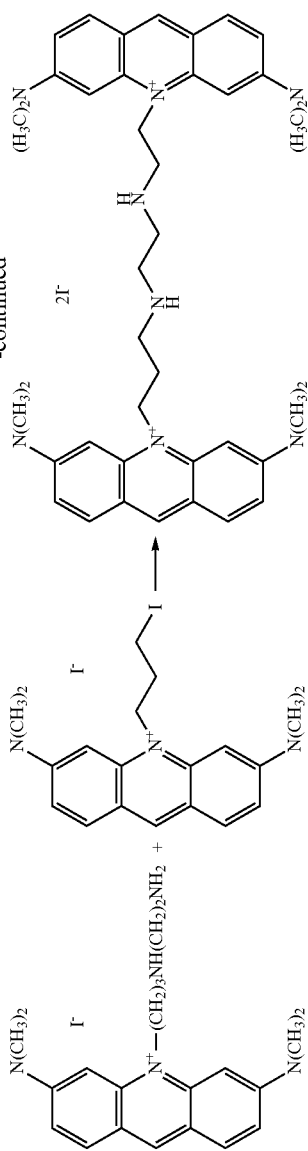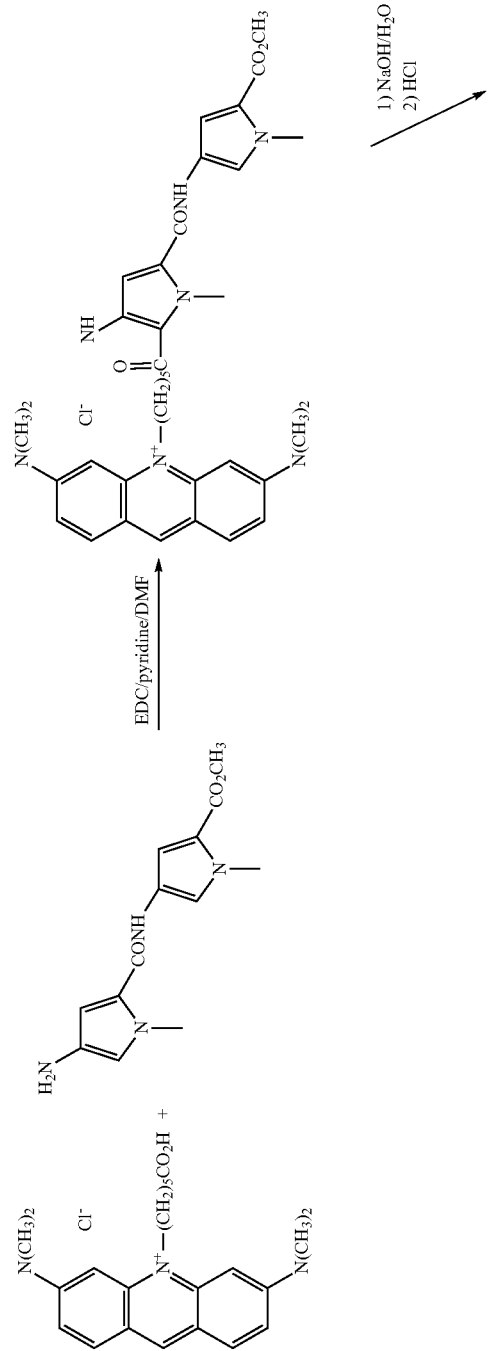

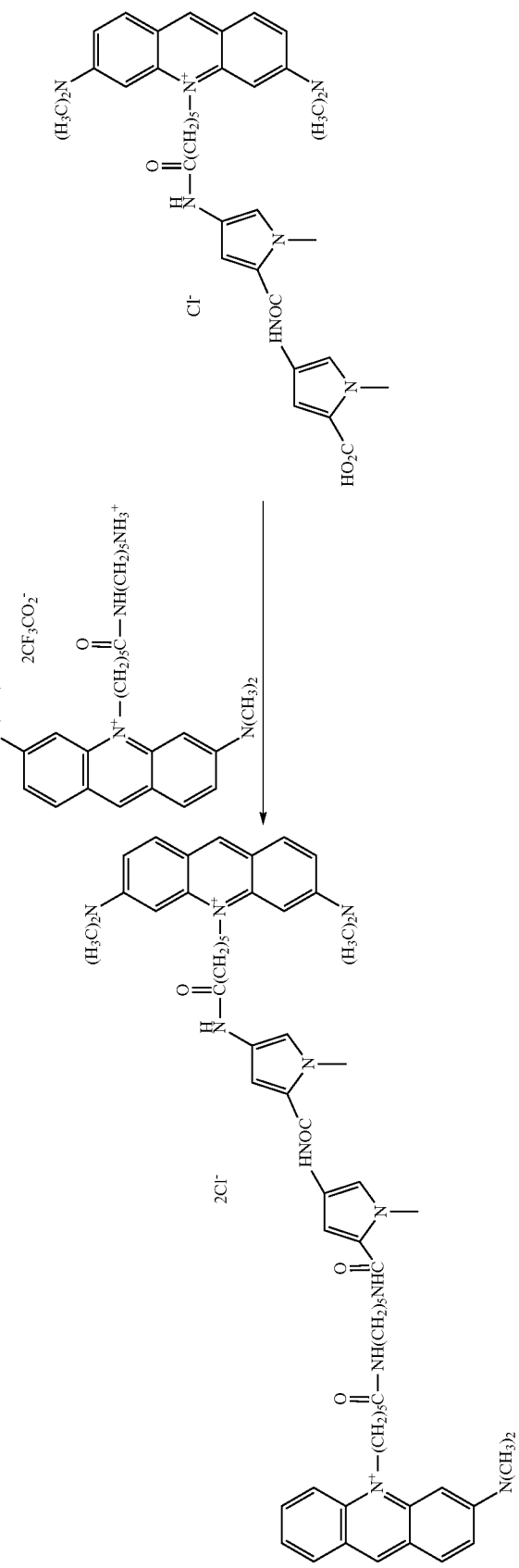
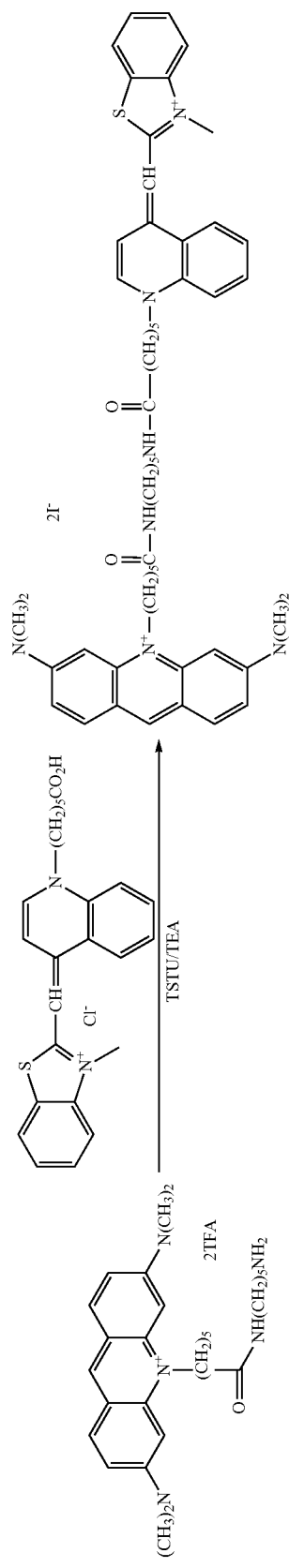

An example of the preparation of a homotrimeric dye is schematically illustrated in Scheme 7 directly below.
Scheme 7
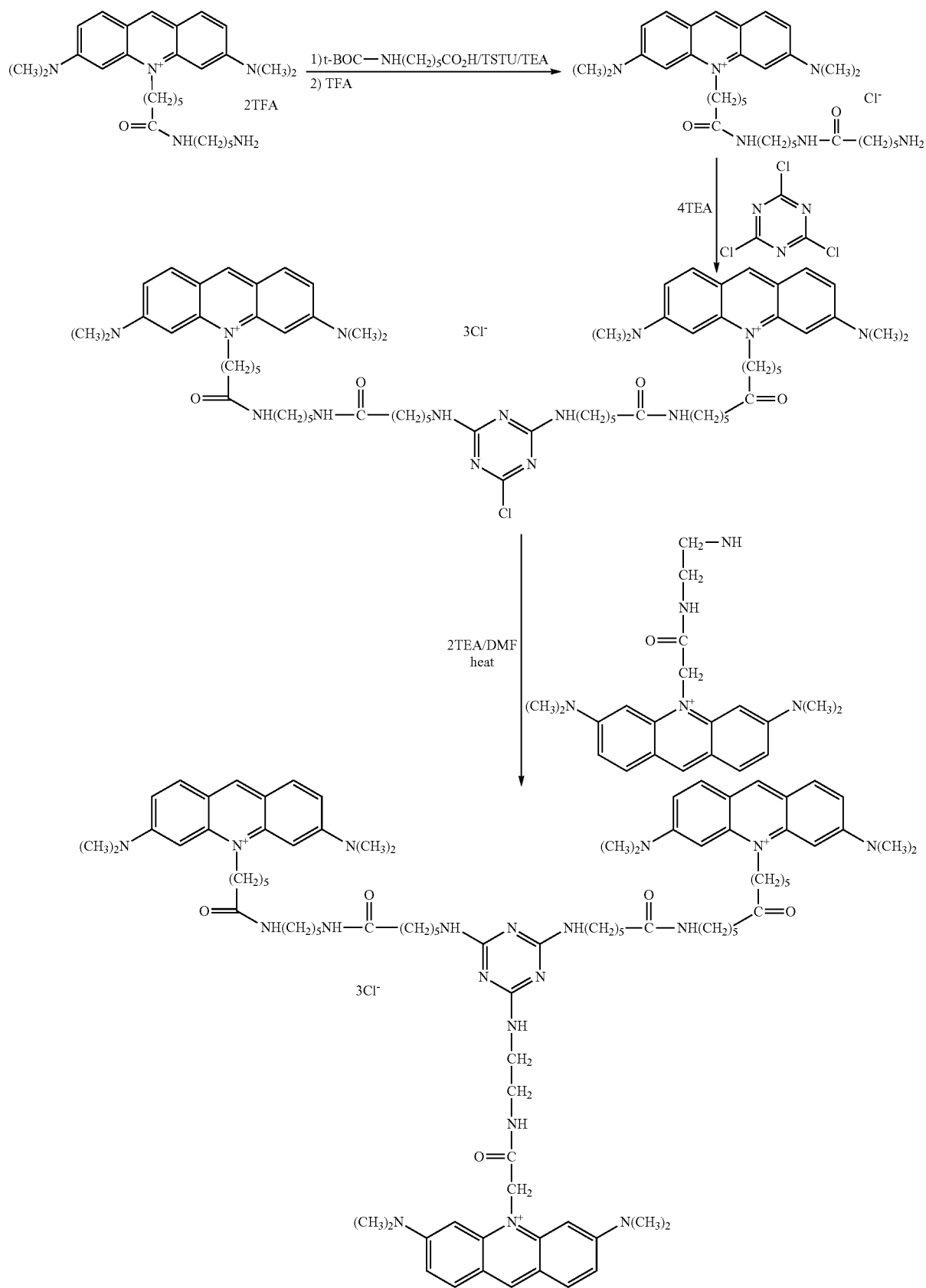

Examples of methods for preparing a dimeric dye having a reactive group are illustrated in Scheme 8 directly below.
Scheme 8
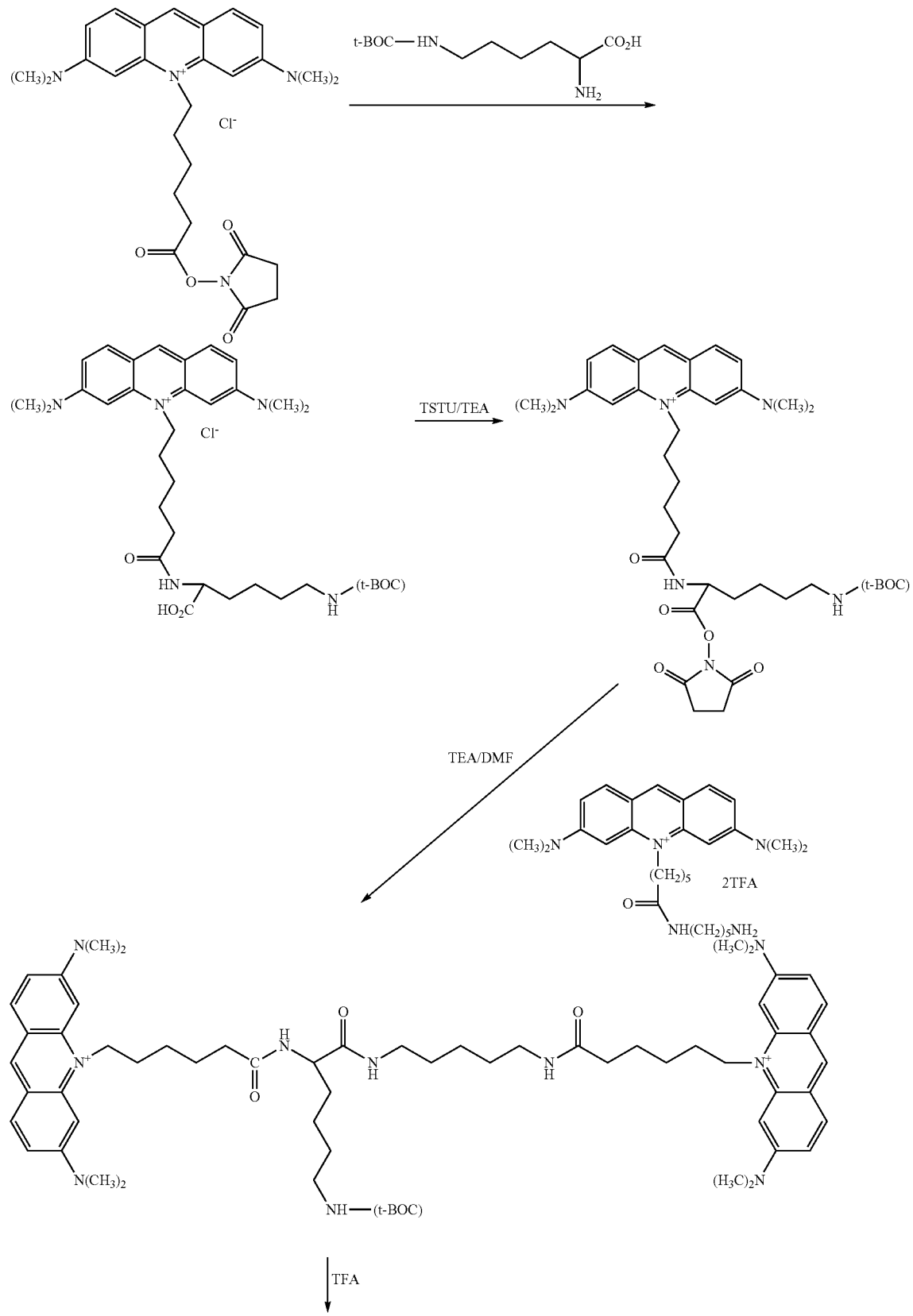

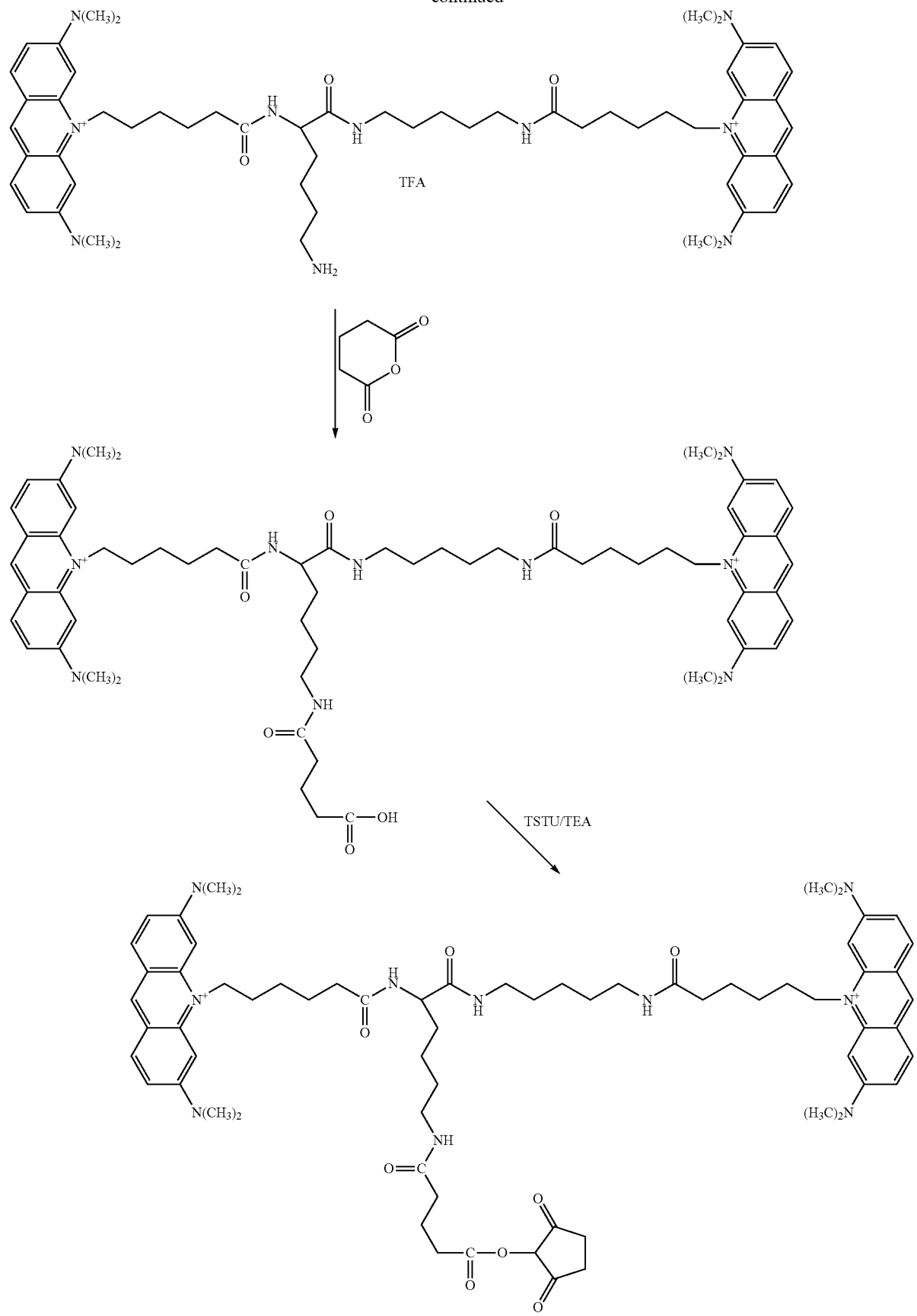

EXAMPLES

Example 1

Preparation of 10-(3-Iodopropyl)acridine orange, iodide

One equivalent of 1,3-diiodopropane was added to a suspension of 5 g of acridine orange (Aldrich) in 10 mL of chlorobenzene. The resulting mixture was stirred at 90-100° C. overnight. The hot reaction mixture was poured into ~200 mL of EtOAc. The orange precipitate was collected by filtration and dried under vacuum, yielding ~8 g.

Example 2

Preparation of 10-(5-Carboxypentyl)acridine orange, chloride salt 10-(5-Ethoxycarbonylpentyl)acridine bromide was prepared using the procedure of Example 1, with the exception that 1,3-diiodopropane was replaced with ethyl 6-bromohexanoic acid. The crude product (5 g) was suspended in ~100 mL methanol and 3 equivalents of NaOH dissolved in 30 mL $H_2O$. The suspension was stirred at room temperature for 24 h. Methanol was removed by evaporation, and the remaining aqueous solution was acidified with concentrated HCl. About 50 mL saturated NaCl was added to precipitate the product. The product was collected by filtration and then dried under vacuum at 45° C. for 24 hours.

Example 3

Preparation of DMAO (Dye No. 1 of Table 2)

10-(3-Iodopropyl)acridine orange, iodide (100 mg) was suspended in 20 mL 2M dimethylamine in methanol in a sealed tube and then stirred at 60° C. overnight. The mixture was cooled to room temperature and then poured into 50 mL EtOAc. The precipitate was collected by centrifugation and then dried under vacuum at 40° C. for 24 hours.

Example 4

Preparation of TMAO (Dye No. 2 of Table 2)

A mixture of DMAO (Dye No. 1 of Table 2) (11 mg, 0.023 mmol) and $CH_3I$ (0.5 mL) in $CH_3OH$ (2 mL) was refluxed gently for 4 days. The orange product (10 mg) was collected by suction filtration.

Example 5

Preparation of PMAO (Dye No. 5 of Table 2)

A mixture of 10-(3-iodopropyl)acridine orange iodide salt (100 mg, 0.18 mmol) and N,N,N'N'-tetramethyl-1,3-propanediamine (0.3 mL, 1.8 mmol) in $CH_3OH$ (10 mL) was refluxed overnight. After cooling down to room temperature, the precipitate was collected by suction filtration. The precipitate was resuspended in $CH_3OH$ (5 mL) and refluxed overnight and collected by suction filtration. It was dried to a constant weight in vacuo to give a dark red solid (14 mg).

Example 6

Preparation of AOAO-2Q (Dye No. 9 of Table 2)

A mixture of 10-(3-iodopropyl)acridine orange iodide salt (81 mg, 0.15 mmol) and PMAO (100 mg, 0.15 mmol) in DMF (1.5 mL) was heated at 130° C. for 7 hours. After cooling down to room temperature, $CH_3OH$ (15 mL) was added and the suspension was heated to reflux for 1 hour. Suction filtration gave the product as dark red solid (83.1 mg).

Example 7

Preparation of AOAO-2 (Dye No. 7 of Table 2)

$Et_3N$ (0.15 mL, 1.05 mmol) and TSTU (320 mg, 1.05 mmol) were added to a suspension of 10-(5-carboxypentyl)acridine orange chloride salt (438 mg, 1.03 mmol) in DMF (5 mL) at room temperature. The mixture was stirred at room temperature for 15 minutes, followed by the addition of $Et_3N$ (0.1 mL) and 3,3'-diamino-N-methyldipropylamine (50 mg, 0.344 mmol). After the mixture was stirred at room temperature overnight, EtOAc (20 mL) was added to precipitate the product. The crude product was re-dissolved in DMF and precipitated out again with EtOAc. The solid (250 mg) was separated by centrifugation.

Example 8

Preparation of AOAO-3 (Dye No. 8 of Table 2)

The dye (393 mg) was prepared by using the procedure to synthesize AOAO-2 from 10-(5-carboxypentyl)acridine orange (432 mg, 1.03 mmol) and ethylenediamine (25 mg, 0.42 mmol).

Example 9

Preparation of 10-(8-Bromooctyl)acridine orange bromide

A mixture of acridine orange (2 g, 7.53 mmol) and 1,8-dibromooctane (12 mL, 67.8 mmol) in chlorobenzene (15 mL) was heated at 110° C. overnight. EtOAc (50 mL) was added and the suspension was refluxed for 1 hour. After cooling down to room temperature, suction filtration gave the product as orange solid (3.56 g).

Example 10

Preparation of AOAO-5 (Dye No. 11 of Table 2)

A mixture of 10-(8-bromoactyl)acridine orange bromide (0.5 g, 0.94 mmol) and acridine orange (0.3 g, 11.2 mmol) in DMF (5 mL) was heated at 130° C. overnight. EtOAc was added to precipitate the product. Repeat precipitate from DMF and EtOAc gave the product as dark red solid (214 mg).

Example 11

Preparation of AOAO-7 (Dye No. 13 of Table 2)

The dye (30 mg) was synthesized by using the procedure to make AOAO-2 from 10-(5-carboxypentyl)acridine orange chloride salt (121 mg, 0.29 mmol) and 1,5-diaminopentane dihydrochloride (20 mg, 0.12 mmol).

Example 12

Preparation of AOAO-8 (Dye No. 15 of Table 2)

The dye (182 mg) was synthesized by using the procedure to make AOAO-2 from 10-(5-carboxypentyl)acridine orange chloride salt (241 mg, 0.58 mmol) and piperazine (20 mg, 0.23 mmol).

Example 13

Preparation of AOAO-11 (Dye No. 18 of Table 2)

The dye (112 mg) was synthesized by using the procedure to make AOAO-2 from 10-(5-carboxypentyl)acridine orange chloride salt (180 mg, 0.43 mmol) and 1,8-diaminooctane (25 mg, 0.17 mmol).

Example 14

Preparation of AOAO-12 (Dye No. 19 of Table 2)

The dye (76 mg) was synthesized by using the procedure to make AOAO-2 from 10-(5-carboxypentyl)acridine orange chloride salt (147 mg, 0.35 mmol) and 2,2'oxybis(ethyl-amine) dihydrochloride (25 mg, 0.14 mmol).

Example 15

Preparation of AOAO-13 (Dye No. 20 of Table 2)

The dye (64 mg) was synthesized by using the procedure to make AOAO-2 from 10-(5-carboxypentyl)acridine orange chloride salt (96 mg, 0.23 mmol) and 4,7,10-trioxa-1,13-tridecanediamine (20 mg, 0.09 mmol).

Example 16

Preparation of 1,3-Di-((2-(N-t-Boc-amino)ethyl)aminocarbonyl)benzene (Dye No. 101, Shown Directly Below)

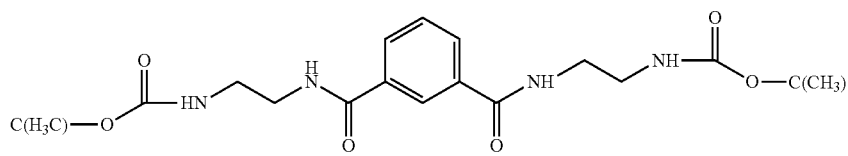

Et₃N (0.4 mL, 2.71 mmol) and TSTU (820 mg, 2.71 mmol) were added to a solution of isophthalic acid (220 mg, 1.32 mmol) in DMF (2 mL) at room temperature. The mixture was stirred at room temperature for 30 minutes. Addition of Et₃N (1 mL) and mono-tBoc-ethylenediamine (460 mg, 2.86 mmol) followed. The mixture was stirred at room temperature overnight and then partitioned between 1N HCl (100 mL) and EtOAc (50 mL). The aqueous layer was extracted with EtOAc (50 mL) and the combined organic layers were washed with 1N HCl (2×50 mL), H₂O (50 mL), and saturated NaCl (50 mL), and dried with anhydrous Na₂SO₄. The crude product was purified by column chromatography using EtOAc:hexanes (9:1) as eluent to give the colorless solid product (356 mg).

Example 17

Preparation of
1,3-Di-((2-aminoethyl)aminocarbonyl)benzene,
trifluoro-acetic acid salt (Dye No. 102, Shown
Directly Below)

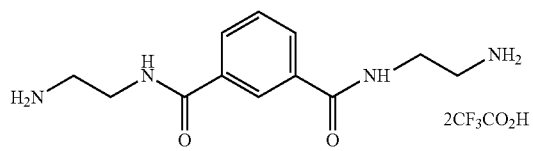 [SMILES: NCCNC(=O)c1cccc(C(=O)NCCN)c1]

1,3-di-((2-(N-t-Boc-amino)ethyl)aminocarbonyl)benzene (356 mg, 0.79 mmol) was added to TFA (5 mL) at 0° C. The mixture was stirred at 0° C. for 1 hour and the solution was concentrated to dryness in vacuo. The colorless residue was dissolved in CH₃OH (2 mL) and added dropwise to Et₂O (30 mL). The precipitate was collected by centrifugation and dried to a constant weight in vacuo to give the solid product (425 mg).

Example 18

Preparation of AOAO-9 (Dye No. 16 of Table 2)

The dye (55 mg) was prepared by using the procedure to make AOAO-2 from 10-(5-carboxypentyl)acridine orange chloride salt (109 mg, 0.26 mmol) and 1,3-Di((2-aminoethyl)aminocarbonyl)benzene, trifluoroacetic acid salt (50 mg, 0.1 mmol).

Example 19

Preparation of 1,3-Di((5-(N-t-Boc-amino)pentyl)
aminocarbonyl)benzene (Dye No. 103, Shown
Directly Below)

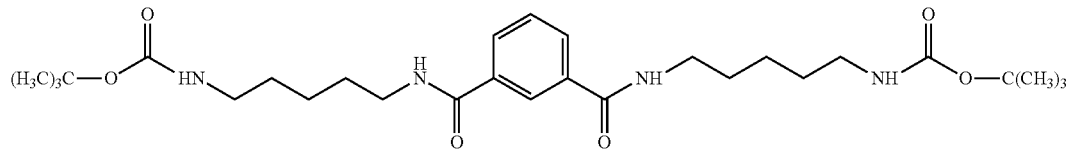 [SMILES: CC(C)(C)OC(=O)NCCCCCNC(=O)c1cccc(C(=O)NCCCCCNC(=O)OC(C)(C)C)c1]

The dye (555 mg) was prepared according to the procedure to make 1,3-di-((2-(N-t-Boc-amino)ethyl)aminocarbonyl)benzene from isophthalic acid (254 mg, 1.53 mmol) and mono-tBoc cadaverine (640 mg, 3.15 mmol).

Example 20

Preparation of
1,3-Di-((5-aminopentyl)aminocarbonyl)benzene,
trifluoro-acetic acid salt (Dye No. 104, Shown
Directly Below)

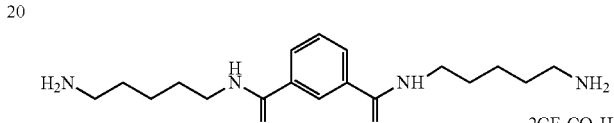

The dye (560 mg) was prepared according to the procedure for Dye No. 102 (555 mg, 1.04 mmol).

Example 21

Preparation of AOAO-10 (Dye No. 17 of Table 2)

The dye (22 mg) was prepared by using the procedure to make AOAO-2 from 10-(5-carboxypentyl)acridine orange chloride (95 mg, 0.23 mmol) and Dye No. 104 (50 mg, 0.09 mmol).

Example 22

Preparation of AOAO-14 (Dye No. 21 of Table 2)

The dye (150 mg) was prepared by using the procedure to make AOAO-2 from 10-(5-carboxypentyl)acridine orange chloride (166 mg, 0.40 mmol) and diamido-dPEG-diamine (Quanta Biodesign of Powell, Ohio) (100 mg, 0.15 mmol).

Example 23

Preparation of 10-((((3-(N-Boc-amino)propyl)-N,N-dimethyl)ammonium)propyl) acridine, diiodide (Dye No. 105, Shown Directly Below)

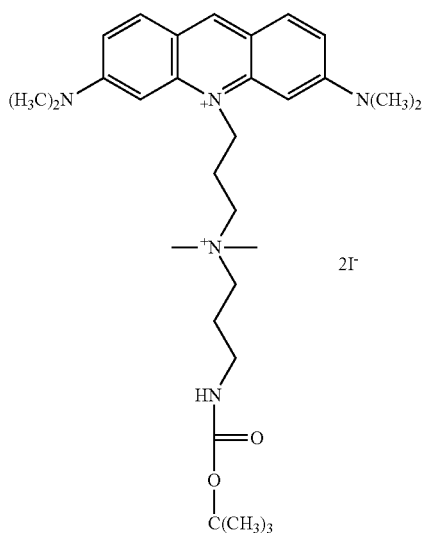

A mixture of 10-(3-iodopropyl)acridine orange iodide (500 mg, 0.89 mmol) and 3-(N-t-Boc-amino)propyl-N,N-dimethylamine (1.8 g, 8.9 mmol) in CH$_3$OH (50 mL) was refluxed overnight. After cooling down to room temperature, the precipitate was collected by suction filtration and dried to a constant weight to give Dye No. 105 as an orange solid (292 mg).

Example 24

Preparation of 10-((((3-ammonium)propyl)-N,N-dimethyl)ammonium)propyl acridine, trifluoroacetate salt (Dye No. 106, Shown Directly Below)

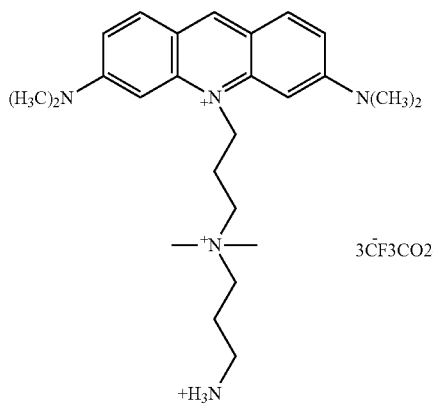

Dye No. 105 (50 mg, 0.06 mmol) was added to TFA (2 mL) at 0° C. The mixture was stirred at 0° C. for 30 minutes. The solution was concentrated to dryness in vacuo and the residue was dissolved in CH$_3$OH (3 mL). The solution was added dropwise to Et$_2$O (30 mL) and the precipitate was collected by centrifugation and dried to a constant weight in vacuo to give Dye No. 106 as an orange solid (28 mg).

Example 25

Preparation of AOAO-4 (Dye No. 10 of Table 2)

The dye (23 mg) was prepared by using the procedure to make AOAO-2 from 10-(5-carboxypentyl)acridine orange chloride salt (31 mg, 0.075 mmol) and Dye No. 106 (28 mg, 0.036 mmol).

Example 26

Preparation of 10-(6-(N-Phthalimido)hexyl)acridine orange bromide salt (Dye No. 107, Shown Directly Below)

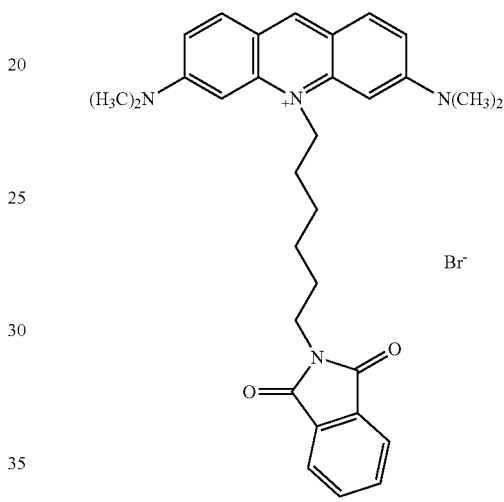

A mixture of acridine orange (2 g, 7.54 mmol) and N-(6-bromohexyl)phthalimide (4.7 g, 15.1 mmol) in chlorobenzene (20 mL) was heated at 110° C. for 2 days. EtOAc (50 mL) was added and the suspension was heated to reflux for 1 hour. After cooling down to room temperature, the product Dye No. 107 was collected by suction filtration as an orange solid (3.76 g).

Example 27

Preparation of 10-(5-((5-Carboxypentyl)aminocarbonyl)pentyl)acri-dine orange, iodide (Dye No. 108, Shown Directly Below)

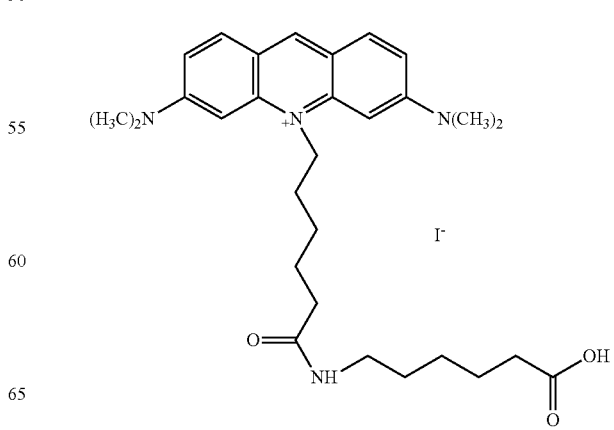

Et₃N (40 µL, 0.28 mmol) and TSTU (81 mg, 0.27 mmol) were added to a suspension of 10-(5-carboxypentyl)acridine orange chloride (107 mg, 0.258 mmol) in DMF (3 mL). The mixture was stirred at room temperature for 15 minutes. Addition of Et₃N (0.2 mL) and a solution of 6-aminohexanoic acid (67 mg, 0.51 mmol) in H₂O (1 mL) followed. The mixture was stirred at room temperature for 1 hour and concentrated to dryness in vacuo. The residue was triturated with H₂O to give Dye No. 108 as an orange solid (125 mg).

Example 28

Preparation of
9-Cyano-10-(5-carboxypentyl)acridine orange, chloride (Dye No. 109, Shown Directly Below)

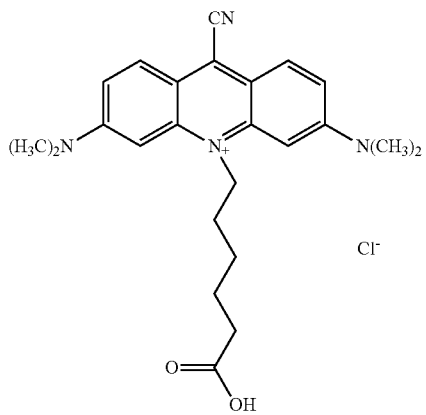

A mixture of 10-(5-carboxypentyl)acridine orange (0.15 g, 0.361 mmol) and sodium cyanide (35 mg, 0.722 mmol) in DMF (3 mL) was stirred at room temperature in open air for 2 days. CH₃CN (10 mL) was added and the resulting suspension was stirred at room temperature for 1 hour. The dark blue precipitate was collected by centrifugation and dried to a constant weight in vacuo to give Dye No. 109 (130 mg).

Example 29

Preparation of AOAO-12R (Dye No. 22 of Table 2)

Et₃N (32 µL, 0.23 mmol) and TSTU (68 mg, 0.227 mmol) were added to a solution of Dye No. 109 (98.3 mg, 0.223 mmol) in DMF (2 mL) at room temperature. The mixture was stirred at room temperature for 15 minutes. Addition of Et₃N (100 µL) and 2,2'-oxybis-(ethylamine) dihydrochloride (16 mg, 0.09 mmol) followed. The mixture was stirred at room temperature for 2 days. The solution was concentrated to about 1 mL and EtOAc (2 mL) was added. The precipitate was collected by centrifugation. The product was re-dissolved in DMF and precipitated again with EtOAc to give Dye No. 22 as a dark blue solid (54.4 mg).

Example 30

Preparation of
9-Aminocarbonyl-10-(5-carboxyphentyl)acridine
(Dye No. 110, Shown Directly Below)

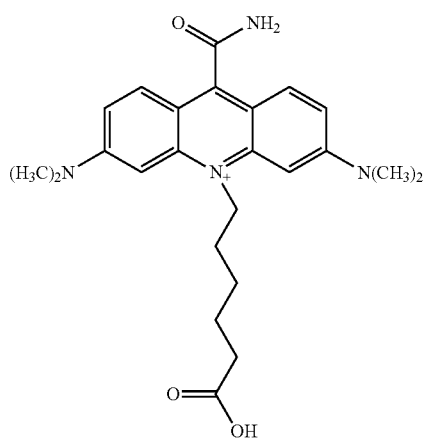

A solution of Dye No. 109 (30 mg, 0.068 mmol) in 75% H₂SO₄ (1 mL) was heated at 60° C. for 2 days. After cooling down to room temperature, the mixture was added to Et₂O (10 mL). The precipitate was collected by centrifugation and re-dissolved in CH₃OH (1.5 mL). EtOAc (10 mL) was added and the solid precipitate was collected by centrifugation and dried to a constant weight in vacuo to give Dye No. 110 as a dark pink solid (20.4 mg).

Example 31

Preparation of N-Carboxypentyl thiazole orange
(Shown Directly Below)

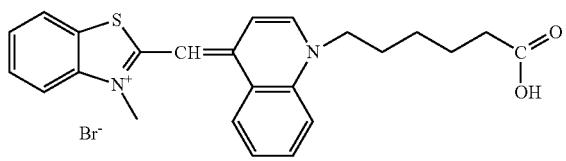 [SMILES: C[n+]1c(C=C2C=CN(CCCCCC(=O)O)c3ccccc32)sc2ccccc21 ; [Br-]]

The dye was prepared using published procedure (Carreon, et al., *Org. Let.* 6(4), 517 (2004)).

Example 32

Preparation of TOTO-3 (Dye No. 14 of Table 2)

The dye (354 mg) was prepared using the procedure to synthesize AOAO-2 from N-Carboxypentyl thiazole orange (460 mg, 1.04 mmol) and ethylene diamine (25 mg, 0.42 mmol).

Example 33

Preparation of 10-(5-((2-(N-t-Boc-amino)ethyl)aminocarbonyl)pentyl)acridine orange chloride salt (Dye No. 111, Shown Directly Below)

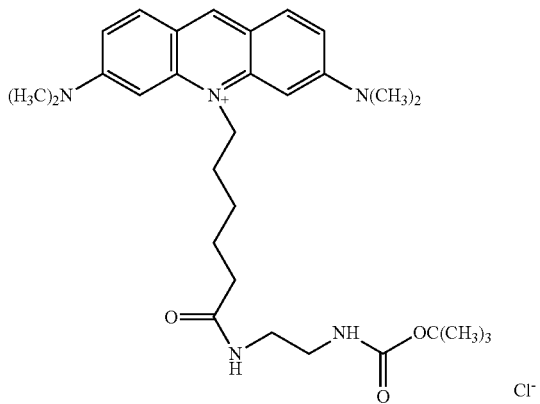

$Et_3N$ (106 µL, 0.76 mmol) and TSTU (230 mg, 0.76 mmol) were added to a suspension of 10-(5-carboxypentyl)acridine orange chloride (302 mg, 0.73 mmol) in DMF (3 mL). The mixture was stirred at room temperature for 15 minutes. The addition of $Et_3N$ (350 µL) and mono t-BOC-ethylenediamine (150 mg, 0.92 mmol) followed. The mixture was stirred at room temperature for 1 hour and then concentrated to dryness in vacuo. The residue was dissolved in $CH_3CN$ (2 mL) and precipitated by the addition of EtOAc (20 mL). The precipitate was collected by centrifugation and dried to a constant weight to give Dye No. 111 as orange solid (365 mg).

Example 34

Preparation of 10-(5-((2-Ammoniumethyl)aminocarbonyl)pentyl)acridine orange, trifluoroacetate (Dye No. 112, Shown Directly Below)

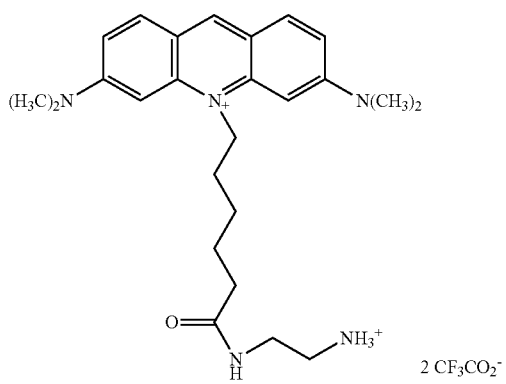

Dye No. 111 (347 mg, 622 mmol) was added in one portion to trifluoroacetic acid (3 mL) at 5° C. The mixture was stirred at 5° C. for 1 hour and concentrated to dryness in vacuo. The residue was dissolved in $CH_3OH$ (3 mL) and added dropwise to $Et_2O$ (50 mL). The precipitate was collected by centrifugation to give Dye No. 112 as orange solid (297 mg).

Example 35

Preparation of AOTO-3 (Dye No. 23 of Table 2)

$Et_3N$ (20 µL, 0.142 mmol) and TSTU (42.2 mg, 0.142 mmol) were added to a solution of N-carboxypentylthiazole orange (62 mg, 0.142 mmol) in DMF (1 mL). The mixture was stirred at room temperature for 15 minutes. Addition of $Et_3N$ (70 µL) and Dye No. 112 (50 mg, 0.095 mmol) followed. The mixture was stirred at room temperature for 2 hours and then concentrated to dryness in vacuo. The residue was re-dissolved in DMF (1 mL) and EtOAc (2 mL) was added. The precipitate was collected by centrifugation. Repeated precipitation from DMF and EtOAc gave the product as orange red solid (50.4 mg)

Example 36

Preparation of TOTO-12 (Dye No. 24 of Table 2)

The dye (19.4 mg) was prepared by using the procedure to synthesize AOAO-2 from N-carboxypentylthiazole orange (94.5 mg, 0.2145 mmol) and 2,2'oxybis(ethylamine) dihydrochloride (15 mg, 0.085 mmol).

Example 37

Preparation of TO(3)TO(3)-12 (Dye No. 25 of Table 2)

The dye (32.6 mg) was prepared by using the procedure to synthesize AOAO-2 from N-carboxypentyl thazole blue (Carreon, et al., *Org. Let.* 6(4), 517 (2004); and Benson, et al., *Nucleic Acid Res.* 21(24), 5727 (1993)) (99 mg, 0.212 mmol) and 2,2'oxybis(ethylamine) dihydrochloride (15 mg, 0.085 mmol).

Example 38

Preparation of TO(3)TO(3)-2 (Dye No. 26 of Table 2)

The dye (28.4 mg) was prepared by using the procedure to synthesize AOAO-2 from N-carboxypentyl thiazole blue (76 mg, 0.173 mmol) and 3,3'-diamino-N-methyldi-propylamine (10 mg, 0.069 mmol).

Example 39

Preparation of 10-(5-((5-(N-t-Boc-amino)pentyl)aminocarbonyl)pentyl)-acridine orange, chloride (Dye No. 113, Shown Directly Below)

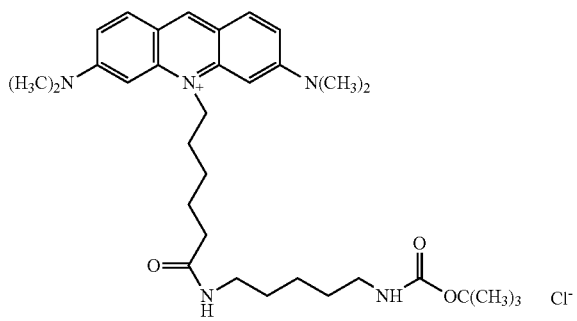

The dye (280 mg) was prepared by using the procedure to synthesize Dye No. 111 from 10-(5-carboxypentyl)acridine orange chloride (200 mg, 0.483 mmol) and mono t-BOC-cadaverine (130 mg, 0.628 mmol).

Example 40

Preparation of 10-(5-((5-ammoniumpentyl)aminocarbonyl)pentyl)acridine orange, trifluoroacetate (Dye No. 114, Shown Directly Below)

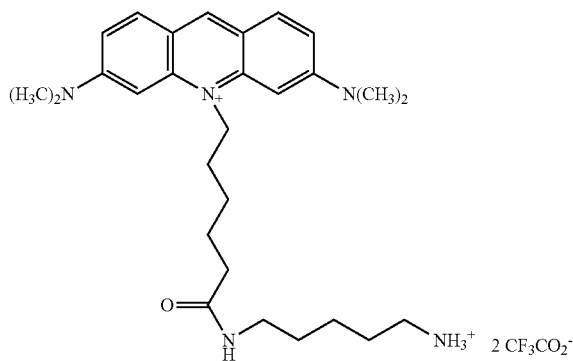

Dye No. 114 (234 mg) was prepared by using the procedure to synthesize Dye No. 112 from Dye No. 113 (280 mg, 0.467 mmol).

Example 41

Preparation of AORO-7 (Dye No. 27 of Table 2)

The compound (29 mg) was prepared by using the procedure to synthesize AOTO-3 from compound No. 114 (35 mg, 0.061 mmol) and the rosamine dye (Biotium, Inc. (Hayward, Calif.)) (40 mg, 0.063 mmol).

Example 42

Absorbance and Fluorescence of DMAO and AOAO-7

The absorbance spectra, as shown in FIG. 2 and FIG. 3, and fluorescence emission spectra, as shown in FIG. 4, of DMAO and AOAO-7, were measured separately without DNA presence, or with DNA presence (2 mg/ml of salmon sperm DNA), in PBS buffer. All dye concentrations were adjusted to provide an optical density of 0.05 at 495 nm. The spectra were normalized to 1 in the absorbance plot. Relative to DMAO, AOAO-7 exhibits a new shorter wavelength peak at 471 nm in absorbance, indicating aggregation of the two acridine monomers within AOAO-7. Upon binding to DNA, absorbances of AOAO-7 and DMAO showed 5 nm- and 10 nm-red shifts, respectively, relative to free dyes. The fluorescence of free AOAO-7 is about 5 times lower than that of DMAO. The lower background fluorescence of AOAO-7 is advantageous in real time qPCR. The fluorescence per acridine monomer of AOAO-7 is close to that of DMAO, indicating that two monomers of AOAO-7 no longer quenched each other when bound to DNA and the linker between the two did not exhibit negative effect on the quantum yield.

Example 43

Absorbance Spectra of TOTO-1 and TOTO3

In a similar manner to that described in connection with Example 42, the absorbance spectra of TOTO-1 and TOTO-3 were measured without DNA presence, as shown in FIG. 5, or in the presence of 2 mg/ml of salmon sperm DNA, as shown in FIG. 6, in PBS buffer. As shown in FIG. 5, the spectra of the free dyes indicate that TOTO-3, which has BRIDGE that is neutral or substantially devoid of positive charges, forms an intramolecular H-dimer, or a hairpin structure, while TOTO-1, which has multiple positive charges, has less spectral shift. As shown in FIG. 6, the absorption spectra of both TOTO-1 and TOTO-3 in the presence of DNA shift to about the same position, indicating that the hairpin structure of TOTO-3 dimer opens up upon binding to DNA, and that both TOTO-1 and TOTO-3 form similar types of DNA-dye complexes.

Example 44

Fluorescence of AOAO-12 in Response to Different Amount of DNA

The fluorescence of 0.1 μM AOAO-12 in 200 mL of PBS in the presence of 0, 0.1, 0.2, 0.4, 0.6, 0.8, 1.0, 2.0, 4.0, 6.0, 8.0 and 10 μg/ml final concentrations of salmon sperm DNA or a mixture of single-stranded 20mer oligonucleotide were measured on a microtiter plate reader (SpectraMax of Molecular Devices Corporation (Sunnyvale, Calif.)). The fluorescence was plotted against DNA concentration, as shown in FIG. 7. It can be seen that fluorescence linearly responded to DNA up to 2.0 μg/ml (inset). At higher concentrations of DNA, the response became non-linear. AOAO-12 fluoresces more intensely when bound to double stranded DNA than when bound to single stranded DNA.

Example 45

Comparing Signal Strengths of AOAO-12 and SYBR Green I in qPCR

This example demonstrates the superior property of AOAO-12 to SYBR Green I in fluorescence signal strength in qPCR. All real-time amplifications were performed in 204 reaction solution comprising 10 mM Tris (pH 8.0), 50 mM KCl, 3.5 mM $MgCl_2$, 2 mM each of dNTP, and 1 unit of AmpliTaq DNA polymerase (ABI, Foster City, Calif.) and various concentrations of a fluorescent monitoring dye. An ATPB fragment (SEQ ID NO: 1) in pTOPO plasmid was amplified with 0.5 µM forward primer 5'-GAGGTCT-TCACAGGTCATA-3' (SEQ ID NO: 2), 0.5 µM reverse primer 5'-CTCTTCAGCCAGCTTATC-3' (SEQ ID NO: 3). The thermal regimen was set at 95° C. for 1 minute followed by 50 cycles of 15-second duration at 95° C., of 15-second duration at 55° C., and of 15-second duration at 72° C. Fluorescence was measured at the 55° C. stage. Consistent with an earlier report (Nath, K., et al., Effects of ethidium bromide and SYBR Green I on different polymerase chain reaction systems, *J. Biochem Biophys Methods* 42, 15 (2000)), SYBR Green I exhibited inhibition to PCR reactions, as shown in FIG. 8, where Ct was delayed at higher SYBR Green I concentrations. Relative to SYBR Green I concentrations, higher concentrations of AOAO-12 could be added to reactions without exhibiting inhibition. As a result, the final fluorescence strength with AOAO-12 could be several folds higher, allowing for more sensitive detection. Alternatively, with AOAO-12, a less sensitive optical device could be used in thermal cycling fluorometers, leading to less expensive instruments.

Example 46

Titration of Human Genomic DNA

Amplifications of a UBC fragment (SEQ ID NO: 8) from human genomic DNA were performed under conditions similar to those set forth in Example 45, with either SYBR Green I (final absorption peak at 495 nm corresponds to an optical density of 0.025, or $A_{495}=0.025$) or AOAO-12 (final $A_{495}=0.1$), except that (1) different forward and reverse primers sets (5'-ACTGGTAAGACCATCACC-3' (SEQ ID NO: 9) and 5'-GCAATGAAATTTGTTGAA-3' (SEQ ID NO: 10)) were used, and (2) a series of 10-fold dilutions of human DNA served as the templates. FIG. 8 shows amplification plots of the reactions starting with $10^5$ copies of human DNA down to 10 copies either with SYBR Green I or with AOAO-12. The inset shows that the Ct value is reversibly correlated with the logarithm of starting copy number monitored with both dyes. AOAO-12 is evidently superior to SYBR Green I in signal strength.

Example 47

TO, TOTO-1 and TOTO12 in qPCR

This example demonstrates the improved property of TOTO-12 over TO (thiazole orange, an asymmetric cyanine dye), or TOTO-1 in qPCR. All real-time amplifications were performed as in Example 5, except that TO, TOTO-1 and TOTO-12 were used. As shown in FIG. 11, TOTO-1 completely inhibited the PCR reaction, while TOTO-12 gave improved Ct and improved fluorescence intensity relative to TO in qPCR. The TOTO-12 dimeric dye is superior to each of the TO and TOTO-1 dyes.

Example 48

Absorbance and Fluorescence of AORO-7

In a manner similar to that described in connection with Example 42, the absorbance spectra of AORO-7 were taken alone or in the presence of 2 µg/ml of salmon sperm DNA in PBS buffer, as shown in FIG. 12. The emission spectra of AORO-7 bound to DNA are shown in FIG. 13. The heterodimeric dye AORO-7 comprises a monomeric AO dye and a fluorescent non-nucleic acid rosamine RO dye. Two emission peaks, contributed by AO and RO moieties, respectively, were recorded. It was possible to record qPCR with AORO-7 in Channel 1 with the excitation set at 490 nm and the emission collected at 530 nm, or Ex490/Em530, or in Channel 3 with Ex580/Em630, on a Chromo4 from Bio-Rad Laboratories (Hercules, Calif.), but only weakly in Channel 2 (Ex520/Em570) (data not shown). As the fluorescence resonance energy transfer (FRET) effect is negligible, either monomeric dye constituent, AO or RO, can be chosen as the reporter dye.

Example 49

Heterodimer Dye AORO-7 in qPCR

The example demonstrates the utility of AORO-7 in qPCR. Real time amplifications were performed as in Example 5, except that AORO-7 with an optical density of 0.025 at 600 nm in the final solution was used. As shown in FIG. 14, AORO-7 may be used effectively be used to monitor the qPCR reaction course and to detect the melting curve of the amplicon (inset). The finding that this qPCR was monitored in Channel 3 (Ex580/Em630) on an iCycle IQ Multiple-Color Real-Time PCR Detection System from Bio-Rad Laboratories (Hercules, Calif.) provides an example that almost any dye of desirable wavelength may be tailored into a DNA reporter dye in qPCR by methods disclosed herein, thus widening the spectral use for qPCR monitoring. At present, most TaqMan probes use FAM or VIC, which occupy the same channels of SYBR Green I. It would be advantageous to use a sequence-specific-probe, such as a TaqMan probe, and a sequence-non-specific dye of different wavelength, such as AORO-7, in qPCR, wherein the probe provides sequence specificity and the dye provides other parameters of the amplicon, such as melting temperatures.

Example 50

Melting Peaks Monitored with AOAO-12

SYBR Green I was reported to be advantageous in that the melting temperature of an amplicon could be detected after qPCR amplification. The melting temperature provides valuable information about the amplicon, as it is a function of the size and GC content of the amplicon. No melting temperatures could be collected from TaqMan reactions. Melting curves from four amplicons, i.e., HMBS (SEQ ID NO: 4), RPL4 (SEQ ID NO: 5), SDHA (SEQ ID NO: 6), and TBP (SEQ ID NO: 7) were measured from reactions amplified in the presence of AOAO-12 (Panel A) or SYBR Green (Panel B) and are presented in FIG. 15. The melting peaks collected with AOAO-12 correlated well with those collected with SYBR Green I. As AOAO-12 binds DNA with high affinity but less tightly than SYBR Green I, melting temperatures from AOAO-12 are about 2 degrees lower than those from SYBR Green I. As higher concentrations of AOAO-12 could be used in real time PCR reactions, melting peaks are markedly higher. The data demonstrate the relative utility of AOAO-12.

It has been reported that qPCR reactions with SYBR Green I tend to form primer-dimers, and the tendency is closely related to the concentration of SYBR Green I. It has been postulated that SYBR Green I binds to DNA so tightly that it interferes with the performance of Taq DNA polymerase. As AOAO-12 has less affinity to DNA, the interference should be alleviated. This property of AOAO-12 is evident from FIG. 15, in that the HMBS amplification reaction in the presence of SYBR Green I has an extra primer dimer peak, while the same amplification in the presence of AOAO-12 exhibits only a single, clean, and specific peak.

Example 51

Stability of AOAO Dyes

The stability of dimeric dyes comprising monomeric AO was demonstrated. Specifically, AOAO-12 was kept in PCR reaction buffers with PCR products. The mixture was heated to 96° C. for 40 minutes. During the heating course, the mixture was brought down to 60° C. briefly to monitor the fluorescence. As shown in FIG. 16, AOAO-12 is stable at 96° C. for 40 minutes substantially without loss of fluorescence. The data demonstrate the robustness of AOAO-12 in PCR.

Example 52

Preparation of TOTO-13 (Dye No. 29 of Table 2)

The dye (102 mg) was prepared using the procedure to synthesize AOAO-2 (Dye No. 7 of Table 2) from N-carboxypentyl thiazole orange (102 mg, 0.23 mmole) (Example 31) and 4,7,10-trioxa-1,13-tridecanediamine (23 mg, 0.1 mole).

Example 53

Preparation of N-(5-carboxypentyl)-4-(4-(dimethylamino)styryl)pyridinium bromide A mixture of 4-N,N-dimethylaminobenzaldehyde (3 g, 20 mmoles), N-(5-carboxy-pentyl)picolinium bromide (5.6 g, 20 mmoles) and piperidine (2 mL) in ethanol (100 mL) was heated at 60° C. overnight. The mixture was evaporated to dryness in vacuo. The residue was redissolved in methanol and then precipitated with ether to give the product (6.7 g).

Example 54

Preparation of STST-19 (Dye No. 31 of Table 2)

The dye (85 mg) was prepared using the procedure to prepare AOAO-2 (Example 7) from N-(5-carboxypentyl)-4-(4-(dimethylamino)styryl)pyridinium bromide (Example 53) (200 mg, 0.5 mmole) and 2,2'-oxybis(ethylamine) dihydrochloride (36 mg, 0.2 mmoles).

Example 55

Preparation of STST-27 (Dye No. 30 of Table 2)

The dye (81.8 mg) was prepared using the procedure to prepare AOAO-2 (Example 7) from N-(5-carboxypentyl)-4-(4-(dimethylamino)styryl)pyridinium bromide (Example 53) (200 mg, 0.5 mmole) and 4,7,10-trioxa-1,13-tridecanediamine (44 mg, 0.2 mmoles).

A useful dye, such as a dimeric dye or a trimeric dye, has been described herein. Such a dye may have any of a number of desirable properties, such as relatively low background fluorescence, relatively low PCR inhibition, good fluorescent signal strength, and good stability, for example. Generally, a dye having at most one positive charge may have any of a number of applications, such as use in the labeling of another molecule, and such as use in the detection of the presence or absence of nucleic acid, for example. Further, generally, such a dye that is substantially neutral, has any of a number of applications, such as use in PCR processes or use in the detection of the presence or absence of nucleic acid, or use in quantitative real-time PCR, for example.

A number of useful dimeric and trimeric dyes have been described. By way of example, a dye that is suitable for covalent conjugation with, or labeling of, another molecule to confer the nucleic acid-detecting capability of the dye on the molecule; a dye that is suitable for detecting the presence or absence of nucleic acid in a sample that may or may not comprise nucleic acid; and a dye that is suitable for detecting nucleic acid formation or a lack thereof in a sample, such as a sample that undergoes a process suitable for nucleic acid amplification should the sample comprise a target nucleic acid, have been described. A method for preparing any of the foregoing dyes and a method of using any of the foregoing dyes have also been described. Any method of using a composition described herein is contemplated herein. A kit suitable for determining nucleic acid formation or a lack thereof in a sample, which comprises a suitable dye of the present invention, and a suitable composition sufficient for amplification of a target nucleic acid in a sample should it comprise a target nucleic acid, is contemplated herein, as is any kit comprising a composition described herein that has useful application.

Various modifications, processes, as well as numerous structures relating to the description herein may be applicable, as will be readily apparent to those of ordinary skill in the art, upon review of the specification. Various references, publications, provisional and non-provisional United States or foreign patent applications, and/or United States or foreign patents, have been identified herein, each of which is incorporated herein in its entirety by this reference. Various aspects and features may have been explained or described in relation to understandings, beliefs, theories, underlying assumptions, and/or working or prophetic examples, although it will be understood that any such understanding, belief, theory, underlying assumption, and/or working or prophetic example is not binding. Although the various aspects and features have been described with respect to various embodiments and examples herein, it will be understood that any of same is not limiting with respect to the full scope of the appended claims.

The invention claimed is:
1. A labeled biomolecule having a structure of

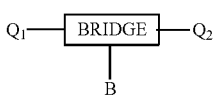

wherein B is the biomolecule conjugated to a dye, said dye comprising a BRIDGE, $Q_1$, and $Q_2$, wherein said conjugation is mediated via a reactive group attached to said BRIDGE;
$Q_1$ is a fluorescent nucleic acid dye constituent;
$Q_2$ is a fluorescent nucleic acid dye constituent;
$Q_1$ and $Q_2$ may be the same or different, wherein:
(i) each of $Q_1$ and $Q_2$ is independently a phenanthridium dye of Formula I:

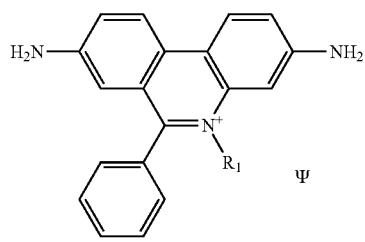

(Formula I)

$R_1$ represents where BRIDGE attaches to the structure; and Ψ is an anion; or
(ii) each of $Q_1$ and $Q_2$ is independently an asymmetric cyanine dye, wherein each of $Q_1$ and $Q_2$ dye constituents has a structure of Formula II:

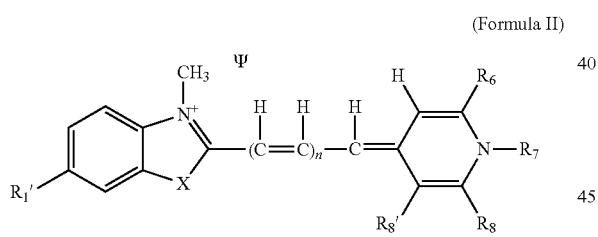

(Formula II)

wherein $R_1'$ of Formula II is H; alkyl or alkenyl having 1 carbon to 6 carbons, inclusive; a halogen; —$OR_9$; —$SR_{10}$; —$NR_{11}R_{12}$; —CN; —NH(C=O)$R_{13}$; —NHS(=O)$_2R_{14}$; —C(=O)NH$R_{15}$; or a substituent associated with minor groove binding; or represents where BRIDGE attaches to the structure;
when $R_1'$ of Formula II comprises at least one of $R_9$, $R_{10}$, $R_{11}$, $R_{12}$, $R_{13}$, $R_{14}$, and $R_{15}$, any said one of $R_9$, $R_{10}$, $R_{11}$, $R_{12}$, $R_{13}$, $R_{14}$ and $R_{15}$, independently, is H or alkyl having 1 carbon to 12 carbons, inclusive, optionally incorporating 1 to 2 nitrogen(s), inclusive, or an aryl;
when $R_1'$ of Formula II comprises $R_{11}$ and $R_{12}$, $R_{11}$ and $R_{12}$ may in combination form a 5- or 6-membered, saturated or unsaturated ring, which optionally comprises at least one hetero atom selected from N and O;
X of Formula II is selected from O and S;
n of Formula II is selected from 0, 1, and 2;

$R_6$ of Formula II is H; alkyl or alkenyl having 1 carbon to 10 carbons, inclusive, optionally comprising at least one hetero atom selected from N, O, and S; a halogen; —$OR_{16}$; —$SR_{16}$; —$NR_{16}R_{17}$; or a substituted or an unsubstituted aryl, optionally comprising 1 to 3 hetero atom(s), inclusive, selected from N, O, and S; or represents where BRIDGE attaches to the structure;
$R_7$ of Formula II is H; alkyl or alkenyl having 1 carbon to 10 carbons, inclusive, optionally comprising an aryl and at least one hetero atom selected from N, O, and S; or a substituted or an unsubstituted aryl optionally comprising 1 to 3 hetero atom(s), inclusive, selected from N, O, and S; or represents where BRIDGE attaches to the structure;
$R_8$ and $R_8'$ of Formula II in combination form a fused aromatic ring, which may be further substituted 1 to 4 time(s), inclusive, independently, by C1-C2, inclusive, alkyl, C1-C2, inclusive, alkoxy, C1-C2, inclusive, alkylmercapto, or a halogen;
each of $R_{16}$ and $R_{17}$ independently is H; alkyl having 1 carbon to 12 carbons, inclusive, optionally incorporating 1 to 2 nitrogen(s) or an aryl; or $R_{16}$ and $R_{17}$ may in combination form a 5- or 6-membered saturated or unsaturated ring, which optionally comprises at least one hetero atom selected from N and O;
only one of $R_1'$, $R_6$, and $R_7$ of Formula II represents where BRIDGE attaches to the structure; and
Ψ of Formula II is an anion; or
(iii) each of $Q_1$ and $Q_2$ is independently an acridine dye of Formula III:

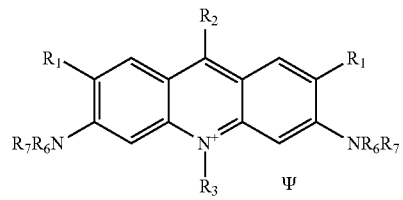

Formula III wherein each $R_1$ of Formula III is independently H or a C1-C2, inclusive, alkyl;
one of $R_2$ and $R_3$ of Formula III represents where BRIDGE attaches to the structure;
when $R_2$ represents where BRIDGE attaches to the structure, $R_3$ is H or —$CH_3$;
when $R_3$ represents where BRIDGE attaches to the structure, $R_2$ is selected from H, —$CH_3$, —$NH_2$, —$NHCH_3$, —CN, and —C(=O)$NH_2$;
each $R_6$ of Formula III is independently H or a C1-C2, inclusive, alkyl;
each $R_7$ of Formula III is independently H or a C1-C2, inclusive, alkyl;
for each pair of adjacent $R_6$ or $R_7$ and $R_1$, independently, $R_6$ or $R_7$ and $R_1$ may in combination form a 5- or 6-membered, saturated or unsaturated ring;
Ψ of Formula III is an anion; and
wherein the BRIDGE comprises:

-$L_1$-[$A^1$-($CH_2$)$_\alpha$-]$_a$[$A^2$-($CH_2$)$_\beta$-]$_b$[$A^3$-($CH_2$)$_\gamma$-]$_c$[$A^4$-($CH_2$)$_\delta$-]$_d$[$A^5$-($CH_2$)$_\epsilon$-]$_e$[$A^6$-($CH_2$)$_\zeta$-]$_f$[$A^7$-($CH_2$)$_\eta$-]$_g$[$A^8$-($CH_2$)$_\theta$-]$_h$[$A^9$-($CH_2$)$_\tau$-]$_i$-$A^{10}$-$L_2$- wherein each of $L_1$ and $L_2$, independently, is a moiety comprising a single bond; a polymethylene unit having 1 carbon to about 12 carbons, inclusive, optionally comprising at least one hetero atom selected from N, O and S; or an aryl optionally comprising at least one hetero atom selected from N, O and S;

$L_1$ is covalently bound to one dye constituent of the $Q_1$ dye constituent and the $Q_2$ dye constituent;

$L_2$ is covalently bound to the dye constituent of the $Q_1$ dye constituent and the $Q_2$ that is other than said one dye constituent;

each of $A^1$, $A^2$, $A^3$, $A^4$, $A^5$, $A^6$, $A^7$, $A^8$, $A^9$, and $A^{10}$, independently, is a nucleic-acid-binding-enhancing-group (NABEG); a branched alkyl optionally comprising at least one hetero atom selected from N, O and S; or at least one saturated 5- or 6-membered ring, optionally comprising at least one hetero atom selected from N, O and S;

each of $\alpha$, $\beta$, $\gamma$, $\delta$, $\epsilon$, $\zeta$, $\eta$, $\theta$, and $\tau$, independently, is zero or an integer from 1 to about 20, inclusive;

each of a, b, c, d, e, f, g, h, and i, independently, is zero or an integer from 1 to about 20, inclusive; and one of $A^1$, $A^2$, $A^3$, $A^4$, $A^5$, $A^6$, $A^7$, $A^8$, $A^9$, and $A^{10}$ has the formula:

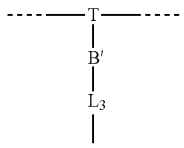

wherein T is a substituted carbon, a substituted nitrogen, or an aryl optionally comprising at least one hetero atom selected from O, N and S;

$L_3$ is covalently bound to B and is a moiety comprising a single bond; a polymethylene unit having 1 carbon to about 12 carbons, inclusive, optionally comprising at least one hetero atom selected from N, O and S; or an aryl optionally comprising at least one hetero atom selected from N, O and S; and B' has the formula:

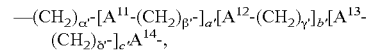

wherein —$(CH_2)_{\alpha'}$ is covalently linked to T and $A^{14}$ is covalently linked to $L_3$;

each of $A^{11}$, $A^{12}$, $A^{13}$, and $A^{14}$ is independently a nucleic-acid-binding-enhancing-group (NABEG), a branched alkyl optionally comprising at least one hetero atom selected from N, O and S; or at least one saturated 5- or 6-membered ring optionally comprising at least one hetero atom selected from N, O and S;

each of $\alpha'$, $\beta'$, $\gamma'$, and $\delta'$ is independently zero or an integer from 1 to about 20, inclusive; and each of a', b', and c' is independently zero or an integer from 1 to about 20, inclusive.

2. The labeled biomolecule according to claim 1, wherein the BRIDGE is a substantially aliphatic linker comprising from about 15 to about 150 non-hydrogen atoms and up to one positive charge.

3. The labeled biomolecule according to claim 1, wherein B is selected from a nucleotide, an oligonucleotide, a peptide, a protein, a hapten, a drug, a microparticle, a synthetic polymer, a natural polymer, a biological cell, and a virus.

4. The labeled biomolecule according to claim 3, wherein B is a nucleotide or an oligonucleotide.

5. The labeled biomolecule according to claim 1, wherein $Q_1$ and $Q_2$ are each independently an asymmetric cyanine dye.

6. The labeled biomolecule according to claim 5, wherein $Q_1$ and $Q_2$ are each thiazole orange.

* * * * *

UNITED STATES PATENT AND TRADEMARK OFFICE
CERTIFICATE OF CORRECTION

PATENT NO. : 9,580,749 B2  
APPLICATION NO. : 13/968122  
DATED : February 28, 2017  
INVENTOR(S) : Fei Mao et al.

Page 1 of 1

It is certified that error appears in the above-identified patent and that said Letters Patent is hereby corrected as shown below:

In the Claims

Claim 1, Column 116, Line 62, delete "-$L_1$-[$A^1$-($CH_2$)$_\alpha$-]$_a$[$A^2$-($CH^2$)$_\beta$-]$_b$[$A^3$-($CH_2$)$_\gamma$-]$_c$[$A^4$-($CH^2$)$_\delta$-]$_d$[$A^5$-($CH^2$)$_\varepsilon$-]$_e$[$A^6$-($CH^2$)$_\zeta$-]$_f$[$A_7$-($CH_2$)$_\eta$-]$_g$[$A^8$-($CH^2$)$_\theta$-]$_h$[$A^9$-($CH_2$)$_\iota$-]$_i$-$A^{10}$-$L_2$-" and insert -- -$L_1$-[$A^1$-($CH_2$)$_\alpha$-]$_a$[$A^2$-($CH_2$)$_\beta$-]$_b$[$A^3$-($CH_2$)$_\gamma$-]$_c$[$A^4$-($CH_2$)$_\delta$-]$_d$[$A^5$-($CH_2$)$_\varepsilon$-]$_e$[$A^6$-($CH_2$)$_\zeta$-]$_f$[$A^7$-($CH_2$)$_\eta$-]$_g$[$A^8$-($CH_2$)$_\theta$-]$_h$[$A^9$-($CH_2$)$_\iota$-]$_i$-$A^{10}$-$L_2$- --.

Claim 1, Column 117, Line 16, delete "τ" and insert -- ι --.

Claim 1, Column 118, Line 5, delete "-($CH_2$)$_{\alpha'}$-[$A^{11}$-($CH_2$)$_{\beta'}$-]$_{a'}$[$A^{12}$-($CH_2$)$_{\gamma'}$-]$_{b'}$[$A^{13}$-($CH_2$)$_{\delta'}$-]$_{c'}$$A^{14}$-," and insert -- -($CH_2$)$_{\alpha'}$-[$A^{11}$-($CH_2$)$_{\beta'}$-]$_{a'}$[$A^{12}$-($CH_2$)$_{\gamma'}$-]$_{b'}$[$A^{13}$-($CH_2$)$_{\delta'}$-]$_{c'}$$A^{14}$-, --.

Signed and Sealed this  
Third Day of July, 2018

Andrei Iancu  
*Director of the United States Patent and Trademark Office*

SEQUENCE LISTING

<160> NUMBER OF SEQ ID NOS: 10

<210> SEQ ID NO 1
<211> LENGTH: 164
<212> TYPE: DNA
<213> ORGANISM: Homo sapiens

<400> SEQUENCE: 1
aggtcttcac aggtcatatg gggaagctgg taccccctgaa ggagaccatc aaaggattcc    60
agcagatttt ggcaggtgaa tatgaccatc tcccagaaca ggccttctat atggtgggac   120
ccattgaaga agctgtggca aaagctgata agctggctga agag                    164

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gaggtcttca caggtcata                                                  19

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ctcttcagcc agcttatc                                                   18

<210> SEQ ID NO 4
<211> LENGTH: 249
<212> TYPE: DNA
<213> ORGANISM: Homo sapiens

<400> SEQUENCE: 4
gtctagacgg ctcagatagc atacaagaga ccatgcaggc taccatccat gtccctgccc    60
agcatgaaga tggccctgag gatgacccac agttggtagg catcactgct cgtaacattc   120
cacgagggcc ccagttggct gcccagaact tgggcatcag cctggccaac ttgttgctga   180
gcaaaggagc caaaaacatc ctggatgttg cacggcagct taacgatgcc cattaactgg   240
tttgtgggg                                                            249

<210> SEQ ID NO 5
<211> LENGTH: 231
<212> TYPE: DNA
<213> ORGANISM: Homo sapiens

<400> SEQUENCE: 5
ccatgcacaa gatgattaat acagatctta gcagaatctt gaaaagccca gagatccaaa    60
gagcccttcg agcaccacgc aagaagatcc atcgcagagt cctaaagaag aacccactga   120
aaaacttgag aatcatgttg aagctaaacc catatgcaaa gaccatgcgc cggaacacca   180
ttcttcgcca ggccaggaat cacaagctcc gggtggataa ggcagctgct g            231

<210> SEQ ID NO 6
<211> LENGTH: 139
<212> TYPE: DNA
<213> ORGANISM: Homo sapiens

<400> SEQUENCE: 6
gattgatgag tacgattact ccaagcccat ccagggggcaa cagaagaagc cctttgagga    60
gcactggagg aagcacaccc tgtcctttgt ggacgttggc actgggaagg tcactctgga   120
atatagaccc gtaatcgac                                                139

<210> SEQ ID NO 7
<211> LENGTH: 229
<212> TYPE: DNA
<213> ORGANISM: Homo sapiens

<400> SEQUENCE: 7
agcaagaaaa tatgctagag ttgtacagaa gttgggtttt ccagctaagt tcttggactt    60
caagattcag aatatggtgg ggagctgtga tgtgaagttt cctataaggt tagaaggcct   120
tgtgctcacc caccaacaat ttagtagtta tgagccagag ttatttcctg gtttaatcta   180
cagaatgatc aaacccagaa ttgttctcct tattttttgtt tctggaaaa              229

<210> SEQ ID NO 8
<211> LENGTH: 140
<212> TYPE: DNA
<213> ORGANISM: Homo sapiens

<400> SEQUENCE: 8
gagcccagtg acactatcga gaacgtcaaa gcaaagatcc aagacaagga aggcattcct    60
cctgaccagc agaggttgat ctttgccgga aagcagctgg aagatgggcg caccctgtct   120
gactacaaca tccagaaaga                                               140

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
actggtaaga ccatcacc                                                  18

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gcaatgaaat ttgttgaa                                                  18